US009926603B2

(12) United States Patent
Sozzi et al.

(10) Patent No.: US 9,926,603 B2
(45) Date of Patent: Mar. 27, 2018

(54) MICRO-RNA BIOMARKERS AND METHODS OF USING SAME

(71) Applicant: BIOMIRNA HOLDINGS LTD., Dublin (IE)

(72) Inventors: Gabriella Sozzi, Milan (IT); Ugo Pastorino, Milan (IT); Mattia Boeri, Milan (IT)

(73) Assignee: Biomirna Holdings Ltd., Dublin (IE)

(*) Notice: Subject to any disclaimer, the term of this patent is extended or adjusted under 35 U.S.C. 154(b) by 0 days.

(21) Appl. No.: 14/310,787

(22) Filed: Jun. 20, 2014

(65) Prior Publication Data

US 2015/0045233 A1 Feb. 12, 2015

Related U.S. Application Data

(63) Continuation of application No. 13/367,582, filed on Feb. 7, 2012, now abandoned.

(60) Provisional application No. 61/522,328, filed on Aug. 11, 2011.

(30) Foreign Application Priority Data

Feb. 7, 2011 (IT) .................. MI2011A000172
Feb. 7, 2011 (IT) .................. MI2011A000173
Feb. 7, 2011 (IT) .................. MI2011A000174

(51) Int. Cl.
*C12Q 1/00* (2006.01)
*A61P 3/00* (2006.01)
*A61P 35/00* (2006.01)
*C12Q 1/68* (2018.01)

(52) U.S. Cl.
CPC ...... *C12Q 1/6886* (2013.01); *C12Q 2600/118* (2013.01); *C12Q 2600/158* (2013.01); *C12Q 2600/178* (2013.01)

(58) Field of Classification Search
CPC ............ C12Q 1/6886; C12Q 2600/158; C12Q 2600/178; C12Q 2600/118
USPC ..... 435/6.11, 91.1, 91.31, 6.12, 6.1; 514/44; 536/23.1, 24.5; 424/9.1; 506/9, 16, 39, 7
See application file for complete search history.

(56) References Cited

U.S. PATENT DOCUMENTS

2010/0010072 A1 1/2010 Dmitrovsky et al.
2012/0309645 A1* 12/2012 Keller .................. C12Q 1/6886
   506/9
2013/0035251 A1* 2/2013 Keller .................. C12Q 1/6886
   506/9
2013/0184175 A1* 7/2013 Beaudenon-Huibregtse
   .......................... C12Q 1/6886
   506/9
2014/0018411 A1* 1/2014 Croce .................. C12N 15/111
   514/44 A
2014/0031415 A1* 1/2014 Brown .................. C12N 15/111
   514/44 A

FOREIGN PATENT DOCUMENTS

| CN | 101804208 A | 8/2010 |
| WO | WO 2007081720 A2 | 7/2007 |
| WO | WO 2009052386 A1 | 4/2009 |
| WO | WO 2009070653 A1 | 6/2009 |
| WO | WO2009147525 A1 | 12/2009 |
| WO | WO2010099161 A1 | 9/2010 |
| WO | WO2012/107841 | 8/2012 |

OTHER PUBLICATIONS

Wang et al, Curr. Cancer Drug Targets, vol. 9, pp. 572-594 (2009).*
"Agilent High-Resolution Microarray Scanner." Aug. 20, 2010, retrieved Aug. 26, 2011. www.chem.agilent.com/Library/datasheets/Public/5990-6404en_lo.pdf.
"Agilent Human, Mouse, and Rat miRNA Microarrays." Jan. 16, 2009, retrieved Aug. 26, 2011. www.chem.agilent.com/Library/brochures/5989-7688en_lo.pdf.
Boeri et al. "MicroRna Signatures in Tissues and Plasma Predict Development and Prognosis of Computed Tomography Detected Lung Cancer." *PNAS.* 108(9):3713-3718 (2011).
Du et al. "miR-93, miR-98, and miR-197 Regulate Expression of Tumor Suppressor Gene FUS1." Mol. Cancer Res. 7.8(2009):1234-1243.
Erdmann et al. "Down-Regulation of Selected MicroRNAs Correlates With Expression of Prostate Cancer Associated Genes." *J. Urol.* 183.4(2010):e503. (Abstract #1300).
Karkera et al. "The mirR-21:miR-221 Ratio as a Serum-Based Diagnostic for Non-Small Cell Lung Cancer." *Proc. Am. Assoc. Cancer Res. Ann. Meeting.* 51(2010):736. (Abstract #3015).
Neely et al. "A MicroRNA Expression Ratio Defining the Invasive Phenotype in Bladder Tumors." *Urol. Oneal. Semin. Orig. Invest.* 28.1 (2010):39-48.
Sozzi et al. "MicroRNA Expression Profile of CT Screening Detected Lung Cancer." *Proc. Am.Assoc. Cancer Res. Ann. Meeting.* 51 (Apr. 2010):737-738. (Abstract #3021).
Tanaka et al. "Down-Regulation of miR-92 in Human Plasma is a Novel Marker for Acute Leukemia Patients." *PLoS One.* 4.5(2009):E5532.1-E5532.5.
Wang et al.: "Potential Uses of MicroRNA in Lung Cancer Diagnosis, Prognosis, and Therapy," *Curr. Cancer Drug Targets* 9.4(2009):572-594.
International Search Report issued for application No. PCT/IB2012/000567, mailed on Dec. 4, 2012.

* cited by examiner

*Primary Examiner* — Jane J Zara
(74) *Attorney, Agent, or Firm* — Cooley LLP; Ivor R. Elrifi; Matthew Pavao

(57) ABSTRACT

A procedure and an apparatus are described for identifying individuals at risk of pulmonary tumour and/or for diagnosing a pulmonary tumour using the study of levels of expression of miRNA in the blood or another biological fluid. Also described are a method and a compound for reducing or eliminating a risk of pulmonary tumour by rebalancing the miRNAs that are underexpressed or overexpressed.

15 Claims, 20 Drawing Sheets

Figure 1

|  | Training set<br>Trial INT-IEO<br>N=18 | Validation set<br>MILD trial<br>N=22 |
|---|---|---|
| Gender | | |
| Male | 11 (61.1%) | 16 (72.7%) |
| Female | 7 (38.9%) | 6 (27.3%) |
| Age (years) | 57.5 ± 5.6 (s.d.) | 61.9 ± 7 (s.d.) |
| Smoking habit (Pack-Years index) | 60.3 ± 23.8 (s.d.) | 55 ± 21 (s.d.) |
| Screening year of disease detection | | |
| 1$^{st}$ year | 1 (5.6%) | |
| 2$^{nd}$ year | 6 (33.3%) | 5 (22.7%) |
| 3$^{rd}$-5$^{th}$ year | 11 (61.1%) | 14 (63.6%) |
| Interval cancers | | 3 (13.7%) |
| Histotype | | |
| ADC (adenocarcinoma) | 13 (72.2%) | 14 (63.6%) |
| SCC (squamous carcinoma) | 3 (16.7%) | 4 (18.2%) |
| other | 2 (11.1%) | 4 (18.2%) |
| Stage | | |
| Ia-Ib | 11 (61.1%) | 15 (68.2%) |
| II-III-IV | 7 (38.9%) | 7 (31.8%) |
| Median Follow up (months) | 67* | 14 (min = 4, max = 46) |
| Prognosis | | |
| Disease free | 10 (55.6%) | 16 (72.7%) |
| Alive with disease | | 1 (4.6%) |
| Dead | 8 (44.4%) | 5$^{†}$ (22.7%) |
| Control Pools$^{‡}$ | 5 (5-7 samples) | 10 (5-7 samples) |

* an outlier has a follow-up of 35 months.
$^{†}$ a subject died for clinical complications.
$^{‡}$ disease free individuals pooled by sex, age and smoking habit to best match with patient's characteristics.

Figure 5: risk of manifesting a pulmonary tumor - Validation set
Using all 15 miRNAs of Table I
30 Ratios of Table III
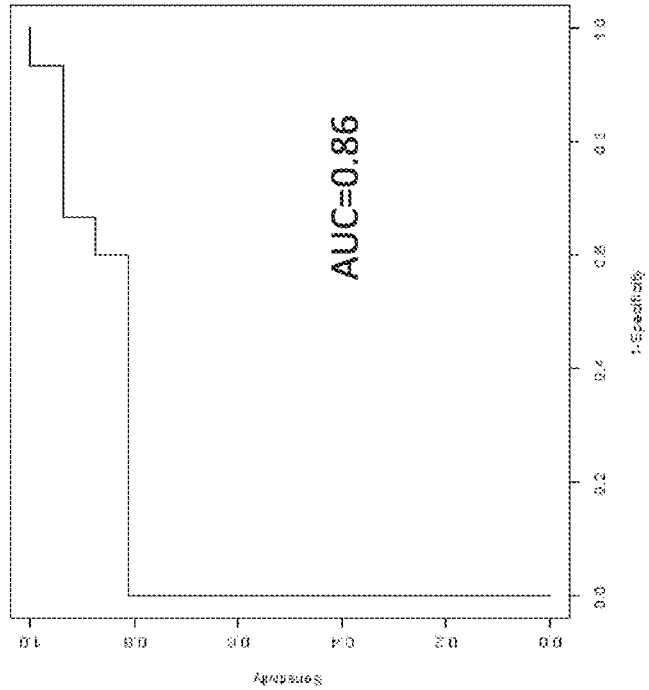
Using 6 best miRNAs of Table Ib
9 Ratios of Table IIIb
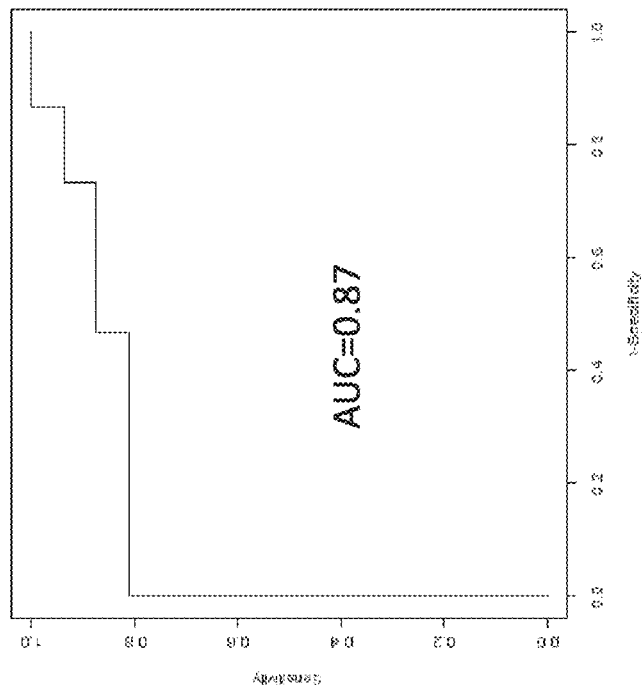

Figure 6: risk of manifesting an aggressive pulmonary tumor - Validation set
Using all 16 miRNAs of Table II
 28 Ratios of Table IV 
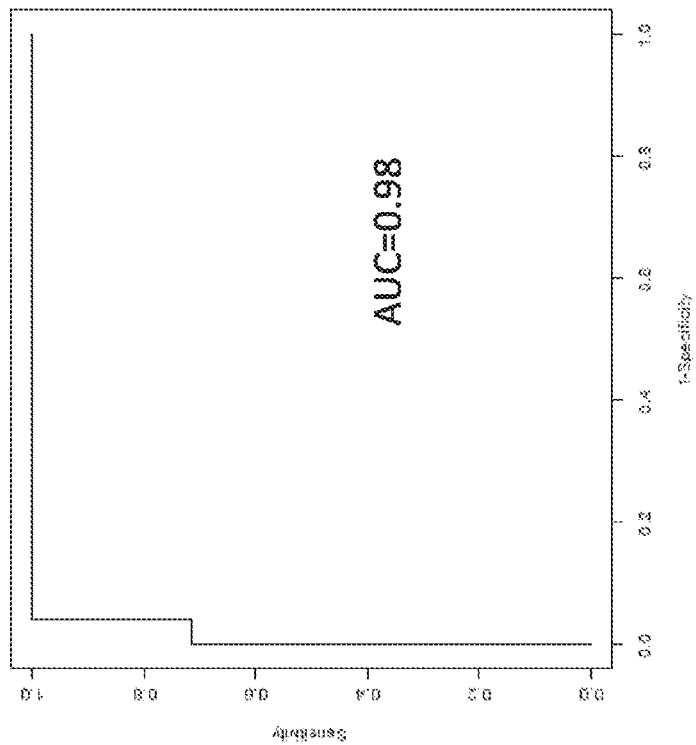
AUC=0.99
Using 6 best miRNAs of Table IIb
 9 Ratios of Table IVb 
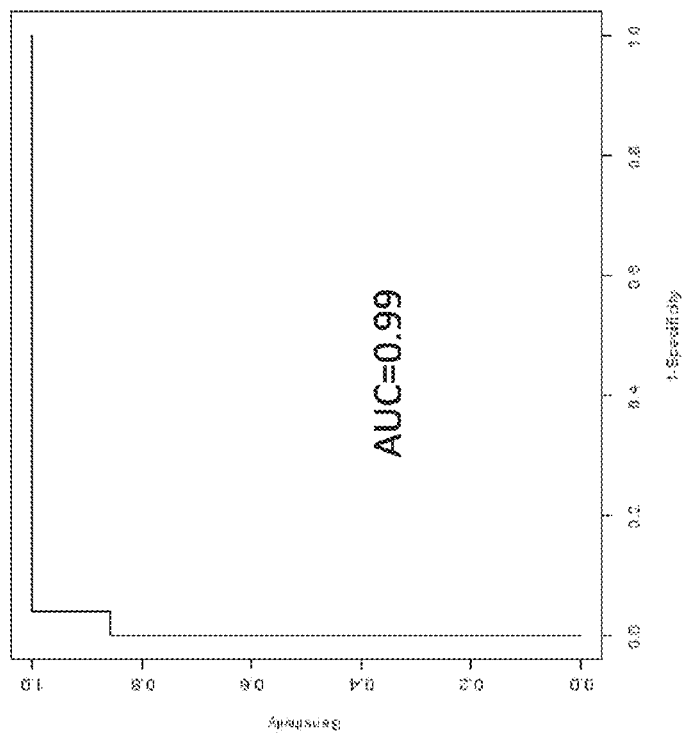
AUC=0.98

Figure 7: risk of manifesting an aggressive pulmonary tumor – Validation set
Using all 18 miRNAs of Table V  36 Ratios of table VII  ROC curve
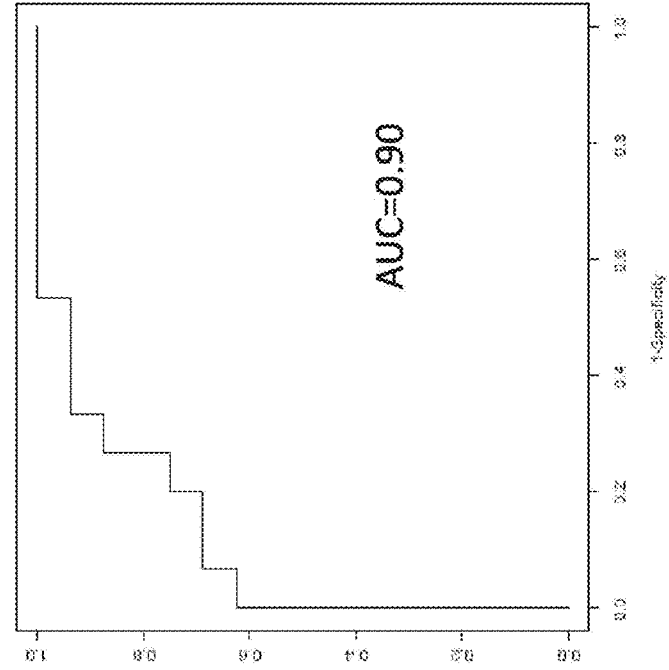
AUC=0.86
Using 6 best miRNAs of Table Vb  9 Ratios of table VIIb  ROC curve
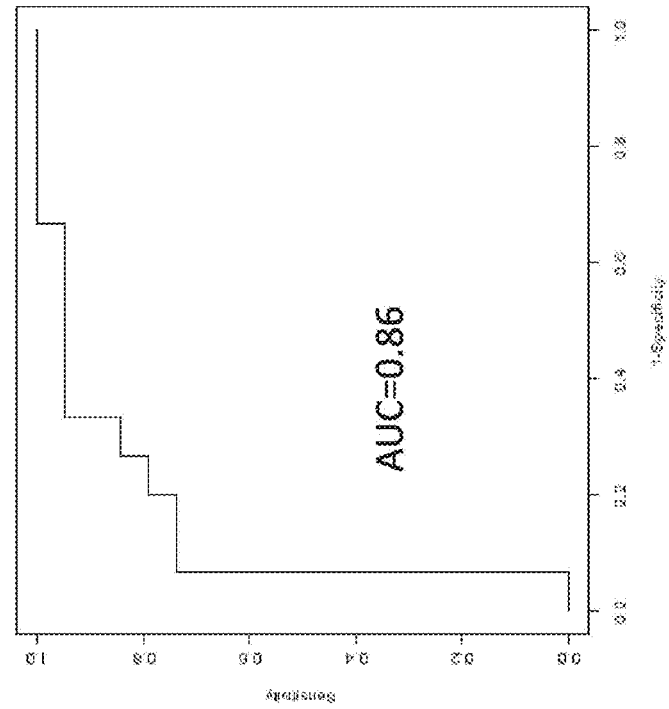
AUC=0.90

Figure 8: risk of manifesting an aggressive pulmonary tumor – Validation set
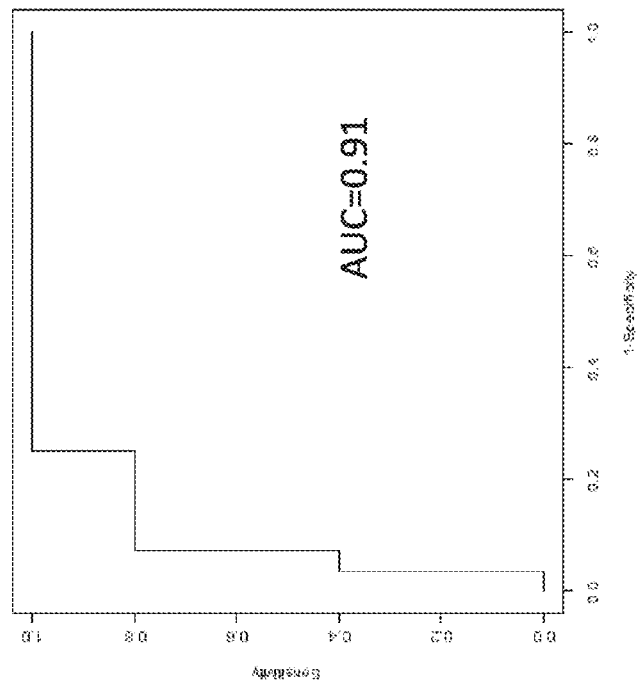
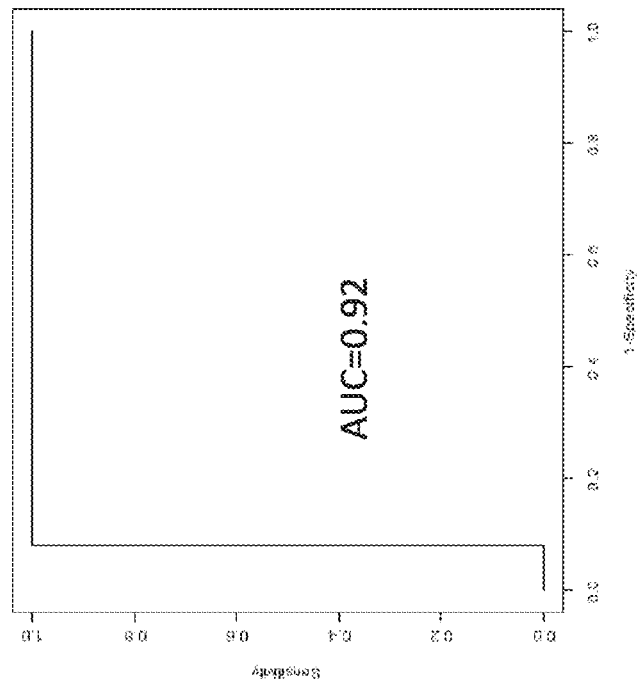

Observed survival by stage

Observed survival by year of screening

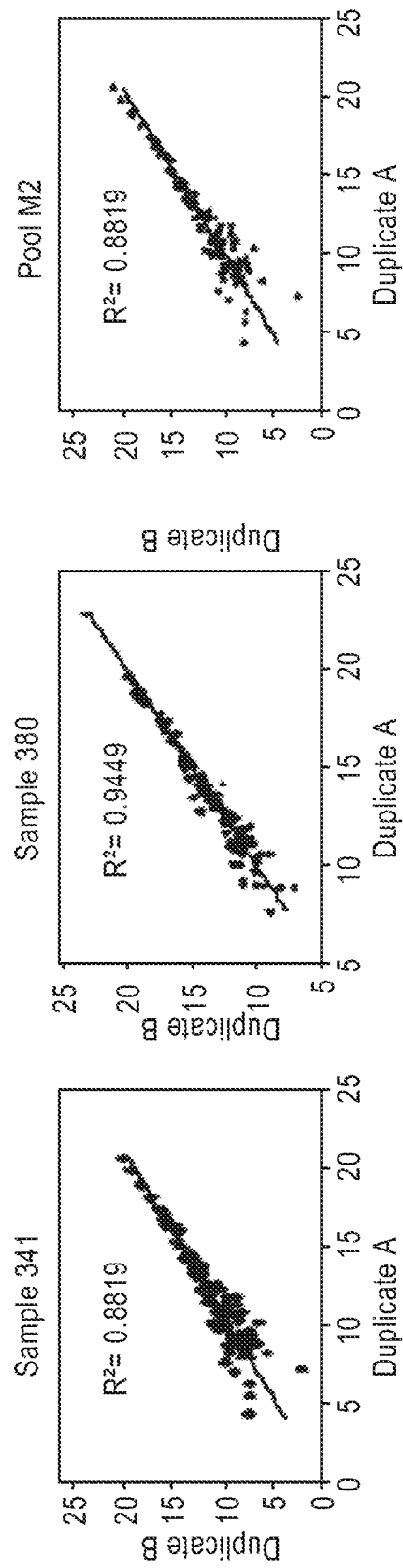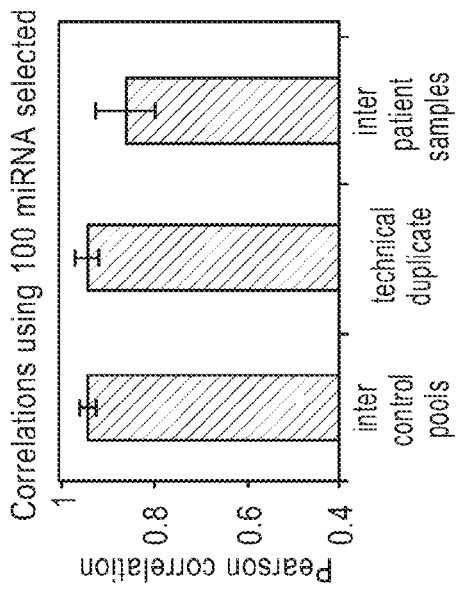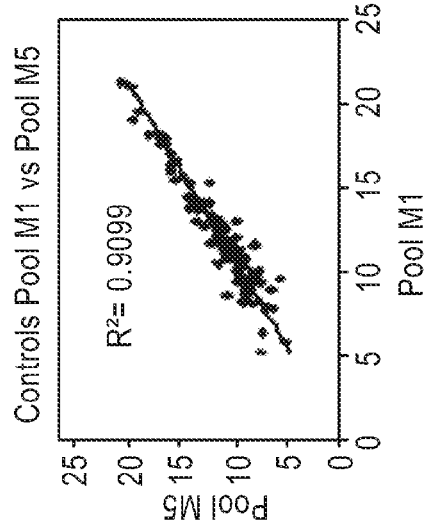

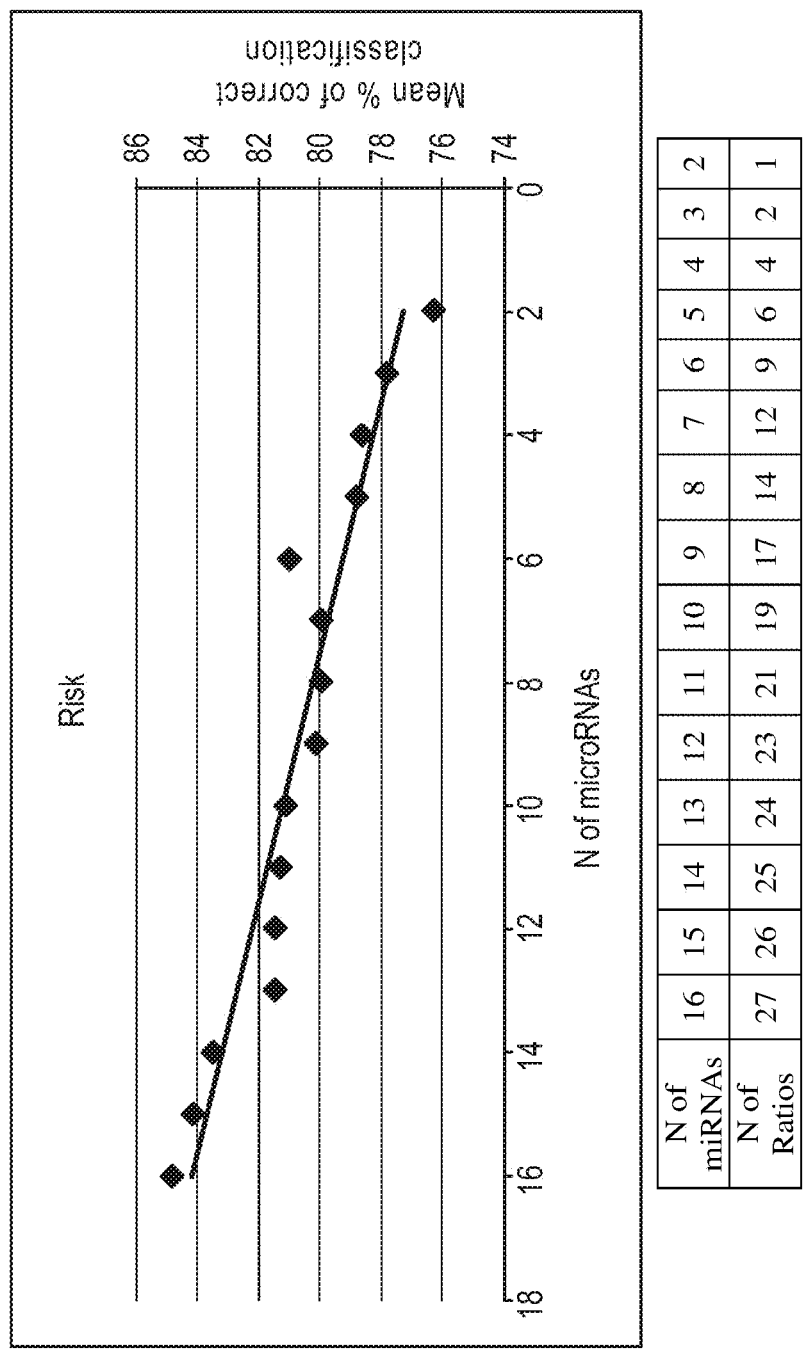

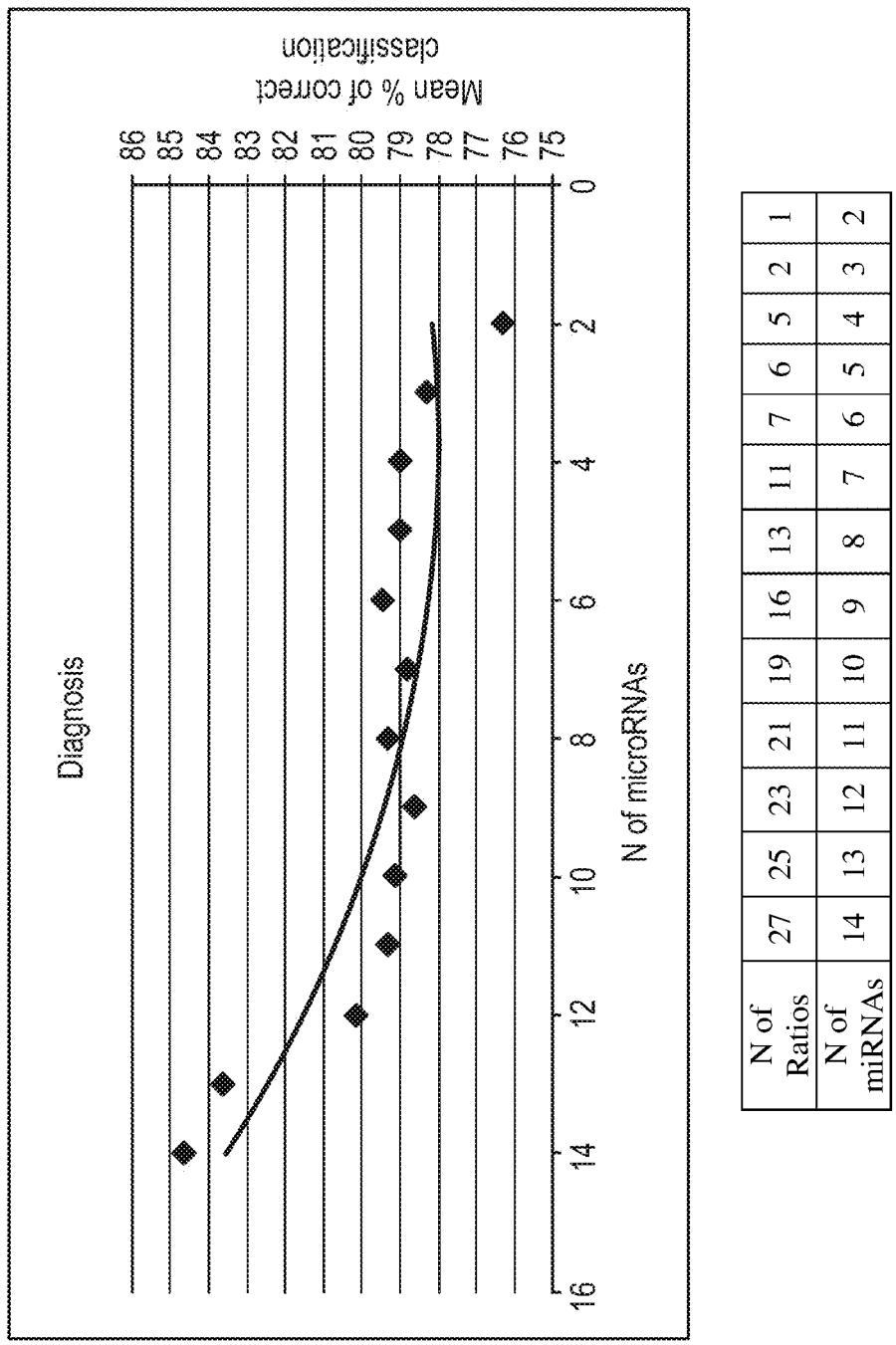

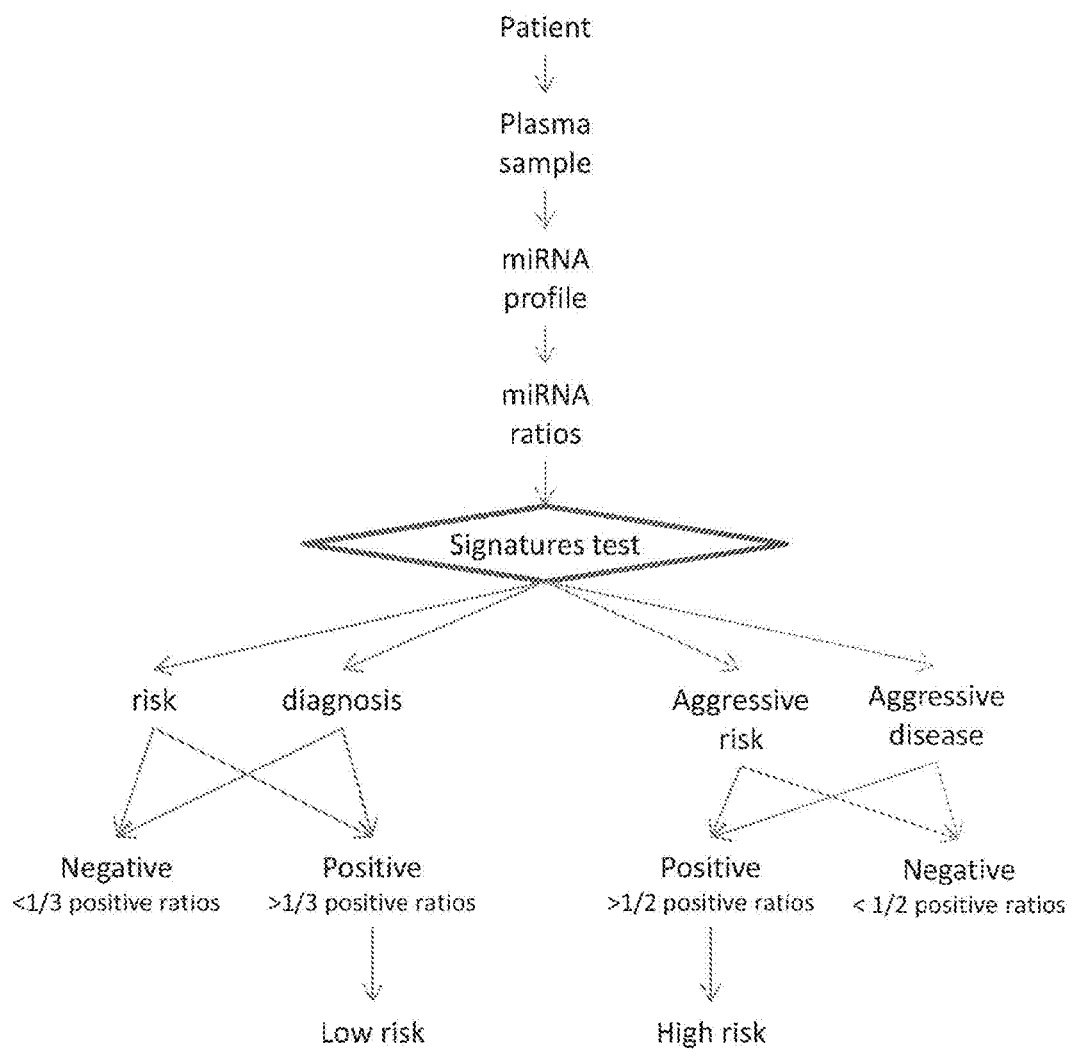

MICRO-RNA BIOMARKERS AND METHODS OF USING SAME

CROSS-REFERENCE TO RELATED APPLICATIONS

This application is a continuation application of application Ser. No. 13/367,582, filed Feb. 7, 2012, which claims the benefit of Italian Patent Application Nos. MI2011A000172, MI2011A000173 and MI2011A000174, each filed Feb. 7, 2011 and U.S. Provisional Application No. 61/522,328, filed Aug. 11, 2011. The contents of each of these applications are incorporated herein by reference in their entirety.

INCORPORATION-BY-REFERENCE OF SEQUENCE LISTING

The contents of the text file named "42823_501001US_ST25.txt", which was created on Apr. 23, 2012 and is 22 KB in size, are hereby incorporated by reference in their entirety.

FIELD OF THE INVENTION

The present invention concerns methods for identifying and using, in pre-diagnostic and/or diagnostic stages, special molecular bio-markers identifiable in biological samples, such as for example whole blood, serum, plasma, saliva or bronchia condensate collected from an individual.

In more detail, the invention relates to methods for identifying individuals at risk of tumour, in particular pulmonary tumour. The invention also concerns methods for determining a presence and/or level of aggressiveness of a tumour, for example a pulmonary tumour, in an individual.

The invention also relates to diagnostic kits and apparatus usable for setting up one or more stages of the methods.

Further, the invention concerns methods and pharmaceutical compounds for treating an individual in whom presence of a tumour has been diagnosed, for example a pulmonary tumour.

The invention also concerns methods and pharmaceutical compounds for treating an individual in whom a risk of developing a tumour has been identified, for example a pulmonary tumour, for reducing and/or eliminating the risk of developing a tumour.

BACKGROUND OF THE INVENTION

As is known, tumours are one of the main causes of death in the world. In particular, pulmonary tumours are the highest in terms of incidence, as they represent about 12% of all the new cases of cancer, and constitute the main cause of death by cancer in the world, in both men and women.

In Europe about 400,000 new cases are diagnosed per year (80% men, 20% women). In Italy the epidemiology of pulmonary cancer is similar, with an incidence of 34,000 cases per year of which 7,000 are women and 27,000 men.

Sadly the incidence and the mortality are very similar due to the highly lethal nature of pulmonary tumour: world-wide mortality 27,500, of which 22,000 mend and 5,500 women. This epidemiological data and the scarce level of treatability of the illness underline the importance of identifying methods which are able to identify as soon as possible any subjects who might be at risk of developing pulmonary cancer. Further, it is of great interest to develop procedures which can help in the correct diagnosis of tumours, in particular pulmonary tumours present in an individual subject under examination.

Notwithstanding these needs, tumour markers available today are for diagnostic use, i.e. they identify the patients when the disease has already developed such as to be identifiable with imaging methods (spiral CT scan). These markers are however few and not specific and essentially comprise biochemical markers such as the evaluation of the protein CEA (Carcinoembryonic Antigene) and some cytokeratins such as TPA, TPS and Cyfra 21.1.

Also known is a proteomic test (5-protein profile) on the serum, at present proposed by Vermillion Inc. and used to indicate a probability (score from 1 to 10) that ovarian masses might be of a malignant nature. This test is used for women who already present ovarian masses of a non-defined nature.

With specific reference to pulmonary tumours, although in recent years important improvements have been made in the treatment of oncological patients, there is however a need to develop more effective methods which can lead to a faster therapeutic intervention in clinical management of many types of tumours.

At present the majority of pulmonary tumours are diagnosed at a late stage, when the symptoms are clinically evident and, for example with reference to Non-small-cell lung carcinoma (NSCLC), only a third of patients with NSCLC exhibits a surgically-resectable disease, an approach which remains the most effective treatment for this type of tumour.

Notwithstanding recent progress in treatment of pulmonary cancer after resection and the use of specific treatments for determined molecular targets, the rate of healing of non-small-cell lung carcinoma (NSCLC) remains low due to the reappearance thereof in patients that are resistant to drugs or who present metastasis.

The effectiveness of the spiral CT scan in identification of pulmonary cancer in heavy smokers is under evaluation in various randomized clinical studies in Europe and the United States. Owing to the its high level of sensitivity there remain various critical points for its use in modern clinical practice, such as over-diagnosis of indolent nodules, with a consequently high frequency of non-necessary treatments and the verification of the effective impact on mortality.

In this context, in recent years microRNAs have been identified (herein below also MiRNA) as a new class of circulating bio-markers which by their nature seem to be very stable and highly specific tissue (Chen X, *Cell Res,* 2008). MiRNAs are small non-coding RNA molecules (length 19-25 nucleotides) having a regulatory function which are able to modulate the expression of several target genes involved in various molecular mechanisms, among which those involved in transformation processes.

The development of high-throughput technologies has enabled the study of overall expression of the profiles of miRNA in cancer (microRNAome) (Cummins J M et al., *Proc Natl Acad Sci USA,* 2006), revealing that there exist hundreds of miRNA whose expression is deregulated in tumours (Croce C M, Visone R, *AJP,* 2009; WO2009/070653, The Ohio State University Research Foundation).

Apart from the tissue specificity, miRNA possess a high degree of stability, ease of detection and association with known clinical-pathological parameters (Lu J et al., *Nature,* 2005).

Tests have also been carried out to determine whether miRNAs are stable, detectable and quantifiable not only in the tissues (both deep-frozen and fixed in formalin or paraffin) but also in the bodily fluids. The results of this research have demonstrated that miRNAs are also present in the blood circulation (whole blood, serum and plasma), where they are found in stable form protected by endogenous RNAsi. Circulating miRNAs are detectable and quantifiable and the studies which have taken their levels in oncological patients' biological fluids under examination have reported that some of them present deregulated levels with respect to healthy individuals (Heneghan H M et al., *Ann Surg,* 2010; Mitchell P S et al., *Proc Natl Acad Sci USA,* 2008; Chen X, *Cell Res,* 2008).

Recent publications report the profile of miRNAs circulating in the serum and plasma of patients having pulmonary tumour (Hu Z, *Clin Oncol,* 2010; Silva J, *Eur Respir J,* 2010 Shen J, *Lab Invest,* 2010).

Notwithstanding the presence of diagnostic imaging systems and the studies relating to microRNAs, there is still the need to identify procedures which are able to identify, with a certain degree of anticipation, individuals at risk of developing pulmonary cancer and possibly able to predict the development of the forms of cancer, in particular pulmonary tumour, that are more aggressive and lethal. There is also a need to improve the degree of reliability of diagnostic techniques at present available.

SUMMARY OF THE INVENTION

In this situation, the aim of the present invention is to obviate one or more of the limitations in the known procedures and products.

Thus it is an aim of the invention to provide procedures for early determination of individuals who present a risk of developing a tumour, in particular a pulmonary tumour.

A further aim of the invention is to make available procedures which assist in the diagnosis of tumour, in particular pulmonary tumours, in human subjects.

A further aim of the invention is to make available procedures which can be easily set up in laboratories, by analyzing biological samples collected from an individual.

A further aim of the invention is to provide procedures which enable satisfactory results to be obtained using samples of blood, serum or plasma.

A further aim of the invention is to define diagnostic kits and/or apparatus usable in the above-cited procedures in order to identify human subjects who are at risk of contracting a tumour and/or for assisting in the diagnosis of tumours present in human subjects.

A further aim of the invention is to provide pharmaceutical compounds and/or treatments which can be used to treat an individual in whom the presence of a pulmonary tumour has been diagnosed.

A final aim of the invention is to provide pharmaceutical compounds and/or treatments for reducing and/or eliminating the risk of developing a pulmonary tumour.

One or more of the set aims are substantially attained by a method and/or a kit and/or a compound and/or an apparatus in accordance with one or more of the accompanying claims.

Aspects of the invention are described herein below.

A first aspect concerns a procedure for identifying individuals at risk of a pulmonary tumour, the procedure comprising steps of: measuring, in at least a sample of biological fluid previously collected from a subject, a value of the level of expression of a plurality of microRNA molecules; determining when the measured values of the level of expression deviate with respect to a predetermined and respective control criterion.

The microRNA or miRNA molecules are thus used for identifying individuals at risk or in a stage in which the tumour has not yet manifested.

In a second aspect in accordance with the first aspect the step of determining comprises determining the level of expression of at least six miRNA from the miRNA listed in Tables Ia, Ic, IIa or IIc in a biological sample from a subject, and comparing the level of expression of said miRNA from said sample from said subject to the level of expression of said miRNA from a control biological sample. For example determining may comprise determining-in a biological sample from a subject-the level of expression of the six miRNA listed in Table Ib or Id or the level of expression of the six miRNA listed in Table IIb or IId, and comparing the level of expression of said six miRNA from said sample from said subject to the level of expression of said miRNA from a control biological sample, wherein a change or deviation in the level of expression of said at least six miRNA in said biological sample from said control biological sample identifies a subject at risk of manifesting a tumor (Table Ib or Id miRNA are used) or an aggressive tumor (Table IIb or IId miRNA are used).

In a third aspect in accordance with the first aspect the step of determining comprises substeps of calculating a plurality of ratios or real differences determined by performing the ratio or respectively the difference between the measured values of the levels of expression of a predetermined number of pairs of the microRNA molecules, comparing each of the real ratios or differences with a respective control value, determining the real ratios or differences which deviate from the respective ratio value or control difference.

In a fourth aspect in accordance with the third aspect, a step is also included of determining a number or percentage of real ratios or differences which deviate from the respective control value and defining as an individual at risk an individual for whom at least a predetermined number or a predetermined percentage of the real ratios or differences deviates with respect to the respective ratio value or control difference.

In a fifth aspect, in accordance with any one of the preceding aspects, for each of the calculated ratios, a respective control ratio is associated represented by the ratio of the expression values for the microRNAs in a control sample relating to a biological fluid of the same type. The control ratio is in reality either a known value, or a determined value as a mean of measured values in a sufficiently large population of individuals, or a value relating to a fluid sample collected from a healthy individual.

In a sixth aspect, in accordance with any one of the preceding aspects, the procedure comprises the step of correlating the deviation of a predetermined number or a predetermined percentage of expression levels (i.e. real ratios or differences) with respect to the corresponding control criteria in the presence or absence of risk that the individual clinically presents a pulmonary tumour in a predetermined time.

In a seventh aspect according to the preceding aspect the predetermined time is comprised between one and three years, more optionally is comprised between 12 and 28 months. In other words the method of the invention is able to significantly anticipate the determination of the risk of contracting a tumour with respect to traditional techniques (such as spiral CT) which have to wait for the disease to manifest at the level of lacerations or nodules of various mm.

In an eighth aspect in accordance with any one of the preceding aspects the procedure comprises a step of correlating the deviation of a predetermined number or a predetermined percentage of expression level with respect to the corresponding control criteria to the presence or absence of risk which the individual manifests clinically an aggressive pulmonary tumour in a predetermined time.

In a ninth aspect, according to the preceding aspect, the predetermined time is comprised between one and three years, more optionally between 12 and 28 months. In other words the method of the invention is able to significantly anticipate the determination of the risk of contracting an aggressive tumour with respect to the traditional techniques (such as spiral CT) which have to wait for the disease to manifest at the level of lacerations or nodules or various mm.

In a tenth aspect, in accordance with any one of the preceding aspects, calculating the plurality of real ratios or differences comprises using the expression values of a predetermined number or a predetermined percentage of the miRNAs of Table Ia, Ic, IIa and/or of Table IIc, optionally using the expression values of the miRNAs of Table Ib, Id, IIb and/or of Table IId.

In an eleventh aspect in accordance with any one of aspects $6^{th}$, $7^{th}$ or $10^{th}$, calculating the plurality of real ratios or differences comprises using the expression values of a predetermined number or a predetermined percentage of the miRNAs of Table Ia or Ic.

In a twelfth aspect, according to any one of aspects $8^{th}$, $9^{th}$ or $10^{th}$, calculating the plurality of real ratios or differences comprises using the expression values of a predetermined number or a predetermined percentage of the miRNA of Table IIa or IIc.

In a thirteenth aspect according to any one of the preceding aspects, calculating the plurality of real ratios comprises determining a predetermined number or a predetermined percentage of ratios among the values of the expression levels, the ratios being selected from the group comprising ratios between values of expression levels of pairs of microRNA as in Table IIIa or IIIc, optionally in which at least 20% are determined, more optionally at least 50% and still more optionally all the ratios of Table IIIa or IIIc.

In a fourteenth aspect in accordance with the preceding claim, determining a predetermined number or a predetermined percentage of ratios comprises calculating at least 20% of the real ratios of Table IIIa or IIIc and in which it comprises a step of defining as an individual at risk of pulmonary tumour, optionally in a period comprised between one and three years from a collection of the sample of biological fluid, an individual for whom at least 30%, optionally at least 50% of the real ratios calculated deviates with respect to the respective control ratio value.

In a fifteenth aspect in accordance with any one of aspects 13 or 14, in which the ratios are those of Table IIIb or IIId.

In a sixteenth aspect in accordance with any one of the preceding aspects, calculating the plurality of real ratios comprises determining a predetermined number or a predetermined percentage of ratios among the values of the expression levels, the ratios being selected from the group comprising ratios between values of expression levels of pairs of microRNAs as in Table IVa or IVc, optionally in which at least 30% are determined, more optionally at least 50%, and still more optionally all the ratios of Table IVa or IVc.

In a seventeenth aspect according to the preceding aspect, determining a predetermined number or a predetermined percentage of ratios comprises calculating at least 30% of the real ratios as in Table IVa or IVc, and wherein the procedure comprises a step of defining as an individual at risk of aggressive pulmonary tumour, optionally in a period comprised between one and three years from collecting a sample of biological fluid, an individual for whom at least 50%, optionally at least 75% of the real ratios calculated deviates with respect to the respective control ratio value.

In an eighteenth aspect according to any one of aspects 16 or 17, the ratios are those of Table IVb or IVd.

In a nineteenth aspect of any one of the preceding aspects, the steps of the procedure are conducted in vitro.

In a twentieth aspect in accordance with any one of the preceding aspects, the biological fluid is one selected from a group comprising: whole blood, a fraction of blood, plasma, serum.

In a twenty-first aspect in accordance with any one of the preceding aspects the pulmonary tumour is one selected from the group comprising: small-cell lung cancer (SCLC), non small-cell lung cancer (NSCLC), pulmonary adenocarcinoma (ADC), bronchio-alveolar carcinoma (BAC), squamous-cell lung carcinoma (SCC), large-cell carcinoma (LC).

In a twenty-second aspect according to any one of the preceding aspects, the sample of biological fluid originates from a smoker individual who, at the moment of the collection of the sample, does not present a pulmonary tumour if subjected to imaging diagnostic methods, in particular the smoker individual not presenting nodules of dimensions of greater than 5 mm if subjected to a spiral CT scan.

A twenty-third aspect concerns a medical kit for determining biomolecular markers present in a sample of human biological fluid, the kit comprising a platform having a plurality of sites, each of which is destined to receive a respective discrete quantity of the sample of biological fluid, each of the sites comprising a reagent capable of bonding with at least a respective microRNA of Table Ia, Ic, IIa and/or Table IIc, optionally wherein each of the sites comprises a reagent capable of bonding with at least a respective microRNA of Table Ib, Id, IIb and/or Table IId.

In a twenty-fourth aspect in accordance with the preceding aspect, the reagent includes at least a reagent selected from among the group comprising: a polynucleotide comprising a nucleotide sequence of at least one of the microRNAs as in Table Ia, Ic, IIa and/or Table IIc, optionally as in Table Ib, Id, IIb and/or Table IId; a polynucleotide comprising a nucleotide sequence which is complementary to a sequence of at least one of the microRNAs as in Table Ia, Ic, IIa and/or Table IIc, optionally as in Table Ib, Id, IIb and/or Table IId; a molecular probe configured such as to recognize a sequence of at least one of the microRNAs as in Table Ia, Ic, IIa and/or Table IIc, optionally as in Table Ib, Id, IIb and/or Table IId.

A twenty-fifth aspect concerns a medical apparatus comprising: a unit defining a seating for receiving one or more of the kits of aspects $23^{rd}$ or $24^{th}$; means for determining a value of the level of expression of the microRNAs as in Table Ia, Ic, IIa and/or Table IIc; means for calculating the values of the real ratios from among the values of levels of expression of pairs of microRNAs, the ratios being selected from those in Table IIIa, IIIc, IVa and/or Table IVd, optionally those ratios of Table IIIb, IIId, IVb and/or those of Table IVd.

In a twenty-sixth aspect according to the preceding aspect, the means for determining the value of the expression level comprise one of the techniques selected from the group: Quantitative Real-time PCR, Microfluidic cards, Microarrays, RT-PCR, quantitative or semi-quantitative, Northern blot, Solution Hybridization, or Sequencing.

A twenty-eighth aspect comprises an in vitro procedure for identifying individuals at risk of tumour and/or for determining a presence of and/or an aggressiveness of a tumour in an individual, the process comprising steps of: measuring, in at least a sample of biological fluid previously collected from a subject, a value of a level of expression of a plurality of microRNA molecules; calculating a plurality of real ratios determined by calculating a ratio between the measured values of the levels of expression of a predetermined number of pairs of the microRNA molecules; comparing each of the real ratios with a respective control value.

In a twenty-ninth aspect in accordance with the twenty-eighth aspect, the process comprises determining a number or percentage of real ratios which deviate from the respective control value, defining, as an individual presenting a form of tumour, an individual for whom at least a predetermined number or a predetermined percentage of the real ratios deviates with respect to the respective control ratio value.

In a thirtieth aspect in accordance with the twenty-ninth, a respective control ratio is associated to each of the calculated ratios, represented by a ratio of the values of expression for the microRNAs in a control sample relative to a biological fluid of a same type.

In a thirty-first aspect, in accordance with the thirtieth or the twenty-ninth, calculating the plurality of real ratios comprises using the values of expression of a predetermined number of the miRNAs as in Table Ia, Ic, IIa and/or Table IIc and/or Table Va, Vc, VIa and/or Table VIc.

In a thirty-second aspect in accordance with any one of aspects from the $29^{th}$ to $31^{st}$, calculating the plurality of real ratios comprises determining a predetermined number or a predetermined percentage of ratios from among the values of the levels of expression, the ratios being selected from among the group comprising ratios as in Table IIIa, IIIc, IVa, and/or Table IVc and/or in Table VIIa, VIIc, VIIIa and/or in Table VIIIc.

In a thirty-third aspect in accordance with the thirty-second, determining a predetermined number or a predetermined percentage of ratios comprises calculating at least 20% of the real ratios of Table VIIa or VIIc and comprises a step of defining as an individual presenting a pulmonary tumour an individual for whom at least 30% of the predetermined number of real ratios as in Table VIIa or VIIc which have been calculated deviate with respect to the control value.

In a thirty-fourth aspect in accordance with the thirty-third or the thirty-second, determining a predetermined number or a predetermined percentage of ratios comprises calculating at least 20% of the real ratios of Table VIIIa or VIIIc and comprises a step of defining as an individual presenting an aggressive pulmonary tumour an individual in whom 50%, optionally at least 60%, of the real ratios which have been calculated deviate with respect to the respective control value.

In a thirty-fifth aspect, in accordance with the thirty-fourth or the thirty-third or the thirty-second, determining the predetermined number or a predetermined percentage of ratios comprises calculating at least 20% of the real ratios of Table IIIa or IIIc and comprises a step of defining as an individual at risk of a pulmonary tumour, optionally in a period comprised between one and three years from a collection of the sample of biological fluid, an individual for whom at least 30%, optionally at least 50%, of the real ratios calculated deviate with respect to the respective control ratio value.

In a thirty-sixth aspect in accordance with the thirty-fifth, the thirty-fourth or the thirty-third or the thirty-second, determining the predetermined number or a predetermined percentage of ratios comprises calculating at least 30% of the real ratios of Table IVa or IVc and comprises a step of defining as an individual at risk of an aggressive pulmonary tumour, optionally in a period comprised between one and three years from a collection of the sample of biological fluid, an individual for whom at least 50%, optionally at least 75%, of the real ratios calculated deviate with respect to the respective control ratio value.

In a thirty-seventh aspect in accordance with the any one of the aspects from the $28^{th}$ to the $32^{nd}$, determining a predetermined number or a predetermined percentage of ratios comprises calculating the real ratios of Table VIIb or VIId and wherein the procedure comprises a step of defining as an individual presenting a pulmonary tumor an individual for whom at least 80% of the real ratios as in Table VIIb or VIId which have been calculated deviate with respect to the control value.

In a thirty-eighth aspect in accordance with the any one of the aspects from the $28^{th}$ to the $32^{nd}$, determining a predetermined number or a predetermined percentage of ratios comprises calculating the real ratios of Table VIIIb or VIIId and wherein the procedure comprises a step of defining as an individual presenting an aggressive pulmonary tumor an individual for whom at least 80% of the real ratios as in Table VIIIb or VIIId which have been calculated deviate with respect to the control value.

In a thirty-ninth aspect in accordance with the any one of the aspects from the $28^{th}$ to the $32^{nd}$, determining a predetermined number or a predetermined percentage of ratios comprises calculating the real ratios of Table IIIb or IIId and wherein the procedure comprises a step of defining as individual at risk of a pulmonary tumour, optionally in a period comprised between one and three years from a collection of the sample of biological fluid, an individual for whom at least 80% of the real ratios as in Table IIIb or IIId which have been calculated deviate with respect to the control value.

In a fortieth aspect in accordance with the any one of the aspects from the $28^{th}$ to the $32^{nd}$, determining a predetermined number or a predetermined percentage of ratios comprises calculating the real ratios of Table IVb or IVd and wherein the procedure comprises a step of defining as individual at risk of an aggressive pulmonary tumour, optionally in a period comprised between one and three years from a collection of the sample of biological fluid, an individual for whom at least 80% of the real ratios as in Table IVb or IVd which have been calculated deviate with respect to the control value.

In a forty-first aspect in accordance with any one of the preceding aspects from the $28^{th}$ to $40^{th}$, the biological fluid is one selected from among a group comprising: whole blood, a fraction of blood, plasma, serum; saliva or bronchial condensate.

In a forty-second aspect in accordance with any one of the preceding aspects from the $28^{th}$ to $41^{st}$, the tumour is a pulmonary tumour selected from among a group comprising: small-cell lung cancer (SCLC), non small-cell lung cancer (NSCLC), pulmonary adenocarcinoma (ADC), bronchio-alveolar carcinoma (BAC), squamous-cell lung carcinoma (SCC), large-cell carcinoma (LC).

In a forty-third aspect, in accordance with any one of the preceding aspects from the $28^{th}$ to $42^{nd}$, the sample of biological fluid originates from a smoker individual who, at the moment of the collection of the sample, presents a pulmonary tumour if subjected to imaging diagnostic methods, in particular the smoker individual presenting nodules of dimensions of greater than 5 mm if subjected to a spiral CT scan.

In a forty-fourth aspect, a medical kit is provided for determining bio-molecular markers present in a sample of human biological fluid, the kit comprising: a platform, for example a support for receiving fluid samples, having a plurality of sites, each of which is destined to receive a respective discrete quantity of the sample of biological fluid, each of the sites comprising a reagent capable of bonding with at least a respective microRNA of Table Ia, Ic, IIa and/or Table IIc and/or Table Va, Vc, VIa and/or Table VIc, optionally a reagent capable of bonding with at least a respective microRNA as in Table Ib, Id, IIb and/or Table IId, and/or Table Vb, Vd, VIb and/or Table VId.

In a forty-fifth aspect in accordance with the preceding aspect, the reagent includes at least a reagent selected from among a group comprising:

a polynucleotide comprising a nucleotide sequence of at least one of the microRNAs as in Table Ia, Ic, IIa and/or Table IIc and/or Table Va, Vc, VIa and/or Table VIc, or a nucleotide sequence of at least one of the microRNAs as in Table Ib, Id, IIb and/or Table IId, and/or Table Vb, Vd, VIb and/or Table VId;

a polynucleotide comprising a nucleotide sequence which is complementary to a sequence of at least one of the microRNAs as in Table Ia, Ic, IIa and/or Table IIc and/or Table Va, Vc, VIa and/or Table VIc, optionally comprising a nucleotide sequence which is complementary to a sequence of at least one of the microRNAs as in Table Ib, Id, IIb and/or Table IId, and/or Table Vb, Vd, VIb and/or Table VId;

a molecular probe configured such as to recognize a sequence of at least one of the microRNAs as in Table Ia, Ic, IIa and/or Table IIc and/or Table Va, Vc, VIa and/or Table VIc, optionally a sequence of at least one of the microRNAs as in Table Ib, Id, IIb and/or Table IId, and/or Table Vb, Vd, VIb and/or Table VId.

In a forty-sixth aspect a medical apparatus is provided, comprising: a unit defining a seating for receiving one or more of the kits of the preceding claim, means for determining a value of the level of expression of the microRNAs as in Tables Ia, Ic, IIa and/or Table IIc and/or Table Va, Vc, VIa and/or Table VIc, optionally the value of the level of expression of the microRNA as in Tables Ib, Id, IIb and/or Table IId, and/or Table Vb, Vd, VIb and/or Table VId; means for calculating the values of the real ratios from among the values of levels of expression of pairs of microRNAs, the ratios being selected from those in Tables IIIa, IIIc, IVa and/or Table IVc and/or Table VIIa, VIIc, VIIIa and/or Table VIIIc, optionally from those in Tables IIIb, IIId, IVb and/or Table IVd and/or Table VIIb, VIId, VIIIb and/or Table VIIId.

In a forty-third aspect in accordance with the preceding aspect, the means for determining the value of the level of expression comprise one from among the techniques selected from a group as follows: Quantitative Real-time PCR, Microfluidic cards, Microarrays, RT-PCR, quantitative or semi-quantitative, Northern blot, Solution Hybridization, or Sequencing.

In a forty-eighth aspect a method is comprised for treating an individual in whom a presence of a pulmonary tumour has been diagnosed or in whom a risk of developing a pulmonary tumour has been identified, respectively for treatment of the pulmonary tumour or for reducing and/or eliminating the risk of developing a pulmonary tumour, the method comprising following steps: measuring a level of expression of at least an miRNA listed in Table Ia, Ic, IIa and/or Table IIc and/or Table Va, Vc, VIa and/or Table VIc present in a sample of biological fluid previously taken from the individual, determining the miRNAs having measured values of a level of expression which deviate with respect to a predetermined and respective control criterion; altering the level of expression of the miRNAs for which the levels of expression deviate with respect to the respective control criterion.

In a forty-ninth aspect the step of measuring comprises measuring a level of expression of at least a miRNA listed in Table Ib, Id, IIb and/or Table IId, and/or Table Vb, Vd, VIb and/or Table VId present in a sample of biological fluid previously taken from the individual.

In a fiftieth aspect in accordance with the preceding aspect the step of altering the level of expression of the miRNAs comprises: administering to the individual an effective quantity of at least one of the miRNAs listed in Table Ia, Ic, IIa and/or Table IIc and/or Table Va, Vc, VIa and/or Table VIc, or of one or more of the miRNA listed in Table Ib, Id, IIb and/or Table IId, and/or Table Vb, Vd, VIb and/or Table VId, if the level of expression measured of the miRNA or the miRNAs is lower than a respective control level of expression In a fifty-first aspect according to the 49th or 50th aspect, the step of altering the level of expression of the miRNAs comprises administering to the individual an effective quantity of at least a compound for inhibiting the expression of at least one of the miRNAs listed in Table Ia, Ic, IIa and/or Table IIc and/or Table Va, Vc, VIa and/or Table VIc, or listed in Table Ib, Id, IIb and/or Table IId, and/or Table Vb, Vd, VIb and/or Table VId, if the measured level of expression of one or more of the miRNA or miRNAs is higher than the control level of expression.

In a fifty-second aspect, in accordance with the $50^{th}$ aspect, the method comprises restoring the values of levels of expression to a control level of expression for the miRNAs which are under-expressed with respect to the respective control level of expression.

In a fifty-third aspect in accordance with any one of aspects from the $48^{th}$ to the $52^{nd}$, the method comprises administering a therapeutically effective quantity of a compound comprising at least one of the miRNAs of Table Ia, Ic, IIa and/or Table IIc and/or Table Va, Vc, VIa and/or Table VIc, optionally at least one of the miRNA listed in Table Ib, Id, IIb and/or Table IId, and/or Table Vb, Vd, VIb and/or Table VId, chemically synthesized (miRNA mimetics) or recombinant.

In a fifty-fourth aspect according to any one of aspects from $51^{st}$ to $53^{rd}$, the method comprises reducing the values of the level of expression to the control level of expression for miRNAs which are over-expressed with respect to the respective control level of expression.

In a fifty-fifth aspect in accordance with any one of the aspects from $48^{th}$ to $54^{th}$, the method comprises administering a therapeutically effective quantity of a compound comprising at least an inhibitor of a microRNA of Table Ia, Ic, IIa and/or Table IIc and/or Table Va, Vc, VIa and/or Table VIc or Table Ib, Id, IIb and/or Table IId, and/or Table Vb, Vd, VIb and/or Table VId.

In fifty-sixth aspect in accordance with the preceding aspect, the inhibitor comprises double-filament RNA.

In a fifty-seventh aspect according to the preceding aspect the method comprises short interfering RNA (siRNA), antisense nucleic acids (anti-miRNA oligonucleotides (AMOs), molecules of enzymatic RNA (ribozymes).

In a fifty-eight aspect according to any one of aspects from the 55$^{th}$ to the 57$^{th}$, the inhibitor is directed to a specific product of microRNA and interferes with the expression, for example by means of inhibition of a translation or induction of degradation, of a target gene of the microRNA.

In a fifty-ninth aspect in accordance with any one of the preceding aspects, the step of determining the miRNAs having measured values of the levels of expression which deviate with respect to the respective control criterion comprises: calculating a plurality of real ratios determined by performing a ratio between the measured values of the levels of expression of a predetermined number of pairs of the microRNA molecules, the ratios being selected from a group comprising the ratios as in Table IIIa, IIIc, IVa and/or Table IVc and/or Table VIIa, VIII, VIIIa and/or Table VIIIc, optionally the ratios being selected from a group comprising the ratios as in and/or Table IIIb, IIId, IVb and/or Table IVd and/or Table VIIb, VIId, VIIIb and/or Table VIIId, determining the real ratios which deviate from the respective control values, identifying the miRNAs involved in the real ratios which deviate from the respective control value.

A sixtieth aspect concerns a pharmaceutical compound for treating an individual in whom has been diagnosed a pulmonary tumour or in whom a risk of developing a pulmonary tumour has been identified, respectively for treatment of the pulmonary tumour or for reducing and/or eliminating the risk of developing a pulmonary tumour, the compound comprising: at least one, optionally at least six, of the miRNAs listed in Table Ia, Ic, IIa and/or Table IIc and/or Table Va, Vc, VIa and/or Table VIc, and/or at least an inhibitor of the expression of at least one, optionally at least six, of the miRNAs listed in Table Ia, Ic, IIa and/or Table IIc and/or Table Va, Vc, VIa and/or Table VIc.

In a sixty-first aspect, according to the preceding aspect, the compound comprises a therapeutically effective quantity of at least one of the miRNAs listed in Table Ia, Ic, IIa and/or Table IIc and/or Table Va, Vc, VIa and/or Table VIc.

A sixty-second aspect concerns a pharmaceutical compound for treating an individual in whom has been diagnosed a pulmonary tumour or in whom a risk of developing a pulmonary tumour has been identified, respectively for treatment of the pulmonary tumour or for reducing and/or eliminating the risk of developing a pulmonary tumour, the compound comprising: at least one, optionally at least six, of the miRNAs listed in Table Ib, Id, IIb and/or Table IId, and/or Table Vb, Vd, VIb and/or Table VId, and/or at least an inhibitor of the expression of at least one, optionally of at least six, of the miRNAs listed in Table Ib, Id, IIb and/or Table IId, and/or Table Vb, Vd, VIb and/or Table VId.

In a sixty-third aspect, according to the preceding aspect, the compound comprises a therapeutically effective quantity of at least one, optionally of at least six, of the miRNAs listed in Table Ib, Id, IIb and/or Table IId, and/or Table Vb, Vd, VIb and/or Table VId.

In a sixty-fourth aspect in accordance with any one of aspects from the 60$^{th}$ to the 63$^{rd}$, the quantity is able, for the miRNAs that are under-expressed with respect to the respective control level of expression, to restore the values of the level of expression to the respective control level of expression.

In a sixty-fifth aspect in accordance with any one of aspects from the 60$^{th}$ to the 64$^{th}$, the therapeutically effective quantity comprises miRNA of Table Ia, Ic, IIa and/or Table IIc and/or Table Va, Vc, VIa and/or Table VIc, optionally the therapeutically effective quantity comprises the miRNA of Table Ib, Id, IIb and/or Table IId, and/or Table Vb, Vd, VIb and/or Table VId, chemically synthesized or recombinant.

In a sixty-sixth aspect in accordance with any one of aspects from the 60$^{th}$ to the 64$^{th}$, the compound comprises a therapeutically effective quantity of the inhibitor of the expression of at least one of the miRNAs listed in Table Ia, Ic, IIa and/or Table IIc and/or Table Va, Vc, VIa and/or Table VIc, optionally all those listed in Table Ib, Id, IIb and/or Table IId, and/or Table Vb, Vd, VIb and/or Table VId, the quantity being able, for the over-expressed miRNAs with respect to the respective control level of expression, to reduce the values of the level of expression to the respective control level of expression.

In a sixty-seventh aspect in accordance with the preceding aspect, the inhibitor comprises double-filament RNA, optionally short interfering RNA (siRNA), and/or antisense nucleic acids, and/or enzymatic RNA molecules (ribozymes).

In a sixty-eighth aspect in accordance with one of the preceding two aspects, the inhibitor is directed to a specific product of microRNA and interferes with the expression (by means of inhibition of translation or induction of degradation) of a target gene of the microRNA.

In a sixty-ninth aspect, a pharmaceutical compound is provided according to any one of claims from the 60$^{th}$ to the 68$^{th}$, for preparation of a medicament usable in one of the therapeutic methods of any one of aspects from the 48$^{th}$ to 59$^{th}$.

In a seventieth aspect in accordance with the preceding aspect the therapeutic method is a method for treating an individual in whom a presence of a pulmonary tumour has been diagnosed.

In a seventy-first aspect in accordance with the sixty-ninth, the therapeutic method is a method for treating an individual in whom a risk of developing a pulmonary tumour has been identified, in order to reduce and/or eliminate the risk of developing the pulmonary tumour.

In a seventy-second aspect, in accordance with any one of the preceding aspects, as a variant of the invention and alternatively to the real ratios (in the method, the medical kit and the apparatus) real differences are determined by performing the difference between the measured values of the expression levels of a predetermined number of pairs of the molecules of microRNA. In this case each of the differences is compared with a respective control value in order to determine the differences which deviate from the respective control value.

All the preceding aspects are equally applied by replacing the real ratios with real differences between the pairs of miRNA as in the appended tables.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the claimed invention. In the case of conflict, the present specification, including definitions, will control. In addition, the materials, methods, and examples are illustrative only and are not intended to be limiting.

Other features and advantages of the invention will be apparent from the following detailed description and claims.

BRIEF DESCRIPTION OF THE DRAWINGS

FIG. 1 is a schematic showing the clinical-pathological characteristics of patients from training and validation sets selected for miRNA expression analysis in plasma samples.

FIG. 5 is two graphs showing the risk of manifesting a pulmonary tumor (validation set). Left Panel shows the ROC curve when using the 15 miRNAs of Table I to create the 30 ratios of Table III. Right Panel shows the ROC curve when using the 6 miRNAs of Table Ib to create the 9 ratios of Table IIIb.

FIG. 6 is two graphs showing the risk of manifesting an aggressive pulmonary tumor (validation set). Left panel shows the ROC curve when using the 16 miRNAs of Table II to create the 28 ratios of Table IV. Right panel shows the ROC curve when using the 6 miRNAs of Table IIb to create the 9 ratios of Table IVb.

FIG. 7 is two graphs showing the risk of manifesting an aggressive pulmonary tumor (validation set). Left panel shows the ROC curve when using the 18 miRNAs of Table V to create the 36 ratios of Table VII. Right panel shows the ROC curve when using the 6 miRNAs of Table Vb to create the 9 ratios of Table VIIb.

FIG. 8 is two graphs showing the risk of manifesting an aggressive pulmonary tumor (validation set). Left panel shows the ROC curve when using the 10 miRNAs of Table VI to create the 16 ratios of Table VIII. Right panel shows the ROC curve when using the 6 miRNAs of Table VIb to create the 9 ratios of Table VIIIb.

FIG. 12A shows data arranged according to the extent of disease: 92% for stage I (95% CI: 70.0-97.8) and 7% for stage II-IV (95% CI: 0.5-27.5, P<0.001). FIG. 12B shows data arranged according to the year of CT-detection: 77% for lung cancers detected in the first 2 y of the study (95% CI: 53.7-89.8) and 36% for lung cancers diagnosed from third to fifth years (95% CI: 13.7-58.7, P=0.005).

FIGS. 15A, 15B, and 15C are graphs showing consistency of miRNA expression measurement in plasma samples by quantitative real-time PCR considering only the 100 miRNAs selected for class comparison analysis. FIG. 15A shows that technical duplicates were performed for two patient samples (341 and 380) and for a control pool (M2). The graphical representation was performed plotting the first miRNA values obtained on abscissa (duplicate A) and the values obtained in the second evaluation in ordinate (duplicate B). The linear regression value shows a good reproducibility of measurements. FIG. 15B shows the correlation between two different control pools. FIG. 15C is a graphical representation of average values of all Pearson correlation coefficients between control pools, technical duplicates, and between all patient samples (before and at time of disease).

FIG. 16A is graph showing the number of miRNA and ratio of miRNA for a signature of risk. FIG. 16C is graph showing the number of miRNA and ratio of miRNA for a signature of diagnosis.

FIG. 17 is a flow-chart illustrating the use of miRNA and the ratio of miRNA from a patient in the signatures of risk, aggressive risk, diagnosis and aggressive disease.

DETAILED DESCRIPTION OF THE INVENTION

Figure 2:
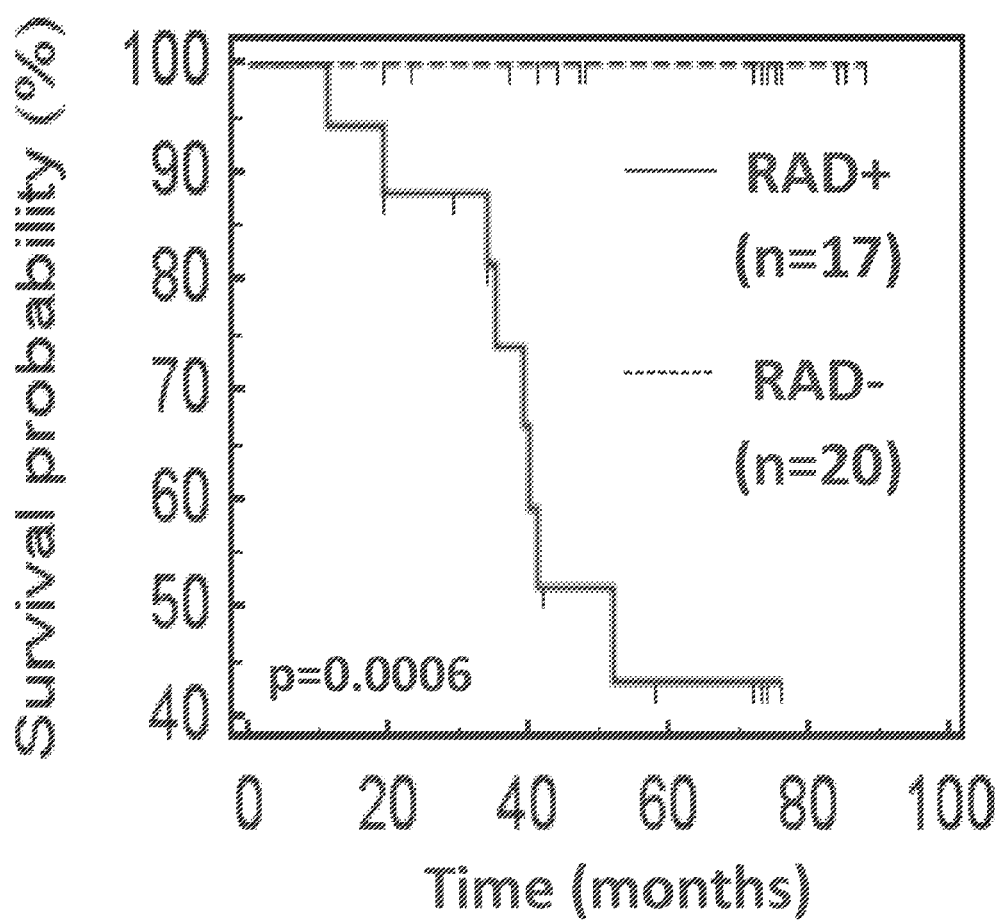
FIG. 2 is a graph showing a Kaplan-Meier survival curve of patients with or without the signature of risk of aggressive disease.

The present invention provides methods comprising determining the level of expression of at least two miRNA, or at least six miRNA, from the miRNA listed in Tables Ia, Ic, IIa, IIc, Va, Vc, VIa, or VIc in a biological sample from a subject, and comparing the level of expression of said miRNA from said sample from said subject to the level of expression of said miRNA from a control biological sample.

The present invention provides methods comprising determining the level of expression of at least two miRNA, or at least six miRNA, listed in Table Ib or Id in a biological sample from a subject, and comparing the level of expression of said miRNA from said sample from said subject to the level of expression of said miRNA from a control biological sample, wherein a change or deviation in the level of expression of said at least two miRNA in said biological sample from said control biological sample identifies a subject at risk of manifesting a tumor. Preferably, the miRNA can be the miRNA listed in Table Ie. Preferably, the tumor cannot be detected by CT spiral scan.

The present invention provides methods comprising determining the level of expression of at least two miRNA, or at least six miRNA, listed in Table IIb or IId in a biological sample from a subject, and comparing the level of expression of said miRNA from said sample from said subject to the level of expression of said miRNA from a control biological sample, wherein a change or deviation in the level of expression of said at least two miRNA in said biological sample from said control biological sample identifies a subject at risk of manifesting an aggressive tumor. Preferably, the miRNA can be the miRNA listed in Tables IIe, IIf or IIg.

The present invention provides methods comprising determining the level of expression of at least two miRNA, or at least six miRNA, listed in Table Vb or Vd in a biological sample from a subject, and comparing the level of expression of said miRNA from said sample from said subject to the level of expression of said miRNA from a control biological sample, wherein a change or deviation in the level of expression of said at least two miRNA in said biological sample from said control biological sample determines the presence of a tumor in said subject. Preferably, the miRNA can be the miRNA listed in Tables Ve or Vf. Preferably, the determination of the presence of said tumor confirms detection by CT spiral scan.

The present invention provides methods comprising determining the level of expression of at least two miRNA, or at least six miRNA, listed in Table VIb or VId in a biological sample from a subject, and comparing the level of expression of said miRNA from said sample from said subject to the level of expression of said miRNA from a control biological sample, wherein a change or deviation in the level of expression of said at least two miRNA in said biological sample from said control biological sample determines the presence of an aggressive tumor in said subject. Preferably, the miRNA can be the miRNA listed in Tables VIe or VIf. Preferably, the determination provides a prognosis of disease-free survival following surgical intervention.

The methods of the present invention can further comprise calculating a plurality of real quotients by determining a ratio between the level of expression of at least one pair of miRNA from at least two miRNA, or at least six miRNA, listed in Tables Ia, Ic, IIa, IIc, Va, Vc, VIa, or VIc; comparing each of the real quotients with a respective control value; and determining the real quotients which deviate from the respective control quotient value.

The methods of the present invention can further comprise calculating a plurality of real quotients by determining a ratio between the level of expression of at least one pair of miRNA from at least two miRNA, or at least six miRNA, listed in Tables Ib, Id, IIb, IId, Vb, Vd, VIb or VId; comparing each of the real quotients with a respective control value; and determining the real quotients which deviate from the respective control quotient value. Preferably, the miRNA can be the miRNA listed in Table Ie, IIe, IIf, IIg, Ve, Vf, VIe or VIf.

The methods of the present invention can further comprise determining a number or percentage of real quotients which deviate from the respective control value.

The methods of the present invention can further comprise defining as an individual at risk an individual for whom at least a predetermined number or a predetermined percentage of the real quotients deviates with respect to the respective control quotient value.

For each of the calculated quotients a respective control quotient is associated, represented by a ratio of the levels of expression for the miRNA in a control biological sample relative to a biological sample of a same type.

The methods of the present invention can further comprise correlating the deviation of a predetermined number or a predetermined percentage of levels of expression with respect to the corresponding control criteria to a presence or absence of risk that the individual might clinically present with a tumor in a predetermined time.

The individual might clinically present an aggressive tumor in a predetermined time. The predetermined time is between one and three years. Preferably, the predetermined time is within 28 months.

Calculating the plurality of real quotients comprises using the expression level of at least two miRNA, or at least six miRNA, listed in Tables Ia, Ic, IIa, IIc, Va, Vc, VIa, or VIc. Calculating the plurality of real quotients comprises determining a predetermined number or a predetermined percentage of quotients from among the levels of expression, wherein the quotients are selected from at least one of the quotients, at least two of the quotients, at least six of the quotients, as listed in Tables IIIa, IIIc, IVa, IVc, VIIa, VIIc, VIIIa, or VIIIc. At least 20%, 30%, 50% or 100% of the real quotients listed in Tables IIIa, IIIc, IVa, IVc, VIIa, VIIc, VIIIa, or VIIIc can be determined. The quotients can be selected from the quotients as listed in Tables IIIb, IIId, IVb, IVd, VIIb, VIId, VIIIb, or VIIId.

The methods of the present invention can further comprise defining as an individual at risk of a tumor, an individual for whom at least 20%, 30%, 50% or 100% of the real quotients calculated deviate with respect to the respective control quotient value. The individual is at risk of a tumor between one to three years from a collection of the biological sample. The tumor can be an aggressive tumor.

The methods of the present invention can further comprise defining as an individual presenting a tumor, an individual for whom at least 20%, 30%, 50%, 60% or 100% of the real quotients calculated deviate with respect to the respective control quotient value. The tumor can be an aggressive tumor.

The tumor is a pulmonary tumor. The pulmonary tumor can be small-cell lung cancer (SCLC), non small-cell lung cancer (NSCLC), pulmonary adenocarcinoma (ADC), bronchio-alveolar carcinoma (BAC), squamous-cell lung carcinoma (SCC) or large-cell carcinoma (LC).

The biological sample is a biological fluid. The biological fluid can be whole blood, a fraction of blood, plasma or serum. The biological sample originates from a smoker individual who, at the moment of the collection of the sample, does not present a pulmonary tumor if subjected to imaging diagnostic methods, in particular the smoker individual not presenting nodules of dimensions of greater than 5 mm if subjected to a spiral CT scan.

The control biological sample is a biological sample from a disease-free subject. The control biological sample is a biological sample obtained from said subject at a previous time. The control biological sample is obtained from said subject up to three years preceding diagnosis. The control biological sample is a biological sample obtained from a different tissue from said subject.

As used herein, an "individual", "subject", "patient" or "subject in need thereof" is an individual having an risk of developing a tumor or an aggressive tumor or one who may have or may be afflicted with a tumor or aggressive tumor. These terms may be utilized interchangeably. Preferably, the individual is a mammal. The mammal can be e.g., any mammal, e.g., a human, primate, bird, mouse, rat, fowl, dog, cat, cow, horse, goat, camel, sheep or a pig. Preferably, the mammal is a human.

As used herein, MicroRNA or miRNA is small, non-coding, RNA molecules (length 19-25 nucleotides). In particular, reference is made to miRNA present in biological samples of human tissue, for example whole blood, plasma, serum, saliva or bronchial condensate.

Signature of Risk

The present invention provides methods including: determining the level of expression of the six miRNA listed in Table Ib or Id in a biological sample from a subject, and comparing the level of expression of said miRNA from said sample from said subject to the level of expression of said miRNA from a control biological sample, wherein a change or deviation in the level of expression of said at least six miRNA in said biological sample from said control biological sample identifies a subject at risk of manifesting a tumor. Preferably, the tumor cannot be detected by CT spiral scan.

The method can further include: calculating a plurality of real quotients by determining a ratio between the level of expression of at least one pair of miRNA from at least six miRNA listed in Table Ib or Id; comparing each of the real quotients with a respective control value; and determining the real quotients which deviate from the respective control quotient value.

The present invention provides miRNAs, in particular those of appended Table Ia or Ic, as molecular biomarkers for the evaluation of the risk of manifesting pulmonary tumours within 1-3 years from the sample collection of biological fluid. The present invention also provides that the ratios among the miRNA expression values are ideal molecular biomarkers for investigation into the evaluation of the risk of contracting a pulmonary tumour within 1-3 years from the sample collection of biological fluid, such as whole blood, serum, plasma, saliva or bronchial condensate.

As used herein, an individual at risk of tumour (aggressive or not according to the case studies): an individual who in the time of reference (1-3 years) following the collection of the biological sample has a risk of over 80% of developing a tumour, for example a pulmonary tumour, detectable using techniques such as spiral CT.

Using the expression levels of the miRNAs listed in Table Ia or Ic, the ratios were identified among the values measured of the expression levels relative to the pairs of microRNA listed in Table IIIa or IIIc. These ratios can be used for the evaluation of the risk of contracting pulmonary tumour within 1-3 years from the collection of the sample of biological fluid, giving extremely reliable prediction results.

In more detail, by calculating a sufficient number of real ratios selected from among those in Table IIIa or IIIc, for example at least 20% of them, and optionally at least 50%, it is possible to observe the progress with respect to control ratios. An individual is defined at high risk of pulmonary tumour, which might be detectable by spiral CT, in a period comprised between one and three years from the collection of the sample of biological fluid, for whom at least 30% of real ratios calculated deviates with respect to the respective value of the control ratio.

TABLE Ia

One set of miRNAs used for evaluation of the risk
of manifesting a pulmonary tumour (within 1-3 years
from collecting the sample of biological fluid).
miRNA hsa-miR-451
hsa-miR-320

TABLE Ia-continued

One set of miRNAs used for evaluation of the risk
of manifesting a pulmonary tumour (within 1-3 years
from collecting the sample of biological fluid).
miRNA hsa-miR-660
hsa-miR-92a
hsa-miR-106a
hsa-miR-140-5p
hsa-miR-15b
hsa-miR-17
hsa-miR-197
hsa-miR-19b
hsa-miR-221
hsa-miR-28-3p
hsa-miR-30b
hsa-miR-30c
hsa-miR-145

Comparing the miRNAs listed in Table Ia in pre-disease patient samples v. disease free samples (control) results showed a sensitivity of 83.3 (training sensitivity of 85.0; validation sensitivity of 81.3) and a specificity of 95.5 (training specificity of 85.7; validation specificity of 100.0).

TABLE Ib

One set of preferred miRNAs used for evaluation of the
risk of manifesting a pulmonary tumour (within 1-3 years
from collecting the sample of biological fluid).
miRNA hsa-miR-451
hsa-miR-320
hsa-miR-660
hsa-miR-197
hsa-miR-30b
hsa-miR-30c Comparing the preferred miRNAs listed in Table Ib in pre-disease patient samples v. disease free samples (control) results showed a sensitivity of 80.6 (training sensitivity of 80.0; validation sensitivity of 81.3) and a specificity of 95.5 (training specificity of 85.7; validation specificity of 100.0).

TABLE Ic

Another set of miRNAs used for evaluation of the risk of
manifesting a pulmonary tumour (within 1-3 years from
collecting the sample of biological fluid).
miRNA hsa-miR-660
hsa-miR-451
hsa-miR-197
hsa-miR-17
hsa-miR-15b
hsa-miR-106a
hsa-miR-16
hsa-miR-92a
hsa-miR-19b
hsa-miR-101
hsa-miR-133a
hsa-miR-28-3p
hsa-miR-320
hsa-miR-126
hsa-miR-142-3p
hsa-miR-140-3p

TABLE Id

Another set of preferred miRNAs used for evaluation of the risk of manifesting a pulmonary tumour (within 1-3 years from collecting the sample of biological fluid).
miRNA hsa-miR-660
hsa-miR-451
hsa-miR-197
hsa-miR-17
hsa-miR-15b
hsa-miR-106a

TABLE Ie

Another set of preferred miRNAs used for evaluation of the risk of manifesting a pulmonary tumour (within 1-3 years from collecting the sample of biological fluid).
miRNA hsa-miR-660
hsa-miR-197

TABLE IIIa ratios among measured values of expression of pairs of miRNAs used for evaluating a risk of manifesting a pulmonary tumour (within 1-3 years from collecting the sample of biological fluid).
miRNA Pairs Q1 = hsa-miR-30c/hsa-miR-660
Q2 = hsa-miR-30b/hsa-miR-660
Q3 = hsa-miR-197/hsa-miR-660
Q4 = hsa-miR-17/hsa-miR-660
Q5 = hsa-miR-28-3p/hsa-miR-660
Q6 = hsa-miR-106a/hsa-miR-660
Q7 = hsa-miR-15b/hsa-miR-660
Q8 = hsa-miR-30c/hsa-miR-451
Q9 = hsa-miR-30b/hsa-miR-451
Q10 = hsa-miR-197/hsa-miR-451
Q11 = hsa-miR-145/hsa-miR-660
Q12 = hsa-miR-19b/hsa-miR-660
Q13 = hsa-miR-17/hsa-miR-451
Q14 = hsa-miR-28-3p/hsa-miR-451
Q15 = hsa-miR-106a/hsa-miR-451
Q16 = hsa-miR-30c/hsa-miR-320
Q17 = hsa-miR-30b/hsa-miR-320
Q18 = hsa-miR-197/hsa-miR-320
Q19 = hsa-miR-15b/hsa-miR-451
Q20 = hsa-miR-28-3p/hsa-miR-320
Q21 = hsa-miR-197/hsa-miR-92a
Q22 = hsa-miR-30b/hsa-miR-92a
Q23 = hsa-miR-30c/hsa-miR-92a
Q24 = hsa-miR-140-5p/hsa-miR-660
Q25 = hsa-miR-221/hsa-miR-660
Q26 = hsa-miR-19b/hsa-miR-451
Q27 = hsa-miR-145/hsa-miR-451
Q28 = hsa-miR-17/hsa-miR-320
Q29 = hsa-miR-106a/hsa-miR-320
Q30 = hsa-miR-15b/hsa-miR-320

TABLE IIIb ratios among measured values of expression of preferred pairs of microRNAs used for evaluating a risk of manifesting a pulmonary tumour (within 1-3 years from collecting the sample of biological fluid).
miRNA Pairs hsa-miR-30b/hsa-miR-320
hsa-miR-30b/hsa-miR-451
hsa-miR-30b/hsa-miR-660
hsa-miR-197/hsa-miR-451
hsa-miR-197/hsa-miR-660
hsa-miR-197/hsa-miR-320
hsa-miR-30c/hsa-miR-451
hsa-miR-30c/hsa-miR-660
hsa-miR-30c/hsa-miR-320

In connection with the risk of manifesting a pulmonary tumor, FIG. 5 shows (on the left hand side) the ROC curve when using the 15 miRNAs of Table Ia to create the 30 ratios of Table IIIa and (on the right end side) the ROC curve when using the 6 miRNAs of Table Ib to create the 9 ratios of Table IIIb.

TABLE IIIc

Another set of ratios among measured values of expression of pairs of miRNAs used for evaluating a risk of manifesting a pulmonary tumour (within 1-3 years from collecting the sample of biological fluid).

| miRNA Pairs | < or > | 3 y storage cut-off |
|---|---|---|
| Q1 = hsa-miR-197/hsa-miR-660 | > | 3.44 |
| Q2 = hsa-miR-197/hsa-miR-92a | > | −1.72 |
| Q3 = hsa-miR-17/hsa-miR-660 | > | 8.63 |
| Q4 = hsa-miR-17/hsa-miR-92a | > | 3.60 |
| Q5 = hsa-miR-197/hsa-miR-451 | > | −2.45 |
| Q6 = hsa-miR-17/hsa-miR-451 | > | 2.77 |
| Q7 = hsa-miR-19b/hsa-miR-660 | > | 7.85 |
| Q8 = hsa-miR-197/hsa-miR-19b | > | −3.96 |
| Q9 = hsa-miR-19b/hsa-miR-451 | > | 1.90 |
| Q10 = hsa-miR-106a/hsa-miR-660 | > | 8.71 |
| Q11 = hsa-miR-106a/hsa-miR-451 | > | 2.87 |
| Q12 = hsa-miR-106a/hsa-miR-92a | > | 3.73 |
| Q13 = hsa-miR-101/hsa-miR-97 | < | −4.59 |
| Q14 = hsa-miR-101/hsa-miR-17 | < | −9.73 |
| Q15 = hsa-miR-133a/hsa-miR-660 | > | −0.11 |
| Q16 = hsa-miR-133a/hsa-miR-451 | > | −5.49 |
| Q17 = hsa-miR-101/hsa-miR-133a | < | −1.34 |
| Q18 = hsa-miR-16/hsa-miR-660 | > | 8.78 |
| Q19 = hsa-miR-16/hsa-miR-451 | > | 2.38 |
| Q20 = hsa-miR-140-3p/hsa-miR-660 | > | −0.31 |
| Q21 = hsa-miR-101/hsa-miR-140-3p | < | −0.11 |
| Q22 = hsa-miR-15b/hsa-miR-451 | > | −1.40 |
| Q23 = hsa-miR-15b/hsa-miR-660 | > | 4.77 |
| Q24 = hsa-miR-142-3p/hsa-miR-15b | < | 2.71 |
| Q25 = hsa-miR-126/hsa-miR-660 | > | 8.08 |
| Q26 = hsa-miR-28-3p/hsa-miR-660 | > | 3.18 |
| Q27 = hsa-miR-320/hsa-miR-660 | > | 6.39 |

Reducing the number of microRNAs and ratios (from the 27$^{th}$ to the 1$^{st}$), the shorter signatures were tested on the validation set, analyzing their power using the mean percent of correct classification among 6 different methods of class prediction analysis:, Compound Covariate Predictor, Diagonal Linear Discriminant Analysis, 1-Nearest Neighbor, 3-Nearest Neighbors, Nearest Centroid and Support Vector Machines. The results are shown in FIG. 16a.

TABLE IIId

Another set of ratios among measured values of expression of preferred pairs of microRNAs used for evaluating a risk of manifesting a pulmonary tumour (within 1-3 years from collecting the sample of biological fluid).
miRNA Pairs hsa-miR-197/hsa-miR-660
hsa-miR-197/hsa-miR-92a
hsa-miR-17/hsa-miR-660
hsa-miR-17/hsa-miR-92a TABLE IIId-continued Another set of ratios among measured values of expression of preferred pairs of microRNAs used for evaluating a risk of manifesting a pulmonary tumour (within 1-3 years from collecting the sample of biological fluid).
miRNA Pairs hsa-miR-197/hsa-miR-451
hsa-miR-17/hsa-miR-451
hsa-miR-19b/hsa-miR-660
hsa-miR-197/hsa-miR-19b
hsa-miR-19b/hsa-miR-451

As used herein, miRNA ratios are real ratios determined by performing a ratio among the measured values of the expression levels of predetermined pairs of molecules of microRNA.

Signature of Risk of Aggressive Disease

The present invention provides methods including: determining the level of expression of the six miRNA listed in Table IIb or IId in a biological sample from a subject, and comparing the level of expression of said miRNA from said sample from said subject to the level of expression of said miRNA from a control biological sample, wherein a change or deviation in the level of expression of said at least six miRNA in said biological sample from said control biological sample identifies a subject at risk of manifesting an aggressive tumor. Preferably, the tumor cannot be detected by CT spiral scan.

The method can further include: calculating a plurality of real quotients by determining a ratio between the level of expression of at least one pair of miRNA from at least six miRNA listed in Table IIb or IId; comparing each of the real quotients with a respective control value; and determining the real quotients which deviate from the respective control quotient value.

The present invention provides the miRNAs, in particular those of appended Table IIa or IIc, as biomarkers for evaluation of the risk of contracting aggressive pulmonary tumour within 1-3 years from the sample collection of biological fluid. Further, in this case too, the ratios between the miRNA expression values were specifically identified as ideal molecular biomarkers to be investigated for the evaluation of the risk of contracting an aggressive pulmonary tumour within 1-3 years from the sample biological fluid collection, which might be whole blood, serum, plasma, saliva or bronchial condensate.

Further, by using the miRNA expression levels of Table IIa or IIc, the ratios were identified between measure values of expression levels relative to pairs of microRNAs of Table IVa or IVc for evaluation of the risk of contracting an aggressive pulmonary tumour within 1-3 years from the sample collection of biological fluid. In more detail, by calculating a sufficient number of real ratios selected from among the ratios of Table IVa or IVc, for example at least 30%, and optionally at least 50%, the progression of the ratios with respect to control ratios can be studied.

An individual is defined as at risk of contracting an aggressive pulmonary tumour in a period comprised between one and three years from the collection of the sample of biological fluid, if in that individual at least 50%, optionally at least 75%, of the real ratios calculated deviate with respect to the respective control ratio value.

As used herein, an aggressive tumour is a tumour, for example a pulmonary tumour, with a lethal prognosis or capable of causing death in 90% of patients within five years from diagnosis of the disease.

The use of miRNA ratios also enables reliably predicting the development of pulmonary tumour, in particular of the more aggressive form, in high-risk individuals (more than 50 years of age and heavy smokers) up to two years before the disease is at a visible stage with the better imaging techniques at present available (spiral CT). Note also that the method using the calculation of the ratios, or miRNA ratios, described above can be actuated with a simple collection of a blood sample and is therefore entirely non-invasive, and allows the analysis to be performed rapidly and economically.

TABLE IIa microRNAs used for evaluation of the risk of manifesting an aggressive pulmonary tumour (within 1-3 years from collecting the sample of biological fluid).
miRNA hsa-miR-660
hsa-miR-140-5p
hsa-miR-486-5p
hsa-miR-197
hsa-miR-221
hsa-miR-451
hsa-miR-28-3p
hsa-miR-148a
hsa-miR-19b
hsa-miR-15b
hsa-miR-30c
hsa-miR-30b
hsa-miR-101
hsa-miR-21
hsa-miR-140-3p
hsa-miR-142-3p Comparing the miRNAs listed in Table IIa in pre-disease patient samples of aggressive lung cancer v. pre-disease samples of indolent lung cancer and disease free samples (control) results showed a sensitivity of 94.5 (training sensitivity of 90.9; validation sensitivity of 100.0) and a specificity of 97.6 (training specificity of 100.0; validation specificity of 96.0).

TABLE IIb preferred microRNAs used for evaluation of the risk of manifesting an aggressive pulmonary tumour (within 1-3 years from collecting the sample of biological fluid).
miRNA hsa-miR-660
hsa-miR-486-5p
hsa-miR-221
hsa-miR-28-3p
hsa-miR-148a
hsa-miR-19b Comparing the miRNAs listed in Table IIb in pre-disease patient samples of aggressive lung cancer v. pre-disease samples of indolent lung cancer and disease free samples (control) results showed a sensitivity of 94.5 (training sensitivity of 90.9; validation sensitivity of 100.0) and a specificity of 95.0 (training specificity of 100.0; validation specificity of 92.0).

TABLE IIc

Another set of microRNAs used for evaluation of the risk of manifesting an aggressive pulmonary tumour (within 1-3 years from collecting the sample of biological fluid).
miRNA hsa-miR-21
hsa-miR-451
hsa-miR-197
hsa-miR-17
hsa-miR-15b
hsa-miR-106a
hsa-miR-16
hsa-miR-92a
hsa-miR-19b
hsa-miR-101
hsa-miR-145
hsa-miR-28-3p
hsa-miR-30c
hsa-miR-320
hsa-miR-126
hsa-miR-221
hsa-miR-148a
hsa-miR-30b
hsa-miR-140-3p

TABLE IId

Another set of preferred microRNAs used for evaluation of the risk of manifesting an aggressive pulmonary tumour (within 1-3 years from collecting the sample of biological fluid).
miRNA hsa-miR-21
hsa-miR-451
hsa-miR-197
hsa-miR-17
hsa-miR-15b
hsa-miR-106a

TABLE IIe

Another set of preferred microRNAs used for evaluation of the risk of manifesting an aggressive pulmonary tumour (within 1-3 years from collecting the sample of biological fluid).
miRNA hsa-miR-197
hsa-miR-451

TABLE IIf

Another set of preferred microRNAs used for evaluation of the risk of manifesting an aggressive pulmonary tumour (within 1-3 years from collecting the sample of biological fluid).
miRNA hsa-miR-197
hsa-miR-101

TABLE IIg

Another set of preferred microRNAs used for evaluation of the risk of manifesting an aggressive pulmonary tumour (within 1-3 years from collecting the sample of biological fluid).
miRNA hsa-miR-197
hsa-miR-28-3p
hsa-miR-451
hsa-miR-101

TABLE IVa ratios among measured values of expression of pairs of microRNAs used for determining a risk of manifesting an aggressive pulmonary tumour (within 1-3 years from collecting the sample of biological fluid).
miRNA Pairs Q1 = hsa-miR-221/hsa-miR-660
Q2 = hsa-miR-221/hsa-miR-486-5p
Q3 = hsa-miR-221/hsa-miR-451
Q4 = hsa-miR-140-3p/hsa-miR-221
Q5 = hsa-miR-21/hsa-miR-221
Q6 = hsa-miR-101/hsa-miR-221
Q7 = hsa-miR-197/hsa-miR-660
Q8 = hsa-miR-197/hsa-miR-486-5p
Q9 = hsa-miR-140-5p/hsa-miR-660
Q10 = hsa-miR-140-5p/hsa-miR-486-5p
Q11 = hsa-miR-140-5p/hsa-miR-19b
Q12 = hsa-miR-142-3p/hsa-miR-660
Q13 = hsa-miR-148a/hsa-miR-660
Q14 = hsa-miR-148a/hsa-miR-486-5p
Q15 = hsa-miR-148a/hsa-miR-19b
Q16 = hsa-miR-148a/hsa-miR-451
Q17 = hsa-miR-15b/hsa-miR-660
Q18 = hsa-miR-15b/hsa-miR-486-5p
Q19 = hsa-miR-15b/hsa-miR-19b
Q20 = hsa-miR-19b/hsa-miR-221
Q21 = hsa-miR-19b/hsa-miR-30c
Q22 = hsa-miR-28-3p/hsa-miR-660
Q23 = hsa-miR-28-3p/hsa-miR-486-5p
Q24 = hsa-miR-30b/hsa-miR-660
Q25 = hsa-miR-30b/hsa-miR-486-5p
Q26 = hsa-miR-30c/hsa-miR-660
Q27 = hsa-miR-30c/hsa-miR-486-5p
Q28 = hsa-miR-19b/hsa-miR-28-3p

TABLE IVb ratios among measured values of expression of preferred pairs of microRNAs used for determining a risk of manifesting an aggressive pulmonary tumour (within 1-3 years from collecting the sample of biological fluid).
miRNA Pairs hsa-miR-221/hsa-miR-660
hsa-miR-28-3p/hsa-miR-660
hsa-miR-19b/hsa-miR-221
hsa-miR-19b/hsa-miR-28-3p
hsa-miR-148a/hsa-miR-19b
hsa-miR-148a/hsa-miR-486-5p
hsa-miR-28-3p/hsa-miR-486-5p
hsa-miR-221/hsa-miR-486-5p
hsa-miR-148a/hsa-miR-660

In connection with the risk of manifesting an aggressive pulmonary tumor, FIG. 6 shows (on the left hand side) the ROC curve when using the 16 miRNAs of Table IIa to create the 28 ratios of Table IVa and (on the right end side) the ROC curve when using the 6 miRNAs of Table IIb to create the 9 ratios of Table IVb.

TABLE IVc

Another set of ratios among measured values of expression of pairs of microRNAs used for determining a risk of manifesting an aggressive pulmonary tumour (within 1-3 years from collecting the sample of biological fluid).

| miRNA Pairs | < or > | 3 y storage cut-off |
|---|---|---|
| Q1 = hsa-miR-101/hsa-miR-197 | < | −4.51 |
| Q2 = hsa-miR-197/hsa-miR-451 | > | −2.07 |
| Q3 = hsa-miR-101/hsa-miR-28-3p | < | −4.42 |
| Q4 = hsa-miR-28-3p/hsa-miR-451 | > | −2.36 |
| Q5 = hsa-miR-197/hsa-miR-21 | > | −0.38 |
| Q6 = hsa-miR-21/hsa-miR-28-3p | < | 0.78 |

TABLE IVc-continued

Another set of ratios among measured values of expression of pairs of microRNAs used for determining a risk of manifesting an aggressive pulmonary tumour (within 1-3 years from collecting the sample of biological fluid).

| miRNA Pairs | < or > | 3 y storage cut-off |
|---|---|---|
| Q7 = hsa-miR-101/hsa-miR-106a | < | −9.85 |
| Q8 = hsa-miR-106a/hsa-miR-451 | > | 3.14 |
| Q9 = hsa-miR-106a/hsa-miR-21 | > | 4.81 |
| Q10 = hsa-miR-16/hsa-miR-28-3p | < | 4.72 |
| Q11 = hsa-miR-16/hsa-miR-197 | < | 4.56 |
| Q12 = hsa-miR-106a/hsa-miR-16 | > | 0.66 |
| Q13 = hsa-miR-101/hsa-miR-17 | < | −9.74 |
| Q14 = hsa-miR-17/hsa-miR-451 | > | 3.04 |
| Q15 = hsa-miR-17/hsa-miR-21 | > | 4.67 |
| Q16 = hsa-miR-16/hsa-miR-17 | < | −0.56 |
| Q17 = hsa-miR-28-3p/hsa-miR-92a | > | −1.6 |
| Q18 = hsa-miR-197/hsa-miR-92a | > | −1.36 |
| Q19 = hsa-miR-197/hsa-miR-30c | > | −1.51 |
| Q20 = hsa-miR-28-3p/hsa-miR-30c | > | −1.79 |
| Q21 = hsa-miR-320/hsa-miR-92a | > | 1.42 |
| Q22 = hsa-miR-320/hsa-miR-451 | > | 0.66 |
| Q23 = hsa-miR-221/hsa-miR-451 | > | −0.2 |
| Q24 = hsa-miR-21/hsa-miR-221 | < | −1.33 |
| Q25 = hsa-miR-145/hsa-miR-197 | < | −0.96 |
| Q26 = hsa-miR-145/hsa-miR-28-3p | < | −0.69 |
| Q27 = hsa-miR-28-3p/hsa-miR-30b | > | −3.47 |
| Q28 = hsa-miR-197/hsa-miR-30b | > | −3.2 |
| Q29 = hsa-miR-19b/hsa-miR-451 | > | 2.19 |
| Q30 = hsa-miR-126/hsa-miR-451 | > | 2.24 |
| Q31 = hsa-miR-15b/hsa-miR-451 | > | −1.2 |
| Q32 = hsa-miR-148a/hsa-miR-197 | < | −3.38 |
| Q33 = hsa-miR-140-3p/hsa-miR-451 | > | −6.81 |

Figure 16B:
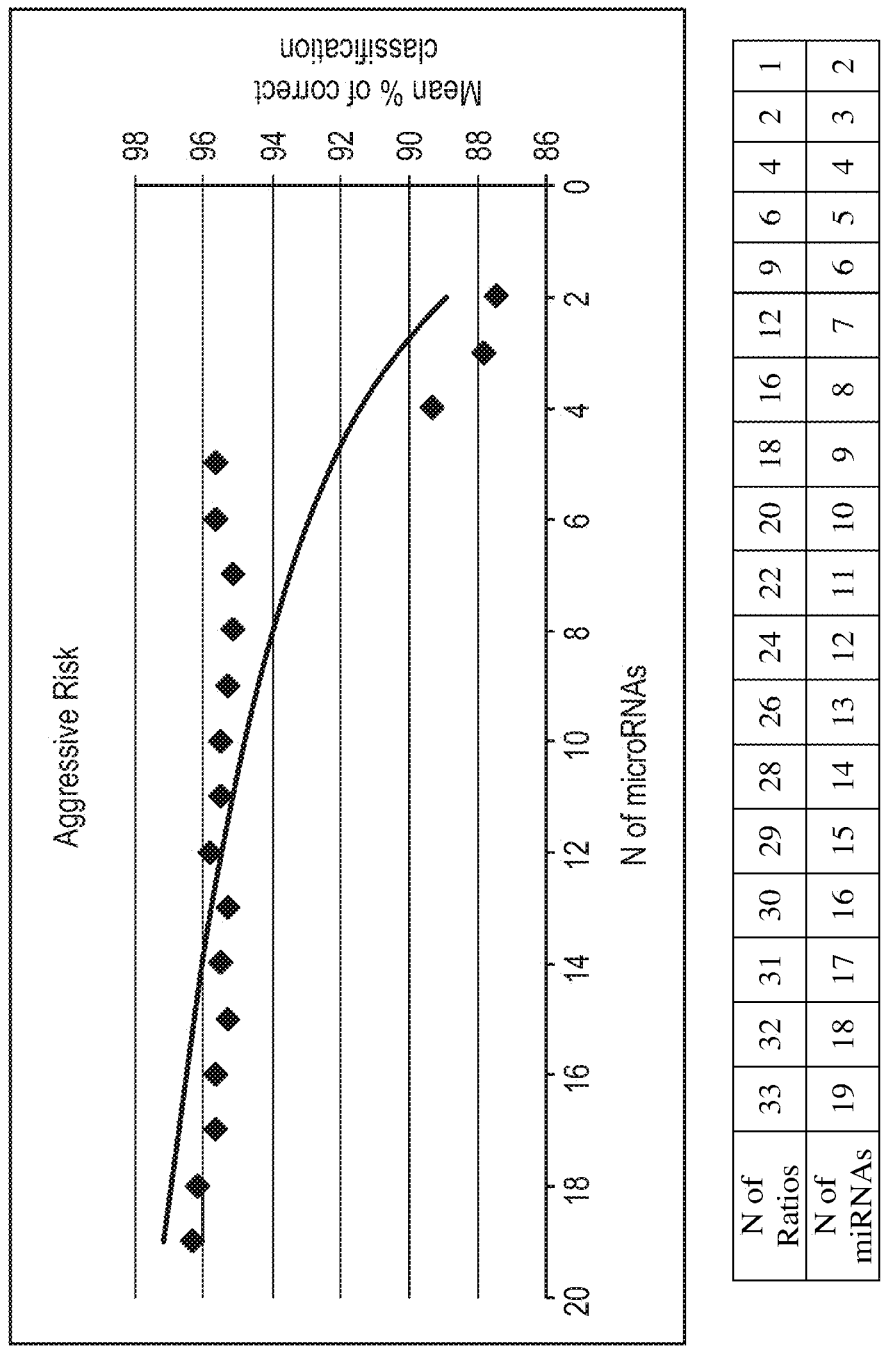
FIG. 16B is graph showing the number of miRNA and ratio of miRNA for a signature of aggressive risk.

Reducing the number of microRNAs and ratios (from the $33^{rd}$ to the $1^{st}$), the shorter signatures were tested on the validation set, analyzing their power using the mean percent of correct classification among 6 different methods of class prediction analysis:, Compound Covariate Predictor, Diagonal Linear Discriminant Analysis, 1-Nearest Neighbor, 3-Nearest Neighbors, Nearest Centroid and Support Vector Machines. The results are shown in FIG. 16b.

TABLE IVd

Another set of ratios among measured values of expression of preferred pairs of microRNAs used for determining a risk of manifesting an aggressive pulmonary tumour (within 1-3 years from collecting the sample of biological fluid).
miRNA Pairs hsa-miR-101/hsa-miR-197
hsa-miR-197/hsa-miR-451
hsa-miR-101/hsa-miR-28-3p
hsa-miR-28-3p/hsa-miR-451
hsa-miR-197/hsa-miR-21
hsa-miR-21/hsa-miR-28-3p
hsa-miR-101/hsa-miR-106a
hsa-miR-106a/hsa-miR-451
hsa-miR-106a/hsa-miR-21

Signature of Diagnosis

The present invention provides a method including: determining the level of expression of the six miRNA listed in Table Vb or Vd in a biological sample from a subject, and comparing the level of expression of said miRNA from said sample from said subject to the level of expression of said miRNA from a control biological sample, wherein a change or deviation in the level of expression of said at least six miRNA in said biological sample from said control biological sample determines the presence of a tumor in said subject. Preferably, determination of the presence of said tumor confirms detection by CT spiral scan.

The method can further include: calculating a plurality of real quotients by determining a ratio between the level of expression of at least one pair of miRNA from at least six miRNA listed in Table Vb or Vd; comparing each of the real quotients with a respective control value; and determining the real quotients which deviate from the respective control quotient value.

The present invention provides miRNAs, and in particular those listed in Table Va or Vc, have a role as biomolecular markers for determining the actual presence of a pulmonary tumour in an individual, for diagnostic purposes.

The present invention also provides the ratios between expression level values of miRNA pairs are valid biomarkers with a diagnostic and prognostic function. In detail, the miRNAs of Table Va or Vc were used for determining the ratios of Table VIIa or VIIc which represent ratios between measured values of expression levels of relative microRNA pairs and which are used to determine the actual presence (diagnosis) of a pulmonary tumour in an individual. In more detail, by calculating at least 20% of the real ratios of Table VIIa or VIIc it is possible to define the individual presents a pulmonary tumour if at least 30% of the real ratios (as in Table VIIa or VIIc) calculated deviate from the respective control value.

TABLE Va microRNAs used for determining the actual presence of a pulmonary tumour in an individual.
miRNA hsa-miR-106a
hsa-miR-140-3p
hsa-miR-17
hsa-miR-660
hsa-miR-15b
hsa-miR-92a
hsa-miR-451
hsa-miR-19b
hsa-miR-28-3p
hsa-miR-133a
hsa-miR-101
hsa-miR-197
hsa-miR-145
hsa-miR-320
hsa-miR-21
hsa-miR-30b
hsa-miR-126
hsa-miR-140-5p Comparing the miRNAs listed in Table Va in the plasma of patients at surgery v. disease free samples (control) results showed a sensitivity of 80.5 (training sensitivity of 84.2; validation sensitivity of 76.5) and a specificity of 95.5 (training specificity of 100.0; validation specificity of 93.3).

TABLE Vb preferred microRNAs used for determining the actual presence of a pulmonary tumour in an individual.
miRNA hsa-miR-106a
hsa-miR-17
hsa-miR-660
hsa-miR-92a
hsa-miR-451
hsa-miR-197

Comparing the miRNAs listed in Table Vb in the plasma of patients at surgery v. disease free samples (control) results showed a sensitivity of 77.8 (training sensitivity of 84.2;

validation sensitivity of 70.6) and a specificity of 90.9 (training specificity of 85.7; validation specificity of 93.3).

TABLE Vc

Another set of microRNAs used for determining the actual presence of a pulmonary tumour in an individual.
miRNA hsa-miR-660
hsa-miR-197
hsa-miR-17
hsa-miR-106a
hsa-miR-142-3p
hsa-miR-92a
hsa-miR-19b
hsa-miR-101
hsa-miR-145
hsa-miR-28-3p
hsa-miR-320
hsa-miR-126
hsa-miR-140-5p
hsa-miR-148

TABLE Vd

Another set of preferred microRNAs used for determining the actual presence of a pulmonary tumour in an individual.
miRNA hsa-miR-660
hsa-miR-197
hsa-miR-17
hsa-miR-106a
hsa-miR-142-3p
hsa-miR-92a

TABLE Ve

Another set of preferred microRNAs used for determining the actual presence of a pulmonary tumour in an individual.
miRNA hsa-miR-660
hsa-miR-197

TABLE Vf

Another set of preferred microRNAs used for determining the actual presence of a pulmonary tumour in an individual.
miRNA hsa-miR-197
hsa-miR-106a
hsa-miR-660
hsa-miR-92a

TABLE VIIa ratios among measured values of expression of pairs of microRNAs used for determining an actual presence of pulmonary tumour in an individual.
miRNA Pairs Q1 = hsa-miR-17/hsa-miR-451
Q2 = hsa-miR-106a/hsa-miR-451
Q3 = hsa-miR-133a/hsa-miR-451
Q4 = hsa-miR-17/hsa-miR-660
Q5 = hsa-miR-106a/hsa-miR-660
Q6 = hsa-miR-197/hsa-miR-451
Q7 = hsa-miR-133a/hsa-miR-660
Q8 = hsa-miR-145/hsa-miR-451

TABLE VIIa-continued ratios among measured values of expression of pairs of microRNAs used for determining an actual presence of pulmonary tumour in an individual.
miRNA Pairs Q9 = hsa-miR-28-3p/hsa-miR-451
Q10 = hsa-miR-17/hsa-miR-92a
Q11 = hsa-miR-106a/hsa-miR-92a
Q12 = hsa-miR-197/hsa-miR-660
Q13 = hsa-miR-133a/hsa-miR-92a
Q14 = hsa-miR-145/hsa-miR-660
Q15 = hsa-miR-28-3p/hsa-miR-660
Q16 = hsa-miR-15b/hsa-miR-451
Q17 = hsa-miR-19b/hsa-miR-451
Q18 = hsa-miR-30b/hsa-miR-451
Q19 = hsa-miR-17/hsa-miR-320
Q20 = hsa-miR-106a/hsa-miR-320
Q21 = hsa-miR-17/hsa-miR-21
Q22 = hsa-miR-106a/hsa-miR-21
Q23 = hsa-miR-197/hsa-miR-92a
Q24 = hsa-miR-101/hsa-miR-106a
Q25 = hsa-miR-133a/hsa-miR-320
Q26 = hsa-miR-101/hsa-miR-17
Q27 = hsa-miR-145/hsa-miR-92a
Q28 = hsa-miR-28-3p/hsa-miR-92a
Q29 = hsa-miR-106a/hsa-miR-140-3p
Q30 = hsa-miR-15b/hsa-miR-660
Q31 = hsa-miR-19b/hsa-miR-660
Q32 = hsa-miR-30b/hsa-miR-660
Q33 = hsa-miR-126/hsa-miR-451
Q34 = hsa-miR-140-5p/hsa-miR-451
Q35 = hsa-miR-133a/hsa-miR-21
Q36 = hsa-miR-140-3p/hsa-miR-17

TABLE VIIb ratios among measured values of expression of preferred pairs of microRNAs used for determining an actual presence of pulmonary tumour in an individual.
miRNA Pairs hsa-miR-106a/hsa-miR-660
hsa-miR-106a/hsa-miR-92a
hsa-miR-106a/hsa-miR-451
hsa-miR-17/hsa-miR-451
hsa-miR-17/hsa-miR-660
hsa-miR-17/hsa-miR-92a
hsa-miR-197/hsa-miR-451
hsa-miR-197/hsa-miR-92a
hsa-miR-197/hsa-miR-660

In connection with the determination of the actual presence of a pulmonary tumour in an individual, FIG. 7 shows (on the left hand side) the ROC curve when using the 18 miRNAs of Table Va to create the 36 ratios of Table VIIa and (on the right end side) the ROC curve when using the 6 miRNAs of Table Vb to create the 9 ratios of Table VIIb.

TABLE VIIc

Another set of ratios among measured values of expression of pairs of microRNAs used for determining an actual presence of pulmonary tumour in an individual.

| miRNA Pairs | < or > | 3 y storage cut-off |
|---|---|---|
| Q1 = hsa-miR-197/hsa-miR-660 | > | 3.58 |
| Q2 = hsa-miR-197/hsa-miR-92a | > | −1.5 |
| Q3 = hsa-miR-106a/hsa-miR-92a | > | 3.73 |
| Q4 = hsa-miR-106a/hsa-miR-660 | > | 8.87 |
| Q5 = hsa-miR-106a/hsa-miR-197 | < | 4.97 |
| Q6 = hsa-miR-142-3p/hsa-miR-197 | < | 3.73 |
| Q7 = hsa-miR-140-5p/hsa-miR-197 | < | −0.03 |
| Q8 = hsa-miR-142-3p/hsa-miR-28-3p | < | 4.19 |
| Q9 = hsa-miR-140-5p/hsa-miR-28-3p | < | 0.33 |

TABLE VIIc-continued

Another set of ratios among measured values of expression of pairs of microRNAs used for determining an actual presence of pulmonary tumour in an individual.

| miRNA Pairs | < or > | 3 y storage cut-off |
|---|---|---|
| Q10 = hsa-miR-28-3p/hsa-miR-660 | > | 3.18 |
| Q11 = hsa-miR-28-3p/hsa-miR-92a | > | −1.79 |
| Q12 = hsa-miR-17/hsa-miR-660 | > | 8.63 |
| Q13 = hsa-miR-17/hsa-miR-92a | > | 3.6 |
| Q14 = hsa-miR-142-3p/hsa-miR-145 | < | 3.94 |
| Q15 = hsa-miR-145/hsa-miR-660 | > | 3.76 |
| Q16 = hsa-miR-145/hsa-miR-92a | > | −1.35 |
| Q17 = hsa-miR-197/hsa-miR-320 | > | −2.45 |
| Q18 = hsa-miR-106a/hsa-miR-320 | > | 2.79 |
| Q19 = hsa-miR-17/hsa-miR-320 | > | 2.64 |
| Q20 = hsa-miR-148a/hsa-miR-92a | > | −4.41 |
| Q21 = hsa-miR-148a/hsa-miR-660 | > | 0.76 |
| Q22 = hsa-miR-19b/hsa-miR-660 | > | 7.95 |
| Q23 = hsa-miR-19b/hsa-miR-92a | > | 2.75 |
| Q24 = hsa-miR-101/hsa-miR-660 | > | −0.08 |
| Q25 = hsa-miR-101/hsa-miR-92a | > | −5.18 |
| Q26 = hsa-miR-126/hsa-miR-660 | > | 8.08 |
| Q27 = hsa-miR-126/hsa-miR-92a | > | 3.05 |

Reducing the number of microRNAs and ratios (from the $27^{th}$ to the $1^{st}$), the shorter signatures were tested on the validation set, analyzing their power using the mean percent of correct classification among 6 different methods of class prediction analysis:, Compound Covariate Predictor, Diagonal Linear Discriminant Analysis, 1-Nearest Neighbor, 3-Nearest Neighbors, Nearest Centroid and Support Vector Machines. The results are shown in FIG. 16c.

TABLE VIId

Another set of ratios among measured values of expression of preferred pairs of microRNAs used for determining an actual presence of pulmonary tumour in an individual.
miRNA Pairs hsa-miR-197/hsa-miR-660
hsa-miR-197/hsa-miR-92a
hsa-miR-106a/hsa-miR-92a
hsa-miR-106a/hsa-miR-660
hsa-miR-106a/hsa-miR-197
hsa-miR-142-3p/hsa-miR-197
hsa-miR-140-5p/hsa-miR-197
hsa-miR-142-3p/hsa-miR-28-3p
hsa-miR-140-5p/hsa-miR-28-3p
hsa-miR-28-3p/hsa-miR-660
hsa-miR-28-3p/hsa-miR-92a Signature of Presence of Aggressive Disease The present invention provides a method including: determining the level of expression of the six miRNA listed in Table VIb or VId in a biological sample from a subject, and comparing the level of expression of said miRNA from said sample from said subject to the level of expression of said miRNA from a control biological sample, wherein a change or deviation in the level of expression of said at least six miRNA in said biological sample from said control biological sample determines the presence of an aggressive tumor in said subject. Preferably, the determination provides a prognosis of disease-free survival following surgical intervention.

The method can further include: calculating a plurality of real quotients by determining a ratio between the level of expression of at least one pair of miRNA from at least six miRNA listed in Table VIb or VId; comparing each of the real quotients with a respective control value; and determining the real quotients which deviate from the respective control quotient value.

The present invention provides miRNAs, and in particular those listed in Table VIa or VIc, that can be used as biomolecular markers for determining the actual presence of an aggressive pulmonary tumour in an individual (prognosis). The present invention demonstrates in particular the ratios between values of expression levels of miRNA pairs are valid biomarkers with a diagnostic and prognostic function even in the case of an aggressive tumour.

In detail, the miRNAs of Table VIa and VIc were used to determine the ratios of Table VIIIa and VIIIc where there is a list of ratios between the measured values of the expression levels relative to microRNA pairs of Table VIa and VIc used for determining the actual presence of an aggressive pulmonary tumour in an individual. In detail, by detecting at least 20% of the real ratios of Table VIIIa and VIIIc, it is possible to define an individual having an aggressive pulmonary tumour as one in whom at least 60% of the real ratios that have been calculated deviate with respect to the respective control value.

Thus the use of the described procedure can help also to resolve the problem of overdiagnosis and overtreatment in patients who are not at risk.

In greater detail, in a context of surveillance of the disease using spiral CT, the use of a test based on this method might enable selection of only a sub-group of patients at high risk of developing the disease to be subsequently kept under a more strict control. Further, the ability of the test to predict the patients who will develop a more aggressive disease, frequently not diagnosed by the CT scan, enables directing these individuals directly to specific pharmacological programmes (including giving up smoking) and/or the use of more specific diagnostic examinations based on the metabolic-biological characteristics such as PET with various tracers or body MRI, or a different local treatment such as stereotaxic radiotherapy, or other treatments besides. The use of miRNA ratios is an easily-applicable method with a potential current clinical use and which avoids the use of more profound and complex analysis.

TABLE VIa microRNAs used for determining the actual presence of an aggressive pulmonary tumour in an individual.
miRNA hsa-miR-142-3p
hsa-miR-148a
hsa-miR-15b
hsa-miR-21
hsa-miR-221
hsa-miR-660
hsa-miR-19b
hsa-miR-486-5p
hsa-miR-30b
hsa-miR-16

Comparing the miRNAs listed in Table VIa in patient samples of aggressive lung cancer v. pre-disease samples of indolent lung cancer and disease free samples (control) results showed a sensitivity of 86.7 (training sensitivity of 80.0; validation sensitivity of 100.0) and a specificity of 93.2 (training specificity of 94.0; validation specificity of 92.6).

TABLE VIb preferred microRNAs used for determining the actual presence of an aggressive pulmonary tumour in an individual.
miRNA hsa-miR-142-3p
hsa-miR-21
hsa-miR-221

TABLE VIb-continued preferred microRNAs used for determining the actual presence of an aggressive pulmonary tumour in an individual.
miRNA hsa-miR-660
hsa-miR-19b
hsa-miR-486-5p Comparing the miRNAs listed in Table VIb in patient samples of aggressive lung cancer v. pre-disease samples of indolent lung cancer and disease free samples (control) results showed a sensitivity of 80.0 (training sensitivity of 80.0; validation sensitivity of 80.0) and a specificity of 93.2 (training specificity of 94.0; validation specificity of 92.6).

TABLE VIc

Another set of microRNAs used for determining the actual presence of an aggressive pulmonary tumour in an individual.
miRNA hsa-miR-660
hsa-miR-197
hsa-miR-17
hsa-miR-106a
hsa-miR-142-3p
hsa-miR-92a
hsa-miR-19b
hsa-miR-101
hsa-miR-145
hsa-miR-28-3p
hsa-miR-451
hsa-miR-126
hsa-miR-140-5p
hsa-miR-148a
hsa-miR-486-5p
hsa-miR-21
hsa-miR-16
hsa-miR-30b
hsa-miR-30c
hsa-miR-15b

TABLE VId

Another set of preferred microRNAs used for determining the actual presence of an aggressive pulmonary tumour in an individual.
miRNA hsa-miR-660
hsa-miR-197
hsa-miR-17
hsa-miR-106a
hsa-miR-142-3p
hsa-miR-92a

TABLE VIe

Another set of preferred microRNAs used for determining the actual presence of an aggressive pulmonary tumour in an individual.
miRNA hsa-miR-451
hsa-miR-197

TABLE VIf

Another set of preferred microRNAs used for determining the actual presence of an aggressive pulmonary tumour in an individual.
miRNA hsa-miR-197
hsa-miR-486-5p
hsa-miR-451

TABLE VIIIa ratios among measured values of expression of pairs of microRNAs used for determining an actual presence of aggressive pulmonary tumour in an individual.
miRNA Pairs Q1 = hsa-miR-142-3p/hsa-miR-486-5p
Q2 = hsa-miR-21/hsa-miR-486-5p
Q3 = hsa-miR-221/hsa-miR-486-5p
Q4 = hsa-miR-19b/hsa-miR-21
Q5 = hsa-miR-19b/hsa-miR-221
Q6 = hsa-miR-142-3p/hsa-miR-19b
Q7 = hsa-miR-148a/hsa-miR-486-5p
Q8 = hsa-miR-15b/hsa-miR-486-5p
Q9 = hsa-miR-30b/hsa-miR-486-5p
Q10 = hsa-miR-142-3p/hsa-miR-660
Q11 = hsa-miR-221/hsa-miR-660
Q12 = hsa-miR-148a/hsa-miR-19b
Q13 = hsa-miR-15b/hsa-miR-19b
Q14 = hsa-miR-19b/hsa-miR-30b
Q15 = hsa-miR-16/hsa-miR-486-5p
Q16 = hsa-miR-21/hsa-miR-660

TABLE VIIIb ratios among measured values of expression of preferred pairs of microRNAs used for determining an actual presence of aggressive pulmonary tumour in an individual.
miRNA Pairs Q1 = hsa-miR-hsa-miR-142-3p/hsa-miR-660
hsa-miR-142-3p/hsa-miR-19b
hsa-miR-21/hsa-miR-660
hsa-miR-221/hsa-miR-660
hsa-miR-19b/hsa-miR-21
hsa-miR-19b/hsa-miR-221
hsa-miR-142-3p/hsa-miR-486-5p
hsa-miR-221/hsa-miR-486-5p
hsa-miR-21/hsa-miR-486-5p In connection with the determination of the actual presence of an aggressive pulmonary tumour in an individual, FIG. 8 shows (on the left hand side) the ROC curve when using the 10 miRNAs of Table VIa to create the 16 ratios of Table VIIIa and (on the right end side) the ROC curve when using the 6 miRNAs of Table VIb to create the 9 ratios of Table VIIIb.

TABLE VIIIc

Another set of ratios among measured values of expression of pairs of microRNAs used for determining an actual presence of aggressive pulmonary tumour in an individual.

| miRNA Pairs | < or > | 3 y storage cut-off |
|---|---|---|
| Q1 = hsa-miR-197/hsa-miR-451 | > | −1.76 |
| Q2 = hsa-miR-197/hsa-miR-486-5p | > | −1.65 |
| Q3 = hsa-miR-106a/hsa-miR-197 | < | 4.9 |
| Q4 = hsa-miR-106a/hsa-miR-486-5p | > | 3.59 |
| Q5 = hsa-miR-106a/hsa-miR-451 | > | 3.14 |
| Q6 = hsa-miR-17/hsa-miR-197 | < | 4.79 |
| Q7 = hsa-miR-17/hsa-miR-486-5p | > | 3.49 |
| Q8 = hsa-miR-17/hsa-miR-451 | > | 3.21 |

TABLE VIIIc-continued

Another set of ratios among measured values of expression of pairs of microRNAs used for determining an actual presence of aggressive pulmonary tumour in an individual.

| miRNA Pairs | < or > | 3 y storage cut-off |
|---|---|---|
| Q9 = hsa-miR-126/hsa-miR-197 | < | 4.17 |
| Q10 = hsa-miR-126/hsa-miR-486-5p | > | 2.75 |
| Q11 = hsa-miR-126/hsa-miR-451 | > | 2.58 |
| Q12 = hsa-miR-197/hsa-miR-660 | > | 4.59 |
| Q13 = hsa-miR-126/hsa-miR-660 | > | 8.46 |
| Q14 = hsa-miR-28-3p/hsa-miR-660 | > | 3.53 |
| Q15 = hsa-miR-28-3p/hsa-miR-486-5p | > | −2.41 |
| Q16 = hsa-miR-28-3p/hsa-miR-451 | > | −2.36 |
| Q17 = hsa-miR-197/hsa-miR-19b | > | −3.97 |
| Q18 = hsa-miR-19b/hsa-miR-486-5p | > | 2.41 |
| Q19 = hsa-miR-19b/hsa-miR-660 | > | 8.42 |
| Q20 = hsa-miR-19b/hsa-miR-451 | > | 2.19 |
| Q21 = hsa-miR-140-5p/hsa-miR-197 | < | −0.52 |
| Q22 = hsa-miR-140-5p/hsa-miR-28-3p | < | 0.28 |
| Q23 = hsa-miR-16/hsa-miR-197 | < | 4.48 |
| Q24 = hsa-miR-197/hsa-miR-92a | > | −1.14 |
| Q25 = hsa-miR-101/hsa-miR-197 | < | −4.51 |
| Q26 = hsa-miR-145/hsa-miR-451 | > | −2 |
| Q27 = hsa-miR-148a/hsa-miR-451 | > | −4.77 |
| Q28 = hsa-miR-142-3p/hsa-miR-197 | < | 3 |
| Q29 = hsa-miR-30b/hsa-miR-451 | > | 1.2 |
| Q30 = hsa-miR-15b/hsa-miR-451 | > | −1.2 |
| Q31 = hsa-miR-30c/hsa-miR-451 | > | −0.3 |
| Q32 = hsa-miR-197/hsa-miR-21 | > | −0.21 |

Figure 16D:
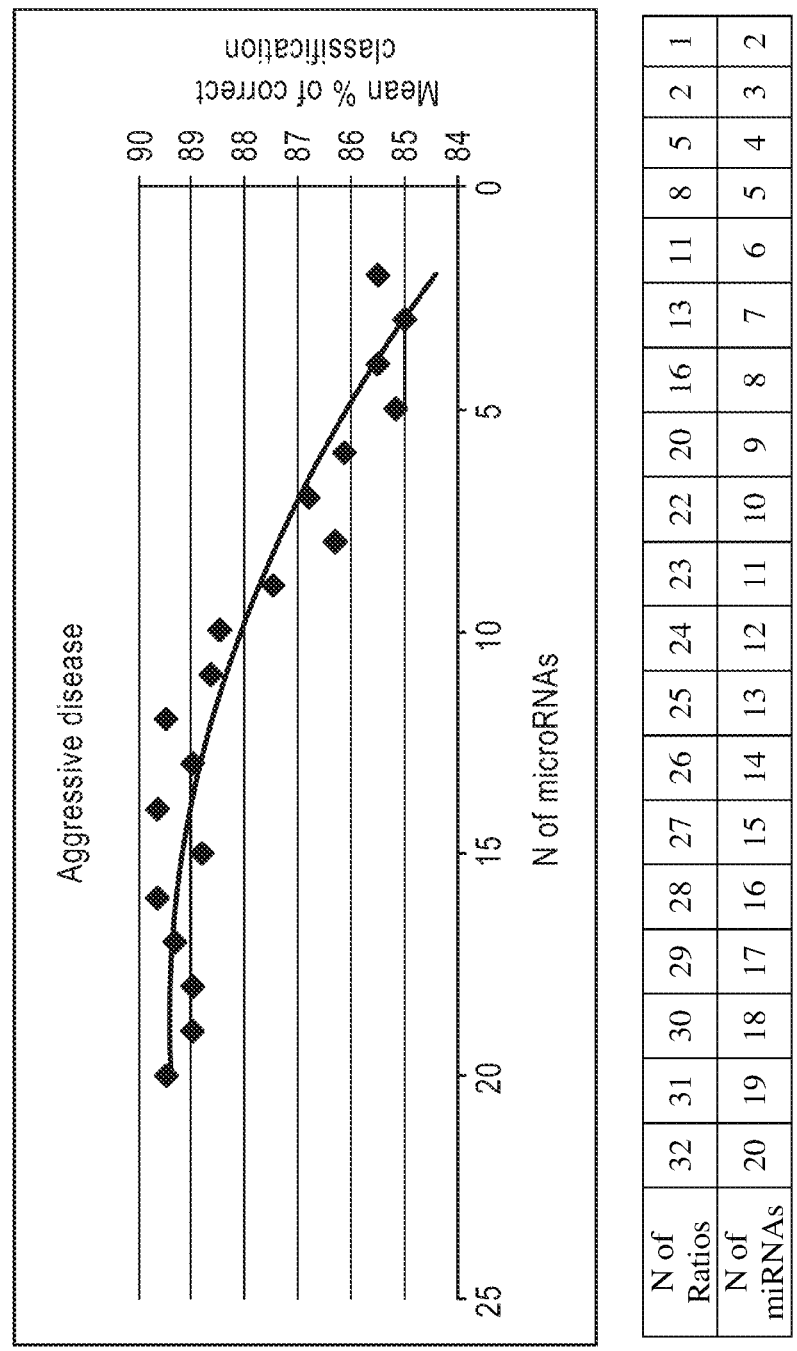
FIG. 16D is graph showing the number of miRNA and ratio of miRNA for a signature of aggressive disease.

Reducing the number of microRNAs and ratios (from the $32^{nd}$ to the $1^{st}$), the shorter signatures were tested on the validation set, analyzing their power using the mean percent of correct classification among 6 different methods of class prediction analysis:, Compound Covariate Predictor, Diagonal Linear Discriminant Analysis, 1-Nearest Neighbor, 3-Nearest Neighbors, Nearest Centroid and Support Vector Machines. The results are shown in FIG. 16d.

TABLE VIIId

Another set of ratios among measured values of expression of preferred pairs of microRNAs used for determining an actual presence of aggressive pulmonary tumour in an individual.
miRNA Pairs hsa-miR-197/hsa-miR-451
hsa-miR-197/hsa-miR-486-5p
hsa-miR-106a/hsa-miR-197
hsa-miR-106a/hsa-miR-486-5p
hsa-miR-106a/hsa-miR-451
hsa-miR-17/hsa-miR-197
hsa-miR-17/hsa-miR-486-5p
hsa-miR-17/hsa-miR-451
hsa-miR-126/hsa-miR-197
hsa-miR-126/hsa-miR-486-5p
hsa-miR-126/hsa-miR-451

Once the miRNA profile of the subject is obtained, it is necessary to determine for each ratio if the value exceed a predetermined cut-off value. The results from the training and validation set show that for the signatures of risk and diagnosis, described above in Tables IIIc and VIIc, respectively, at least 30% (e.g., about 10 out of 27) of the ratios must exceed the cut-off to consider the subject positive for the test. For the two signatures of aggressiveness, described above in Tables IVc and VIIIc, respectively, at least 50% (e.g., 17 out of 33 and 17 out of 32) of the ratios must exceed the cut-off to consider the patient positive for the signature of aggressive risk and presence of aggressive disease, respectively. When reducing the number of miRNAs composing the signature the percentage of positive ratios must be the same. The cut-off values were obtained with the validation set from samples stored for almost 3 years, and the values are shown in Tables IIIc, IVc, VIIc and VIIIc.

If a subject is determined to be positive to more than one signature, the most critical one is considered in this order: risk, diagnosis (both low risk), risk of aggressive disease, presence of aggressive disease (both high risk). A flow chart is shown in FIG. 17.

Compositions and Methods of Treatment

The method can further comprise altering the level of expression of at least one miRNA, at least two miRNA or at least six miRNA, for which the level of expression changes or deviates, thereby reducing or eliminating the risk of developing a tumor in said subject. The method can further comprise altering the level of expression of at least one miRNA, at least two miRNA or at least six miRNA, for which the level of expression changes or deviates, thereby reducing or eliminating the risk of developing an aggressive tumor in said subject. The method can further comprise altering the level of expression of at least one miRNA, at least two miRNA or at least six miRNA, for which the level of expression changes or deviates, thereby treating a tumor in said subject. The method can further comprise altering the level of expression of at least one miRNA, at least two miRNA or at least six miRNA, for which the level of expression changes or deviates, thereby treating an aggressive tumor in said subject.

Preferably, altering the level of expression of said of at least one miRNA, at least two miRNA or at least six miRNA, comprises administering to said subject a therapeutically effective amount of at least one miRNA, at least two miRNA or at least six miRNA, listed in Tables Ia, Ic, IIa, IIc, Va, Vc, VIa, or VIc, or a chemically synthesized miRNA mimetic or recombinant thereof, if the level of expression of said of at least one miRNA, at least two miRNA or at least six miRNA, is lower than the control level of expression or administering to said subject a therapeutically effective amount of a compound capable of inhibiting the expression of at least one miRNA, at least two miRNA or at least six miRNA, listed in Tables Ia, Ic, IIa, IIc, Va, Vc, VIa, or VIc, if the level of expression of said of at least one miRNA, at least two miRNA or at least six miRNA, is higher than the control level of expression.

The method can comprise increasing the level of expression of said at least one miRNA, at least two miRNA or at least six miRNA, which is under-expressed with respect to the control level of expression. The method can comprise administering a therapeutically effective amount of a composition comprising at least one miRNA, at least two miRNA or at least six miRNA listed in Tables Ia, Ic, IIa, IIc, Va, Vc, VIa, or VIc, or a chemically synthesized miRNA mimetic or recombinant thereof. The method can comprise administering a therapeutically effective amount of a composition comprising at least one miRNA, at least two miRNA or at least six miRNA listed in Tables Ib, Id, IIb, IId, Vb, Vd, VIb or VId, or a chemically synthesized miRNA mimetic or recombinant thereof. The method can comprise decreasing the level of expression of said at least one miRNA, at least two miRNA or at least six miRNA, which is over-expressed with respect to the control level of expression. The method can comprise administering a therapeutically effective amount of a composition comprising an inhibitor of at least one miRNA, at least two miRNA or at least six miRNA listed in Tables Ia, Ic, IIa, IIc, Va, Vc, VIa, or VIc. The method can comprise administering a therapeutically effective amount of a composition comprising an inhibitor of at least one miRNA, at least two miRNA or at least six miRNA listed in Tables Ib, Id, IIb, IId, Vb, Vd, VIb or VId. The inhibitor can comprise double-filament RNA, short interfering RNA (siRNA), antisense nucleic acids, anti-miRNA oligonucleotides (AMOs), molecules of enzymatic RNA, or ribozymes.

The present invention also provides pharmaceutical compound comprising at least one miRNA, at least two miRNA or at least six miRNA listed in Tables Ia, Ic, IIa, IIc, Va, Vc, VIa, or VIc, chemically synthesized miRNA mimetic or recombinant thereof, or an inhibitor of the expression of at least one miRNA, at least two miRNA or at least six miRNA listed in Tables Ia, Ic, IIa, IIc, Va, Vc, VIa, or VIc and a pharmaceutically acceptable carrier.

The present invention also provides pharmaceutical compound comprising at least one miRNA, at least two miRNA or at least six miRNA listed in Tables Ib, Id, IIb, IId, Vb, Vd, VIb or VId, chemically synthesized miRNA mimetic or recombinant thereof, or an inhibitor of the expression of at least one miRNA, at least two miRNA or at least six miRNA listed in Tables Ib, Id, IIb, IId, Vb, Vd, VIb or VId and a pharmaceutically acceptable carrier. Preferably, the miRNA are the miRNA listed in Tables Ie, IIe, IIf, IIg, Ve, Vf, VIe or VIf.

The present invention provides a method for treating an individual in whom the presence of a pulmonary tumour has been diagnosed or in whom a risk of developing a pulmonary tumour has been diagnosed, respectively for the treatment of the pulmonary tumour or in order to reduce and/or eliminate the risk of developing a pulmonary tumour.

The method comprises the following steps of measuring an expression level of at least one miRNA, at least two miRNA or at least six miRNA listed in Tables Ia, Ic, IIa, IIc, Va, Vc, VIa, or VIc, present in a sample of biological fluid previously collected from an individual, and then determining the miRNAs having values measured for the expression level which deviate with respect to a predetermined and respective control criterion. The evaluation of the deviation with respect to a control criterion can use the procedures of the miRNA ratios described above for the various cases.

Once the overexpressed or underexpressed miRNAs have been determined, the method comprises altering the expression level of the miRNAs whose levels of expression deviate with respect to the respective control criterion.

For example, in order to alter the expression level of the miRNAs the individual can be administered with a pharmaceutical compound having an effective quantity of at least one miRNA, at least two miRNA or at least six miRNA of the miRNAs listed in Tables Ia, Ic, IIa, IIc, Va, Vc, VIa, or VIc if the expression level measured of the miRNA, or miRNAs, is lower than a respective control expression level.

Alternatively, or in addition to the above, it is also possible to administer the individual with a pharmaceutical compound having an effective quantity of at least a compound for inhibiting the expression of at least one miRNA, at least two miRNA or at least six miRNA listed in Tables Ia, Ic, IIa, IIc, Va, Vc, VIa, or VIc if and for those miRNAs whose measured expression level is above the control expression level.

In this way the values of the expression level can be reset to the control expression level for the underexpressed miRNAs with respect to the respective control level of expression and/or it is possible to reduce the expression level for the overexpressed miRNAs.

With the aim of resetting the level of the underexpressed miRNAs a therapeutically effective quantity of a compound can be administered which comprises at least one miRNA, at least two miRNA or at least six miRNA of the miRNAs of Tables Ia, Ic, IIa, IIc, Va, Vc, VIa, or VIc, chemically synthesized (miRNA mimetics) or recombinant.

With the aim of reducing the expression level values to the control expression level for the overexpressed miRNAs with respect to the respective control expression level, a therapeutically effective quantity of a compound can be administered which comprises at least one miRNA, at least two miRNA or at least six miRNA inhibitor of a microRNA of Tables Ia, Ic, IIa, IIc, Va, Vc, VIa, or VIc. The inhibitor comprises, for example, one or more of the following: double-filament RNA, optionally short interfering RNA (siRNA), antisense nucleic acids (anti-miRNA oligonucleotides (AMOs), molecules of enzymatic RNA (ribozymes). The inhibitor is directed to a specific product of microRNA and interferes with the expression (by inhibition of the translation or induction of the degradation) of a target gene of the microRNA.

The administering of the above compounds (synthetic microRNAs or mimetic miRNAs and inhibitors of microRNA) can for example can be done by means of viral systems or nanoparticles containing microRNA or microRNA inhibitor) linked covalently with lipids or encapsulated liposomes.

The compounds can be administered by any means known in the art, including but not limited to, intranasal instillation, inhalation (aerosol), systemic administration (injection or infusion), direct inoculation in the tumour (where present and visible), intrapleural administration, endopleuric administration or a combination thereof.

In terms of dosage, continuous and prolonged dosage can be performed over time. As miRNA molecules are "naturally" present in the organism, no relevant toxicity will obtain.

Biomarker Apparatuses and Kits

The present invention provides an article comprising a support having a plurality of sites, wherein each site is capable of receiving a quantity of a biological sample, wherein each of the sites comprises at least one reagent capable of binding with at least one miRNA, at least two miRNA or at least six miRNA, listed in Tables Ia, Ic, IIa, IIc, Va, Vc, VIa, or VIc.

The reagent can be selected from group consisting of a polynucleotide comprising a nucleotide sequence of at least one miRNA, at least two miRNA, or at least six miRNA, from the miRNA listed in Tables Ia, Ic, IIa, IIc, Va, Vc, VIa, or VIc; a polynucleotide comprising a nucleotide sequence which is complementary to a sequence of at least one miRNA, at least two miRNA, or at least six miRNA, from the miRNA listed in Tables Ia, Ic, IIa, IIc, Va, Vc, VIa, or VIc; and a molecular probe configured such as to recognize a sequence of at least one miRNA, at least two miRNA, or at least six miRNA, from the miRNA listed in Tables Ia, Ic, IIa, IIc, Va, Vc, VIa, or VIc.

The present invention also provides an article comprising a support having a plurality of sites, wherein each site is capable of receiving a quantity of a biological sample, wherein each of the sites comprises at least one reagent capable of binding with at least one miRNA, at least two miRNA or at least six miRNA, listed in Tables Ib, Id, IIb, IId, Vb, Vd, VIb, or VId. Preferably, the miRNA can be the miRNA listed in Table Ie, IIe, IIf, IIg, Ve, Vf, VIe or VIf.

The present invention also provides an apparatus comprising at least one unit capable of receiving at least one of the articles of the present invention; means for determining the level of expression of at least one miRNA, at least two miRNA or at least six miRNA, listed in Tables Ia, Ic, IIa, IIc, Va, Vc, VIa, or VIc, and means for calculating the real quotients from among the levels of expression of at least one pair, at least two pairs, or at least six pairs, of miRNA from the pairs of miRNA listed in Tables IIIa, IIIc, IVa, IVc, VIIa, VIII, VIIIa, or VIIIc.

The means for determining the value of the level of expression can be selected from the group consisting of Quantitative Real-time PCR, Microfluidic cards, Microarrays, RT-PCR, quantitative or semi-quantitative, Northern blot, Solution Hybridization, and Sequencing.

The present invention provides medical kits useful for effectively and simply applying the methods described above, for determining the risk of contracting a tumour or for tumour diagnosis, for example by using a sample of blood removed from an individual.

In its general form the kit comprises a platform having a plurality of sites, each of which is destined to receive a respective discrete quantity of the sample of biological fluid (for example whole blood, serum, plasma, saliva or bronchial condensate). In the structural sense the platform can be a support for a micro-fluidic card with the miRNA of interest with channellings for the distribution to the respective sites of a predetermined number of samples of biological fluid. Each site comprises a reagent capable of bonding with at least one miRNA, at least two miRNA or at least six miRNA of the microRNAs of Tables Ia, Ic, IIa or IIc for determining the risk of contracting a tumour or a reagent capable of bonding with at least one miRNA, at least two miRNA or at least six miRNA of the microRNAs of Tables Va, Vc, VIa or VIc for tumour diagnosis, in such a way as to enable detectability with the apparatus described herein below.

For example it can include at least one selected from a group comprising: a polynucleotide comprising a nucleotide sequence of at least one miRNA, at least two miRNA or at least six miRNA of the microRNAs as in Tables Ia, Ic, IIa, IIc, Va, Vc, VIa, or VIc, a polynucleotide comprising a nucleotide sequence which is complementary to a sequence of at least one miRNA, at least two miRNA or at least six miRNA of the microRNAs as in Tables Ia, Ic, IIa, IIc, Va, Vc, VIa, or VIc, a molecular probe configured such as to recognize a sequence of at least one miRNA, at least two miRNA or at least six miRNA of the microRNAs as in Tables Ia, Ic, IIa, IIc, Va, Vc, VIa, or VIc.

The described medical kit can also be used with a medical apparatus comprising a unit defining a seating for receiving one or more kits and means for determining the value of the expression of the microRNAs of Tables Ia, Ic, IIa, IIc, Va, Vc, VIa, or VIc. Determining the value of the expression level can be performed by any means known in the art, including but not limited to, Quantitative Real-time PCR, Microfluidic cards, Microarrays, Quantitative or semi-quantitative RT-PCR, Northern blot, Solution Hybridization, Sequencing or combinations thereof.

The apparatus can also exhibit means for calculating the values of the real ratios among values of expression levels of pairs of microRNAs as in Tables IIIa, IIIc, IVa, IVc, VIIa, VIIc, VIIIa, or VIIIc. These means can comprise a programme and a processing unit in which the programme contains instructions which when carried out by the processor enable a calculation of the ratios. Alternatively an analog circuit can be provided which is able to perform the calculations.

miRNA

Overall, 24 miRNAs compose the signature of risk (R), signature of aggressive disease (AR), signature of diagnosis (D) and signature of presence of aggressive disease (AD). Table IX recites those 24 miRNAs and how often they appear as part of a ratio for each signature.

TABLE IX

| miRNA | R | AR | D | AD |
|---|---|---|---|---|
| hsa-miR-16 | 2 | 4 | 0 | 1 |
| hsa-miR-17 | 4 | 4 | 3 | 3 |
| hsa-miR-21 | 0 | 5 | 0 | 1 |
| hsa-miR-101 | 4 | 4 | 2 | 1 |
| hsa-miR-126 | 1 | 1 | 2 | 4 |
| hsa-miR-145 | 0 | 2 | 3 | 1 |
| hsa-miR-197 | 5 | 9 | 6 | 13 |
| hsa-miR-221 | 0 | 2 | 0 | 0 |
| hsa-miR-320 | 1 | 2 | 3 | 0 |
| hsa-miR-451 | 7 | 10 | 0 | 11 |
| hsa-miR-660 | 11 | 0 | 9 | 4 |
| hsa-miR-106a | 3 | 4 | 4 | 3 |
| hsa-miR-133a | 3 | 0 | 0 | 0 |
| hsa-miR-140-3p | 2 | 1 | 0 | 0 |
| hsa-miR-140-5p | 0 | 0 | 2 | 2 |
| hsa-miR-142-3p | 1 | 0 | 3 | 1 |
| hsa-miR-148a | 0 | 1 | 2 | 1 |
| hsa-miR-15b | 3 | 1 | 0 | 1 |
| hsa-miR-19b | 3 | 1 | 2 | 4 |
| hsa-miR-28-3p | 1 | 8 | 4 | 4 |
| hsa-miR-30b | 0 | 2 | 0 | 1 |
| hsa-miR-30c | 0 | 2 | 0 | 1 |
| hsa-miR-486-5p | 0 | 0 | 0 | 6 |
| hsa-miR-92a | 3 | 3 | 9 | 1 |

The present invention provides apparatuses and kits for detecting at least one, at least two, at least three, at least four, at least six or all twenty-four of the miRNA of Table IX. The present invention provides apparatuses and kits for activating or stimulating the activity of or the expression of at least one, at least two, at least three, at least four, at least six or all twenty-four of the miRNA of Table IX. The present invention provides apparatuses and kits for decreasing or inhibiting the activity of or the expression of at least one, at least two, at least three, at least four, at least six or all twenty-four of the miRNA of Table IX. The present invention also provides pharmaceutical compositions for activating or stimulating the activity of or the expression of at least one, at least two, at least three, at least four, at least six or all twenty-four of the miRNA of Table IX. The present invention also provides pharmaceutical compositions for decreasing or inhibiting the activity of or the expression of at least one, at least two, at least three, at least four, at least six or all twenty-four of the miRNA of Table IX.

Table X provides a summary of the miRNA for use in all aspects of the present invention.

TABLE X

| miRNA Name | Sequence |
|---|---|
| hsa-miR-7-2 (pre-miR) | CUGGAUACAGAGUGGACCGGCUGGCCCCAUCUGGAAGACUAGUGA UUUUGUUGUUGUCUUACUGCGCUCAACAACAAAUCCCAGUCUACC UAAUGGUGCCAGCCAUCGCA (SEQ ID NO: 1) |
| hsa-miR-7-2-5p (mature miR 5' arm) | UGGAAGACUAGUGAUUUUGUUGU (SEQ ID NO: 2) |

TABLE X -continued

| miRNA Name | Sequence |
| --- | --- |
| hsa-miR-7-2-3p (mature miR 3' arm) | CAACAAAUCCCAGUCUACCUAA (SEQ ID NO: 3) |
| hsa-miR-15b (pre-miR) | UUGAGGCCUUAAAGUACUGUAGCAGCACAUCAUGGUUUACAUGCU ACAGUCAAGAUGCGAAUCAUUAUUUGCUGCUCUAGAAAUUUAAGG AAAUUCAU (SEQ ID NO: 4) |
| hsa-miR-15b-5p (mature miR 5' arm) | UAGCAGCACAUCAUGGUUUACA (SEQ ID NO: 5) |
| hsa-miR-15b-3p (mature miR 3' arm) | CGAAUCAUUAUUUGCUGCUCUA (SEQ ID NO: 6) |
| hsa-miR-16-1 (pre-miR from Chr. 13) | GUCAGCAGUGCCUUAGCAGCACGUAAAUAUUGGCGUUAAGAUUCU AAAAUUAUCUCCAGUAUUAACUGUGCUGCUGAAGUAAGGUUGAC (SEQ ID NO: 7) |
| hsa-miR-16-2 (pre-miR from Chr. 3) | GUUCCACUCUAGCAGCACGUAAAUAUUGGCGUAGUGAAAUAUAUA UUAAACACCAAUAUUACUGUGCUGCUUUAGUGUGAC (SEQ ID NO: 8) |
| hsa-miR-16-5p (mature miR 5' arm) | UAGCAGCACGUAAAUAUUGGCG (SEQ ID NO: 9) |
| hsa-miR-16-3p (mature miR 3' arm) | CCAAUAUUACUGUGCUGCUUUA (SEQ ID NO: 10) |
| hsa-miR-17 (pre-miR) | GUCAGAAUAAUGUCAAAGUGCUUACAGUGCAGGUAGUGAUAUGUG CAUCUACUGCAGUGAAGGCACUUGUAGCAUUAUGGUGAC (SEQ ID NO: 11) |
| hsa-miR-17-5p (mature miR 5' arm) | CAAAGUGCUUACAGUGCAGGUAG (SEQ ID NO: 12) |
| hsa-miR-17-3p (mature miR 3' arm) | ACUGCAGUGAAGGCACUUGUAG (SEQ ID NO: 13) |
| hsa-miR-19b-1 (pre-miR from Chr. 13) | CACUGUUCUAUGGUUAGUUUUGCAGGUUUGCAUCCAGCUGUGUGA UAUUCUGCUGUGCAAAUCCAUGCAAAACUGACUGUGGUAGUG (SEQ ID NO: 14) |
| hsa-miR-19b-1-5p (mature miR 5' arm from Chr. 13) | AGUUUUGCAGGUUUGCAUCCAGC (SEQ ID NO: 15) |
| hsa-miR-19b-2 (pre-miR from Chr. X) | ACAUUGCUACUUACAAUUAGUUUUGCAGGUUUGCAUUUCAGCGUA UAUAUGUAUAUGUGGCUGUGCAAAUCCAUGCAAAACUGAUUGUGA UAAUGU (SEQ ID NO: 16) |
| hsa-miR-19b-2-5p (mature miR 5' arm from Chr. X) | AGUUUUGCAGGUUUGCAUUUCA (SEQ ID NO: 17) |
| hsa-miR-19b-3p (mature miR 3' arm from Chr. 13 or X) | UGUGCAAAUCCAUGCAAAACUGA (SEQ ID NO: 18) |
| hsa-miR-21 (pre-miR) | UGUCGGGUAGCUUAUCAGACUGAUGUUGACUGUUGAAUCUCAUGG CAACACCAGUCGAUGGGCUGUCUGACA (SEQ ID NO: 19) |
| hsa-miR-21-5p (mature miR 5' arm) | UAGCUUAUCAGACUGAUGUUGA (SEQ ID NO: 20) |
| hsa-miR-21-3p (mature miR 3' arm) | CAACACCAGUCGAUGGGCUGU (SEQ ID NO: 21) |
| hsa-miR-28 (pre-miR) | GGUCCUUGCCCUCAAGGAGCUCACAGUCUAUUGAGUUACCUUUCU GACUUUCCCACUAGAUUGUGAGCUCCUGGAGGGCAGGCACU (SEQ ID NO: 22) |
| hsa-miR-28-5p (mature miR 5' arm) | AAGGAGCUCACAGUCUAUUGAG (SEQ ID NO: 23) |
| hsa-miR-28-3p (mature miR 3' arm) | CACUAGAUUGUGAGCUCCUGGA (SEQ ID NO: 24) |
| hsa-miR-30a (pre-miR) | GCGACUGUAAACAUCCUCGACUGGAAGCUGUGAAGCCACAGAUGG GCUUUCAGUCGGAUGUUUGCAGCUGC (SEQ ID NO: 25) |

TABLE X -continued

| miRNA Name | Sequence |
|---|---|
| hsa-miR-30a-5p (mature miR 5' arm) | UGUAAACAUCCUCGACUGGAAG (SEQ ID NO: 26) |
| hsa-miR-30a-3p (mature miR 3' arm) | CUUUCAGUCGGAUGUUUGCAGC (SEQ ID NO: 27) |
| hsa-miR-30b (pre-miR) | ACCAAGUUUCAGUUCAUGUAAACAUCCUACACUCAGCUGUAAUAC AUGGAUUGGCUGGGAGGUGGAUGUUUACUUCAGCUGACUUGGA (SEQ ID NO: 28) |
| hsa-miR-30b-5p (mature miR 5' arm) | UGUAAACAUCCUACACUCAGCU (SEQ ID NO: 29) |
| hsa-miR-30b-3p (mature miR 3' arm) | CUGGGAGGUGGAUGUUUACUUC (SEQ ID NO: 30) |
| hsa-miR-30c-1 (pre-miR from Chr. 1) | ACCAUGCUGUAGUGUGUGUAAACAUCCUACACUCUCAGCUGUGAG CUCAAGGUGGCUGGGAGAGGGUUGUUUACUCCUUCUGCCAUGGA (SEQ ID NO: 31) |
| hsa-miR-30c-1-3p (mature miR 3' arm from Chr. 1) | CUGGGAGAGGGUUGUUUACUCC (SEQ ID NO: 32) |
| hsa-miR-30c-2 (pre-miR from Chr. 6) | AGAUACUGUAAACAUCCUACACUCUCAGCUGUGGAAAGUAAGAAA GCUGGGAGAAGGCUGUUUACUCUUUCU (SEQ ID NO: 33) |
| hsa-miR-30c-5p (mature miR 5' arm from Chr. 1 or 6) | UGUAAACAUCCUACACUCUCAGC (SEQ ID NO: 34) |
| hsa-miR-30c-2-3p (mature miR 3' arm from Chr. 6) | CUGGGAGAAGGCUGUUUACUCU (SEQ ID NO: 35) |
| hsa-miR-30d (pre-miR) | GUUGUUGUAAACAUCCCCGACUGGAAGCUGUAAGACACAGCUAAG CUUUCAGUCAGAUGUUUGCUGCUAC (SEQ ID NO: 36) |
| hsa-miR-30d-5p (mature miR 5' arm) | UGUAAACAUCCCCGACUGGAAG (SEQ ID NO: 37) |
| hsa-miR-30d-3p (mature miR 3' arm) | CUUUCAGUCAGAUGUUUGCUGC (SEQ ID NO: 38) |
| hsa-miR-34b (pre-miR) | GUGCUCGGUUUGUAGGCAGUGUCAUUAGCUGAUUGUACUGUGGUG GUUACAAUCACUAACUCCACUGCCAUCAAAACAAGGCAC (SEQ ID NO: 39) |
| hsa-miR-34b-5p (mature miR 5' arm) | UAGGCAGUGUCAUUAGCUGAUUG (SEQ ID NO: 40) |
| hsa-miR-34b-3p (mature miR 3' arm) | CAAUCACUAACUCCACUGCCAU (SEQ ID NO: 41) |
| hsa-mirR-92a-1 (pre-miR from Chr. 13) | CUUUCUACACAGGUUGGGAUCGGUUGCAAUGCUGUGUUUCUGUAU GGUAUUGCACUUGUCCCGGCCUGUUGAGUUUGG (SEQ ID NO: 42) |
| hsa-miR-92a-1-5p (mature miR 5' arm from Chr. 13) | AGGUUGGGAUCGGUUGCAAUGCU (SEQ ID NO: 43) |
| hsa-miR-92a-3p (mature miR 3' arm from Chr. 13 or X) | UAUUGCACUUGUCCCGGCCUGU (SEQ ID NO: 44) |
| hsa-miR-92a-2 (pre-miR from Chr. X) | UCAUCCCUGGGUGGGGAUUUGUUGCAUUACUUGUGUUCUAUAUAA AGUAUUGCACUUGUCCCGGCCUGUGGAAGA (SEQ ID NO: 45) |
| hsa-miR-92a-2-5p (mature miR 5' arm from Chr. X) | GGGUGGGGAUUUGUUGCAUUAC (SEQ ID NO: 46) |
| hsa-miR-101-1 (pre-miR from Chr. 1) | UGCCCUGGCUCAGUUAUCACAGUGCUGAUGCUGUCUAUUCUAAAG GUACAGUACUGUGAUAACUGAAGGAUGGCA (SEQ ID NO: 47) |

TABLE X -continued

| miRNA Name | Sequence |
|---|---|
| hsa-miR-101-5p (mature miR 5' arm from Chr. 1 or 9) | CAGUUAUCACAGUGCUGAUGCU (SEQ ID NO: 48) |
| hsa-miR-101-1-3p (mature miR 3' arm from Chr. 1) | UACAGUACUGUGAUAACUGAA (SEQ ID NO: 49) |
| hsa-miR-101-2 (pre-miR from Chr. 9) | ACUGUCCUUUUUCGGUUAUCAUGGUACCGAUGCUGUAUAUCUGAA AGGUACAGUACUGUGAUAACUGAAGAAUGGUGGU (SEQ ID NO: 50) |
| hsa-miR-101-2-3p (mature miR 3' arm from Chr. 9) | UACAGUACUGUGAUAACUGAA (SEQ ID NO: 51) |
| hsa-miR-106a (pre-miR) | CCUUGGCCAUGUAAAAGUGCUUACAGUGCAGGUAGCUUUUUGAGA UCUACUGCAAUGUAAGCACUUCUUACAUUACCAUGG (SEQ ID NO: 52) |
| hsa-miR-106a-5p (mature miR 5' arm) | AAAAGUGCUUACAGUGCAGGUAG (SEQ ID NO: 53) |
| hsa-miR 106a-3p (mature miR 3' arm) | CUGCAAUGUAAGCACUUCUUAC (SEQ ID NO: 54) |
| hsa-miR-126 (pre-miR) | CGCUGGCGACGGGACAUUAUUACUUUUGGUACGCGCUGUGACACU UCAAACUCGUACCGUGAGUAAUAAUGCGCCGUCCACGGCA (SEQ ID NO: 55) |
| hsa-miR-126-5p (mature miR 5' arm) | CAUUAUUACUUUUGGUACGCG (SEQ ID NO: 56) |
| hsa-miR-126-3p (mature miR 3' arm) | UCGUACCGUGAGUAAUAAUGCG (SEQ ID NO: 57) |
| hsa-miR-133a-1 (pre-miR from Chr. 18) | ACAAUGCUUUGCUAGAGCUGGUAAAAUGGAACCAAAUCGCCUCUU CAAUGGAUUUGGUCCCCUUCAACCAGCUGUAGCUAUGCAUUGA (SEQ ID NO: 58) |
| hsa-miR 133a-2 (pre-miR from Chr. 20) | GGGAGCCAAAUGCUUUGCUAGAGCUGGUAAAAUGGAACCAAAUCG ACUGUCCAAUGGAUUUGGUCCCCUUCAACCAGCUGUAGCUGUGCA UUGAUGGCGCCG (SEQ ID NO: 59) |
| hsa-miR-133a (mature miR 3' arm from Chr. 18 or 20) | UUUGGUCCCCUUCAACCAGCUG (SEQ ID NO: 60) |
| hsa-miR-140 (pre-miR) | UGUGUCUCUCUCUGUGUCCUGCCAGUGGUUUUACCCUAUGGUAGG UUACGUCAUGCUGUUCUACCACAGGGUAGAACCACGGACAGGAUA CCGGGGCACC (SEQ ID NO: 61) |
| hsa-miR-140-5p (mature miR 5' arm) | CAGUGGUUUUACCCUAUGGUAG (SEQ ID NO: 62) |
| hsa-miR-140-3p (mature miR 3' arm) | UACCACAGGGUAGAACCACGG (SEQ ID NO: 63) |
| hsa-miR-142 (pre-miR) | GACAGUGCAGUCACCCAUAAAGUAGAAAGCACUACUAACAGCACU GGAGGGUGUAGUGUUUCCUACUUUAUGGAUGAGUGUACUGUG (SEQ ID NO: 64) |
| hsa-miR-142-5p (mature miR 5' arm) | CAUAAAGUAGAAAGCACUACU (SEQ ID NO: 65) |
| hsa-miR-142-3p (mature miR 3' arm) | UGUAGUGUUUCCUACUUUAUGGA (SEQ ID NO: 66) |
| hsa-miR-144 (pre-miR) | UGGGGCCCUGGCUGGGAUAUCAUCAUAUACUGUAAGUUUGCGAUG AGACACUACAGUAUAGAUGAUGUACUAGUCCGGGCACCCCC (SEQ ID NO: 67) |
| hsa-miR-144-5p (mature miR 5' arm) | GGAUAUCAUCAUAUACUGUAAG (SEQ ID NO: 68) |
| hsa-miR-144-3p (mature miR 3' arm) | UACAGUAUAGAUGAUGUACU (SEQ ID NO: 69) |

TABLE X -continued

| miRNA Name | Sequence |
|---|---|
| hsa-miR-145 (pre-miR) | CACCUUGUCCUCACGGUCCAGUUUUCCCAGGAAUCCCUUAGAUGC UAAGAUGGGGAUUCCUGGAAAUACUGUUCUUGAGGUCAUGGUU (SEQ ID NO: 70) |
| hsa-miR-145-5p (mature miR 5' arm) | GUCCAGUUUUCCCAGGAAUCCCU (SEQ ID NO: 71) |
| hsa-miR-145-3p (mature miR 3' arm) | GGAUUCCUGGAAAUACUGUUCU (SEQ ID NO: 72) |
| hsa-miR-148a (pre-miR) | GAGGCAAAGUUCUGAGACACUCCGACUCUGAGUAUGAUAGAAGUC AGUGCACUACAGAACUUUGUCUC (SEQ ID NO: 73) |
| hsa-miR-148a-5p (mature miR 5' arm) | AAAGUUCUGAGACACUCCGACU (SEQ ID NO: 74) |
| hsa-miR-148a-3p (mature miR 3' arm) | UCAGUGCACUACAGAACUUUGU (SEQ ID NO: 75) |
| hsa-miR-197 (pre-miR) | GGCUGUGCCGGGUAGAGAGGGCAGUGGGAGGUAAGAGCUCUUCAC CCUUCACCACCUUCUCCACCCAGCAUGGCC (SEQ ID NO: 76) |
| hsa-miR-197-5p (mature miR 5' arm) | CGGGUAGAGAGGGCAGUGGGAGG (SEQ ID NO: 77) |
| hsa-miR-197-3p (mature miR 3' arm) | UUCACCACCUUCUCCACCCAGC (SEQ ID NO: 78) |
| hsa-miR-200b (pre miR) | CCAGCUCGGGCAGCCGUGGCCAUCUUACUGGGCAGCAUUGGAUGG AGUCAGGUCUCUAAUACUGCCUGGUAAUGAUGACGGCGGAGCCCU GCACG (SEQ ID NO: 79) |
| hsa-miR-200b-5p (mature miR 5' arm) | CAUCUUACUGGGCAGCAUUGGA (SEQ ID NO: 80) |
| hsa-miR-200b-3p (mature miR 3' arm) | UAAUACUGCCUGGUAAUGAUGA (SEQ ID NO: 81) |
| hsa-miR-205 (pre-miR) | AAAGAUCCUCAGACAAUCCAUGUGCUUCUCUUGUCCUUCAUUCCA CCGGAGUCUGUCUCAUACCCAACCAGAUUUCAGUGGAGUGAAGUU CAGGAGGCAUGGAGCUGACA (SEQ ID NO: 82) |
| hsa-miR-205-5p (mature miR 5' arm) | UCCUUCAUUCCACCGGAGUCUG (SEQ ID NO: 83) |
| hsa-miR-205-3p (mature miR 3' arm) | GAUUUCAGUGGAGUGAAGUUC (SEQ ID NO: 84) |
| hsa-miR-210 (pre-miR) | ACCCGGCAGUGCCUCCAGGCGCAGGGCAGCCCCUGCCCACCGCAC ACUGCGCUGCCCCAGACCCACUGUGCGUGUGACAGCGGCUGAUCU GUGCCUGGGCAGCGCGACCC (SEQ ID NO: 85) |
| hsa-miR-210 (mature miR) | CUGUGCGUGUGACAGCGGCUGA (SEQ ID NO: 86) |
| hsa-miR-219-1 (pre-miR) | CCGCCCCGGGCCGCGGCUCCUGAUUGUCCAAACGCAAUUCUCGAG UCUAUGGCUCCGGCCGAGAGUUGAGUCUGGACGUCCCGAGCCGCC GCCCCCAAACCUCGAGCGGG (SEQ ID NO: 87) |
| hsa-miR-219-1-5p (mature miR 5' arm) | UGAUUGUCCAAACGCAAUUCU (SEQ ID NO: 88) |
| hsa-miR-219-1-3p (mature miR 3' arm) | AGAGUUGAGUCUGGACGUCCCG (SEQ ID NO: 89) |
| hsa-miR-221 (pre-miR) | UGAACAUCCAGGUCUGGGGCAUGAACCUGGCAUACAAUGUAGAUU UCUGUGUUCGUUAGGCAACAGCUACAUUGUCUGCUGGGUUUCAGG CUACCUGGAAACAUGUUCUC (SEQ ID NO: 90) |
| hsa-miR-221-5p (mature miR 5' arm) | ACCUGGCAUACAAUGUAGAUUU (SEQ ID NO: 91) |
| hsa-miR-221-3p (mature miR 3' arm) | AGCUACAUUGUCUGCUGGGUUUC (SEQ ID NO: 92) |
| hsa-miR-320a (pre-miR) | GCUUCGCUCCCCUCCGCCUUCUCUUCCCGGUUCUUCCCGGAGUCG GGAAAAGCUGGGUUGAGAGGGCGAAAAAGGAUGAGGU (SEQ ID NO: 93) |

TABLE X -continued

| miRNA Name | Sequence |
| --- | --- |
| hsa-miR-320a (mature miR) | AAAAGCUGGGUUGAGAGGGCGA (SEQ ID NO: 94) |
| hsa-miR-320b-1 (pre-miR from Chr. 1: 117214371-117214449) | AAUUAAUCCCUCUCUUUCUAGUUCUUCCUAGAGUGAGGAAAAGCU GGGUUGAGAGGGCAAACAAAUUAACUAAUUAAUU (SEQ ID NO: 95) |
| hsa-miR-320b-2 (pre-miR from Chr. 1: 224444706-224444843) | UGUUAUUUUUGUCUUCUACCUAAGAAUUCUGUCUCUUAGGCUUU CUCUUCCCAGAUUUCCCAAAGUUGGGAAAAGCUGGGUUGAGAGGG CAAAAGGAAAAAAAAAGAAUUCUGUCUCUGACAUAAUUAGAUAGG GAA (SEQ ID NO: 96) |
| hsa-miR-320b (mature miR from Chr. 1) | AAAAGCUGGGUUGAGAGGGCAA (SEQ ID NO: 97) |
| hsa-miR-320c-1 (pre-miR from Chr. 18: 19263471-19263558) | UUUGCAUUAAAAAUGAGGCCUUCUCUUCCCAGUUCUUCCCAGAGU CAGGAAAAGCUGGGUUGAGAGGGUAGAAAAAAAAUGAUGUAGG (SEQ ID NO: 98) |
| hsa-miR-320c-2 (pre-miR from Chr. 18- 21901650-21901699) | CUUCUCUUUCCAGUUCUUCCCAGAAUUGGGAAAAGCUGGGUUGAG AGGGU (SEQ ID NO: 99) |
| hsa-miR-320-c (mature miR from either Chr 18 loci) | AAAAGCUGGGUUGAGAGGGU (SEQ ID NO: 100) |
| hsa-miR-320d-1 (pre-miR from Chr. 13) | UUCUCGUCCCAGUUCUUCCCAAAGUUGAGAAAAGCUGGGUUGAGA GGA (SEQ ID NO: 101) |
| hsa-miR-320d-2 (pre-miR from Chr. X) | UUCUCUUCCCAGUUCUUCUUGGAGUCAGGAAAAGCUGGGUUGAGA GGA (SEQ ID NO: 102) |
| hsa-miR-320d (mature miR from Chr. 13 or X) | AAAAGCUGGGUUGAGAGGA (SEQ ID NO: 103) |
| hsa-miR-320e (pre-miR) | GCCUUCUCUUCCCAGUUCUUCCUGGAGUCGGGGAAAAGCUGGGUU GAGAAGGU (SEQ ID NO: 104) |
| hsa-miR-320e (mature miR) | AAAGCUGGGUUGAGAAGG (SEQ ID NO: 105) |
| hsa-miR-324 (pre-miR) | CUGACUAUGCCUCCCCGCAUCCCCUAGGGCAUUGGUGUAAAGCUG GAGACCCACUGCCCCAGGUGCUGCUGGGGGUUGUAGUC (SEQ ID NO: 106) |
| hsa-miR-324 (mature miR 5' arm) | CGCAUCCCCUAGGGCAUUGGUGU (SEQ ID NO: 107) |
| hsa-miR-324 (mature miR 3' arm) | ACUGCCCCAGGUGCUGCUGG (SEQ ID NO: 108) |
| hsa-miR-429 (pre-miR) | CGCCGGCCGAUGGGCGUCUUACCAGACAUGGUUAGACCUGGCCCU CUGUCUAAUACUGUCUGGUAAAACCGUCCAUCCGCUGC (SEQ ID NO: 109) |
| hsa-miR-429 (mature miR) | UAAUACUGUCUGGUAAAACCGU (SEQ ID NO: 110) |
| hsa-miR-451a (pre-miR) | CUUGGGAAUGGCAAGGAAACCGUUACCAUUACUGAGUUUAGUAAU GGUAAUGGUUCUCUUGCUAUACCCAGA (SEQ ID NO: 111) |
| hsa-miR-451a (mature miR) | AAACCGUUACCAUUACUGAGUU (SEQ ID NO: 112) |
| hsa-miR-451b (pre-miR) | UGGGUAUAGCAAGAGAACCAUUACCAUUACUAAACUCAGUAAUGG UAACGGUUUCCUUGCCAUUCCCA (SEQ ID NO: 113) |
| hsa-miR-451b (mature miR) | UAGCAAGAGAACCAUUACCAUU (SEQ ID NO: 114) |
| hsa-miR-486 (pre-miRNA) | GCAUCCUGUACUGAGCUGCCCCGAGGCCCUUCAUGCUGCCCAGCU CGGGGCAGCUCAGUACAGGAUAC (SEQ ID NO: 115) |
| hsa-miR-486-5p (mature miR 5' arm) | UCCUGUACUGAGCUGCCCCGAG (SEQ ID NO: 116) |

TABLE X -continued

| miRNA Name | Sequence |
|---|---|
| hsa-miR-486-3p (mature miR 3' arm) | CGGGGCAGCUCAGUACAGGAU (SEQ ID NO: 117) |
| hsa-miR-518e (pre-miR) | UCUCAGGCUGUGACCCUCUAGAGGGAAGCGCUUUCUGUUGGCUAA AAGAAAAGAAAGCGCUUCCCUUCAGAGUGUUAACGCUUUGAGA (SEQ ID NO: 118) |
| hsa-miR-518e 5p (mature miR 5' arm) | CUCUAGAGGGAAGCGCUUUCUG (SEQ ID NO: 119) |
| hsa-miR-518e-3p (mature miR 3' arm) | AAAGCGCUUCCCUUCAGAGUG (SEQ ID NO: 120) |
| hsa-miR-660 (pre-miR) | CUGCUCCUUCUCCCAUACCCAUUGCAUAUCGGAGUUGUGAAUUCU CAAAACACCUCCUGUGUGCAUGGAUUACAGGAGGGUGAGCCUUGU CAUCGUG (SEQ ID NO: 121) |
| hsa-miR-660-5p (mature miR 5' arm) | UACCCAUUGCAUAUCGGAGUUG (SEQ ID NO: 122) |
| hsa-miR-660-3p (mature miR 3' arm) | ACCUCCUGUGUGCAUGGAUUA (SEQ ID NO: 123) |

Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

EXAMPLES

Example 1

Studies, Materials & Methods

The present invention investigated the expression profile of miRNA in the plasma of individuals enrolled in screening protocols using spiral CT. This investigation was done with the aim of verifying the capability of miRNAs as a new class of biomolecular markers for: prediction of the risk of developing a tumour, in particular a pulmonary tumour, and diagnosis of the tumour, in particular pulmonary tumour, and thus as a prognostic aid for discriminating patients with indolent or aggressive pulmonary lesions.

Plasma samples taken from smoker individuals were used, where the individuals were over 50 years old, in a time parameter of between one and two years before detection with CT spiral of the presence of a pulmonary tumour in the same individuals. Also used were samples of plasma collected at the moment of the appearance of the disease (detected using spiral CT). The plasma samples were obtained from patients who had developed a pulmonary tumour with various characteristics in terms of clinical aggressiveness (indolent nodules or advanced and metastatic tumours) as well as from individuals who remained free of disease for the whole duration of the screening.

In a first stage of the research, identification was made of the microRNAs that were present in the plasma using microfluidic cards, model: TaqMan® of Applied Biosystems. Out of 378 microRNA analysed, 100 were present stably in the plasma of healthy smoker individuals used as the control group. Thus, with a large amount of starting data, there is a general agreement on the possibility of normalizing the expression levels of the single microRNAs on the mean of the expression levels of the 100 microRNAs for each individual (Mestdagh P et al. *Genome Biol*, 2009). The data obtained using this type of normalization were compared to those obtained by normalizing on potential microRNA housekeeping (for example mir-16, mammU6, RNU44 or RNU48).

The inventors then thought of no longer using the values of the expression levels of the single microRNAs, but instead the ratios among pairs thereof. The value of the cycle threshold (Ct) obtained by qReal-Time PCR with the SDS 2.2.2® software (Applied Biosystems) was transformed into the corresponding expression value ($2^{-Ct}$). Then the ratio between the value of the expression level of each pair of microRNAs possible was calculated, obtaining 4950 total ratios: the 4950 total ratios were given by the formula 100*99/2 as the ratio between two miRNAs and the reciprocal contain the same data. Finally the variation of these ratios (called "miRNA ratios") in the plasma of the various classes of patients was analysed in order to identify plasma biomarkers.

The results showed that the microRNAs present in the greatest amount in the ratios discriminating among the classes of patients are the same as those which emerge from the analyses performed by normalizing on the mean value of the expression levels of the 100 microRNAs for each individual, thus validating the method based on the miRNA ratios for quantifying the involved microRNAs.

In greater detail, with the aim of identifying biomarkers in the plasma which are able to predict the appearance of the pulmonary tumour, the inventors studied the expression profile of microRNAs circulating in collected samples up to two years preceding the diagnosis of the disease and at the moment of surgery in patients of two independent clinical trials, as mentioned above, for early diagnosis of pulmonary tumour in high-risk individuals (age>50 years and smokers) using spiral CT. In the first training set, made up of 40 samples of plasma from 19 patients and 27 samples of plasma from healthy control individuals in 5 different pools, the miRNA expression levels were analysed using TaqMan MicroRNA Assays (Applied Biosystems) with the aim of identifying the significantly-different miRNA ratios (p<0.05) between samples of plasma collected pre-disease, at the moment of surgery and from healthy individuals.

The specificity and sensitivity of the signatures of microRNAs thus obtained were compared with the validation set composed, as described above, of 32 plasma samples of 22 patients and 54 plasma samples of healthy control individuals, grouped in 10 different pools.

For the generalization of the signatures used for predicting the aggressiveness of the disease, the inventors grouped the two cohorts (training set and validation set) with the aim of obtaining a sufficient number for the statistical analysis. The cases with unfavorable prognosis were first compared to the respective controls and the signatures thus obtained were tested to evaluate their effective capacity to discriminate the patients having poor prognosis from those having good prognosis.

As already mentioned, the signatures of the microRNAs identified in the various analyses were validated on two independent sets constituted by high-risk individuals (smokers of more than 50 years of age) enrolled in two different clinical trials for early identification of pulmonary tumour using low-dose spiral CT: a first set, or training set, made up of 40 samples of plasma from 19 patients and 27 samples of plasma from healthy control individuals grouped in 5 different pools and a second set or validation set (i.e. in a second set of individuals) made up of 32 samples of plasma from 22 patients and 54 plasma samples from healthy control individuals, grouped in 10 different pools.

FIG. 1 summarizes the pathological clinical characteristics of the training set and the validation set selected for the analysis of the expression levels of the miRNAs in the plasma samples.

To determine the microRNA profile in the plasma samples the total RNA was extracted from 200 µl of plasma using the mirVana™ PARIS™ Kit (Ambion), eluting in 50 µl of elution buffer.

The expression levels were determined using q-Real Time PCR starting from 3 µl of elute first using the Megaplex™ Pools Protocol on a microfluidic card, type A (Applied Biosystems), then the Multiplex™ Pools Protocol (Applied Biosystems).

All the data was extrapolated using the Sequence Detection System software (SDS 2.2.2® Applied Biosystems), setting the threshold manually at 0.2 and the baseline between 3 and 18 cycles (on a total of 40).

Apart from the standard equipment for molecular biology, use was made of Real-time quantitative PCR 7900-HT (Applied Biosystems) and GeneAmp© 9700 Sequence Detection System (Applied Biosystems).

Identification of a Signature Based on miRNAs Able to Identify Individuals at Risk of Developing Pulmonary Tumour The samples of plasma collected 1-2 years before from patients in whom a tumour was later diagnosed using spiral CT were analysed and compared with the control pool, constituted by healthy individuals.

A signature was therefore identified in the training comprising 14 miRNA ratios made up of 14 microRNAs capable of correctly discriminating 18 out of 20 pre-disease samples from individuals who then will develop the disease (90% sensitivity), while only one control pool was positive for this signature (80% specificity). In the validation set the sensitivity was 80%, while the specificity was 90% (AUC-ROC=0.85, p<0.001).

Figure 4:
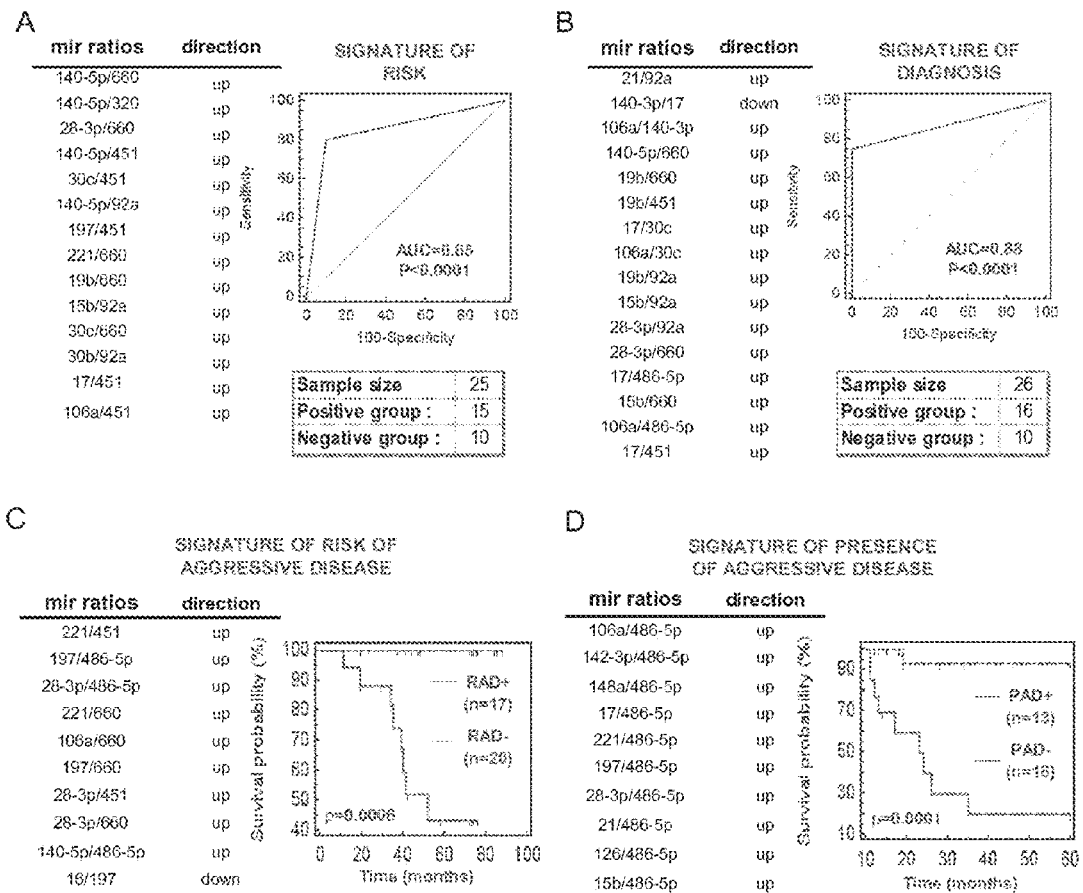
FIG. 4 is a series of ratios and graphs showing miRNA expression analyses in plasma samples collected before the onset and at the time of disease. The signatures of miRNA ratios and their direction in the analyses are listed in the tables. Panel A shows miRNA signature of risk to develop lung cancer. Panel B shows miRNA signature of lung cancer diagnosis. The ROC curves of samples belonging to the validation set are shown. Panel C shows Kaplan-Meier survival curves of patients with miRNA signatures of risk of aggressive disease (RAD) in plasma samples collected 1-2 y before CT-detection of lung cancer. Panel D shows Kaplan-Meier survival curves of patients with miRNA signatures of presence of aggressive disease (PAD) in plasma samples collected at the time of CT-detected lung cancer. The RAD- or PAD-positive patients show a significantly worse survival rate than RAD- or PAD-negative patients (P=0.0006 and P=0.0001, respectively).

The miRNA ratios of the first example were then listed and are reported also in FIG. 4A.

$Q_1$=hsa-mirR-106a/hsa-mirR-451
$Q_2$=hsa-mirR-140-5p/hsa-mirR-320
$Q_3$=hsa-mirR-140-5p/hsa-mirR-451
$Q_4$=hsa-mirR-140-5p/hsa-mirR-660
$Q_5$=hsa-mirR-140-5p/hsa-mirR-92a
$Q_6$=hsa-mirR-15b/hsa-mirR-92a
$Q_7$=hsa-mirR-17/hsa-mirR-451
$Q_8$=hsa-mirR-197/hsa-mirR-451
$Q_9$=hsa-mirR-19b/hsa-mirR-660
$Q_{10}$=hsa-mirR-221/hsa-mirR-660
$Q_{11}$=hsa-mirR-28-3p/hsa-mirR-660
$Q_{12}$=hsa-mirR-30b/hsa-mirR-92a
$Q_{13}$=hsa-mirR-30c/hsa-mirR-451
$Q_{14}$=hsa-mirR-30c/hsa-mirR-660

The predictive capacity of this signature was validated in samples collected up to 28 months before the diagnosis of disease with spiral CT and the microRNAs most frequently deregulated were: mir-660, mir-140-5p, mir-451, mir-28-3p, mir-30c and mir-92.

Identification of the Signature Based on the miRNAs Able to Have Diagnostic Value Plasma samples collected at the moment of surgery or on identification of the disease by spiral CT were compared with the control pools. In the training set, a panel of 16 miRNA ratios, made up of 13 microRNAs, correctly classify 16 out of 19 patients with a sensitivity of 84% and a specificity of 80%. In the validation set sensitivity is 75% and the specificity is 100% (AUC-ROC=0.88, p<0.0001).

A lower sensitivity in the validation set can be correlated to the presence of a greater number of small indolent nodules, of which two patients are part, whose blood samples were mis-matched both by the risk signature in the pre-disease samples, and by the signature in the samples taken in the presence of disease.

The miRNA ratios of the second example are listed herein below and are also reported in FIG. 4B.

$Q_1$=hsa-mirR-106a/hsa-mirR-140-3p
$Q_2$=hsa-mirR-106a/hsa-mirR-30c
$Q_3$=hsa-mirR-106a/hsa-mirR-486-5p
$Q_4$=hsa-mirR-140-3p/hsa-mirR-17
$Q_5$=hsa-mirR-140-5p/hsa-mirR-660
$Q_6$=hsa-mirR-15b/hsa-mirR-660
$Q_7$=hsa-mirR-15b/hsa-mirR-92a
$Q_8$=hsa-mirR-17/hsa-mirR-30c
$Q_9$=hsa-mirR-17/hsa-mirR-451
$Q_{10}$=hsa-mirR-17/hsa-mirR-486-5p
$Q_{11}$=hsa-mirR-19b/hsa-mirR-451
$Q_{12}$=hsa-mirR-19b/hsa-mirR-660
$Q_{13}$=hsa-mirR-19b/hsa-mirR-92a
$Q_{14}$=hsa-mirR-21/hsa-mirR-92a
$Q_{15}$=hsa-mirR-28-3p/hsa-mirR-660
$Q_{16}$=hsa-mirR-28-3p/hsa-mirR-92a This diagnostic signature was then used to verify the presence of disease in the plasma samples collected before identification of the disease by spiral CT. In the training set, 11 out of 20 (55%) of the cases are classified as being in presence of disease and, very interestingly, of these 11, 10 are either pessimistic diagnosis cases or belonging to patients in whom the tumour was identified in the later years of the screening, or where more aggressive tumours with worse prognoses were identified.

Very similar results were obtained in the validation set, since in 10 out of 15 (66.6%) pre-disease samples the signature of the presence of disease was presented. There are only 4 miRNA ratios in common between the risk signatures and the diagnosis signatures; also partially different are the microRNAs involved: mir-17, mir-660, mir-92a, mir-106a, mir-19b are the most deregulated microRNAs at the moment of the diagnosis of pulmonary tumour.

Identification of a Signature Based on the miRNAs for Risk of Development of Aggressive Pulmonary Tumour The microRNA profiles of the pre-disease samples with unfavorable prognosis were identified and 10 miRNA ratios identified that were able to recognize 5 out of 5 patients in the first set, 4 out of 5 in the validation set and with a specificity in both of 100%. Note that mir-221, mir-660, mir-486-5p, mir-28-3p, mir-197, mir-106a, mir-451, mir-140-5p and mir-16 are the deregulated microRNAs.

The miRNA ratios of this third example are listed below and are also reported in FIG. 4C.

$Q_1$=hsa-mirR-106a/hsa-mirR-660
$Q_2$=hsa-mirR-140-5p/hsa-mirR-486-5p
$Q_3$=hsa-mirR-16/hsa-mirR-197
$Q_4$=hsa-mirR-197/hsa-mirR-486-5p
$Q_5$=hsa-mirR-197/hsa-mirR-660
$Q_6$=hsa-mirR-221/hsa-mirR-451
$Q_7$=hsa-mirR-221/hsa-mirR-660
$Q_8$=hsa-mirR-28-3p/hsa-mirR-451
$Q_9$=hsa-mirR-28-3p/hsa-mirR-486-5p
$Q_{10}$=hsa-mirR-28-3p/hsa-mirR-660

This signature was then tested on the pre-disease samples of the patients having a good prognosis in the training set and in the validation set. The signature classifies, respectively in the two sets, 33.3% and 45% of the samples; FIG. 2 illustrates a Kaplan-Meier survival curve of patients with or without the signature of risk of aggressive disease; the curve with the aggressive signature is represented in a continuous line and identified by RAD+ (risk of aggressive disease+) while the curve without the signature of risk of aggressive disease is represented by a discontinuous line and identified by RAD- (risk of aggressive disease-) in plasma samples collected 1-2 years before identification of the disease by spiral CT.

Of interest is the fact that the majority of the identified samples belong to individuals who developed the tumour between the III and the V year of screening, independently of the degree of the tumour. This supports the previous observation on the tumoral and normal samples of lung tissue, where a different profile of microRNA was present respectively in the tumoral and normal tissue of the same patients. It is worthy of note that among the patients having a tumour diagnosed in the second year of screening (all tumours at stage Ia and Ib), only one case with stage Ib exhibited the signature of aggressive risk.

Identification of a Signature Based on miRNAs for Prognosis of Patients Identified by Spiral CT The samples from patients having a pessimistic prognosis, collected at the moment of the diagnosis of the disease, were analysed, revealing a signature of 10 miRNA ratios, all containing mir-486-5p, which identifies 7 out of 8 patients with a pessimistic prognosis in the training set, 2 out of 3 of the validation set and no control pool in either data set.

The miRNA ratios of this fourth example are listed below and are also reported in FIG. 4D.

Figure 3:
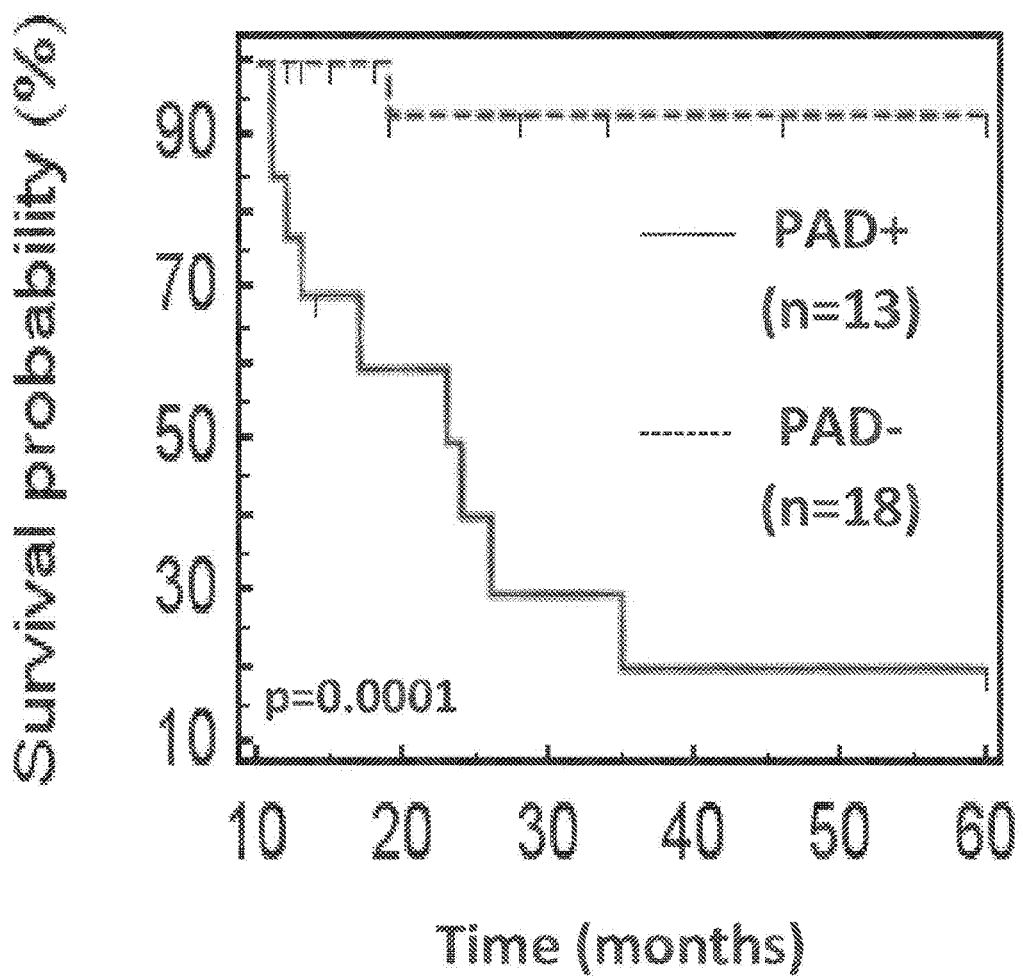
FIG. 3 is a graph showing a Kaplan-Meier survival curve of patients with or without the signatures for presence of aggressive disease.

$Q_1$=hsa-mirR-106a/hsa-mirR-486-5p
$Q_2$=hsa-mirR-126/hsa-mirR-486-5p
$Q_3$=hsa-mirR-142-3p/hsa-mirR-486-5p
$Q_4$=hsa-mirR-148a/hsa-mirR-486-5p
$Q_5$=hsa-mirR-15b/hsa-mirR-486-5p
$Q_6$=hsa-mirR-17/hsa-mirR-486-5p
$Q_7$=hsa-mirR-197/hsa-mirR-486-5p
$Q_8$=hsa-mirR-21/hsa-mirR-486-5p
$Q_9$=hsa-mirR-221/hsa-mirR-486-5p
$Q_{10}$=hsa-mirR-28-3p/hsa-mirR-486-5p Further, only 2 out of 11 and 2 out of 13 patients having a good prognosis, respectively in the first and second set, are positive for this signature. FIG. 3 reports a Kaplan-Meier survival curve of patients with or without the signatures for presence of aggressive disease (respectively identified with the continuous line of PAD+, which stands for the presence of aggressive disease+, and with the broken line of PAD-, standing for the presence of aggressive disease-) in plasma samples collected at the moment of identification of the disease by spiral CT.

Further, this signature was used to classify the pre-disease samples in both data sets. Half of the patients with pessimistic prognosis also present this aggressiveness signature, while for those with good prognosis of the 6 positives for this signature, 5 are tumours identified after the third year of screening.

Note that mir-486-5p, compared with mir-21, mir-126, mir-15b, mir-148a, mir-142-3p, mir-17, mir-197, mir-221, mir-28-3p and mir-106a, is always under-expressed in the plasma of patients with a pessimistic prognosis.

From the above-reported results, the inventors deduced that the microRNAs present in the plasma are useful for identifying the presence of the pulmonary tumour even 1-2 years before detection by spiral CT and further for predicting the development of types of more aggressive pulmonary cancer, indicating the possibility of selecting individuals at high risk on the basis of profiles of circulating microRNA.

Example 2 miRNA Treatment

Figure 9:
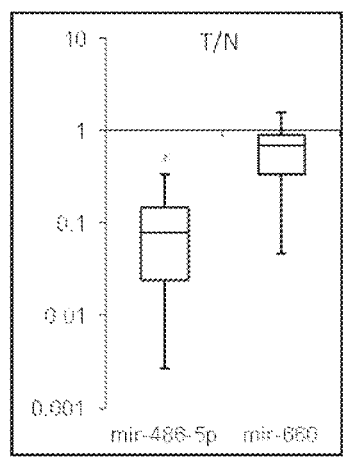
FIG. 9 is a graph showing the expression levels of mir-486-5p and mir-660 in 20 paired tumor and normal lung tissue of the same patients.

The instant example demonstrates modifying the level of two microRNAs of our plasma signatures in a lung cancer cell line (A549). Mir-486 and mir-660 were down-modulated in plasma samples of patients with lung cancer and in particular in those who have developed the aggressive form of the disease. In FIG. 9 microRNA levels were measured by qReal-Time PCR in 20 paired tumor and normal lung tissue of the same patients enrolled in the CT-screening trial used as validation set. Row Ct data were normalized on the housekeeping miRNA RNU6B (DCt). The final expression values were obtained with the formula: $2^{\wedge}(-DCt$ of the tumor tissue)/$2^{\wedge}(-DCt$ of the normal lung). Values>1→upregulated in tumor tissue. Values<1→downregulated in tumor tissue. The results in FIG. 9 show that these two miRNA were downregulated in the tumor tissue compared with the normal lung tissue.

Figure 10:
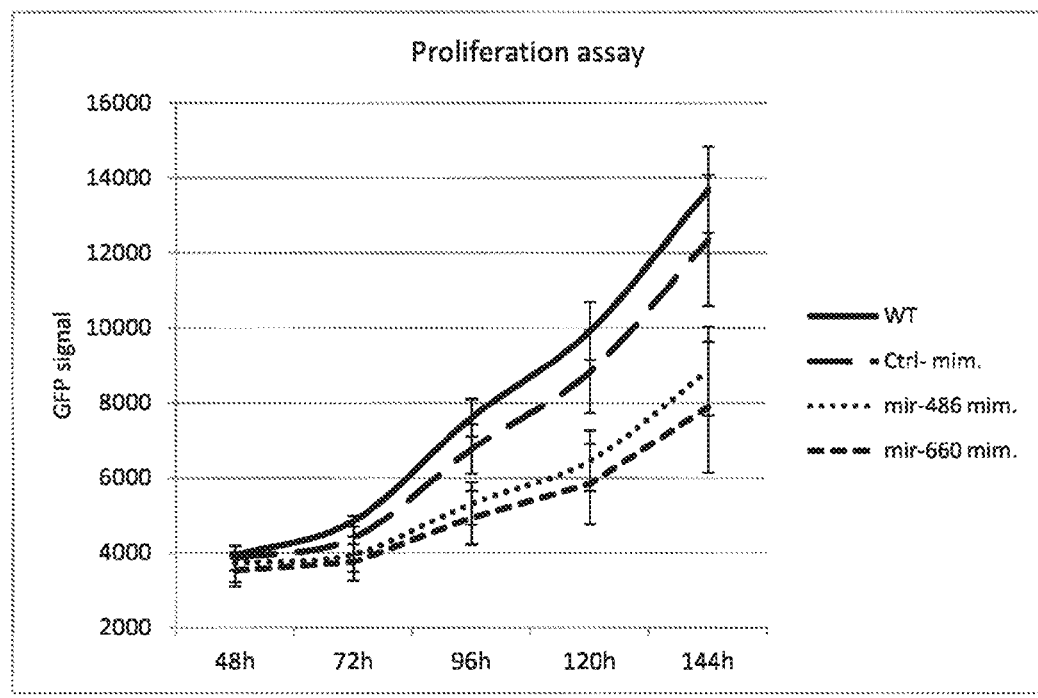
FIG. 10 is a graph showing the results of a proliferation assay performed on A549-GFP cells transfected with the miRNA mimic mir-486-5p and mir-660.

In FIG. 10 mirVana™ miRNA Mimic (Applied biosystem) were used to transfect lung cancer cell line expressing constitutively the Green Fluorescence Protein (A549-GFP), accordingly with the Lipofectamine2000 standard protocol (Invitrogen). 24 h hours after transfection, cells were plated in multiwell plate to assess the proliferation capacity. Real time measurements of the GFP signal were measured every 24 h with a fluorescent multiplate reader (Tecan M1000) using the wavelengths of the GFP. In FIG. 10, 549-GFP transfected with the miRNA mimic mir-486-5p and mir-660 showed a reduced proliferative capacity compared to the wild type and the miRNA mimic scrambled (ctrl-) cell lines.

Figure 11:
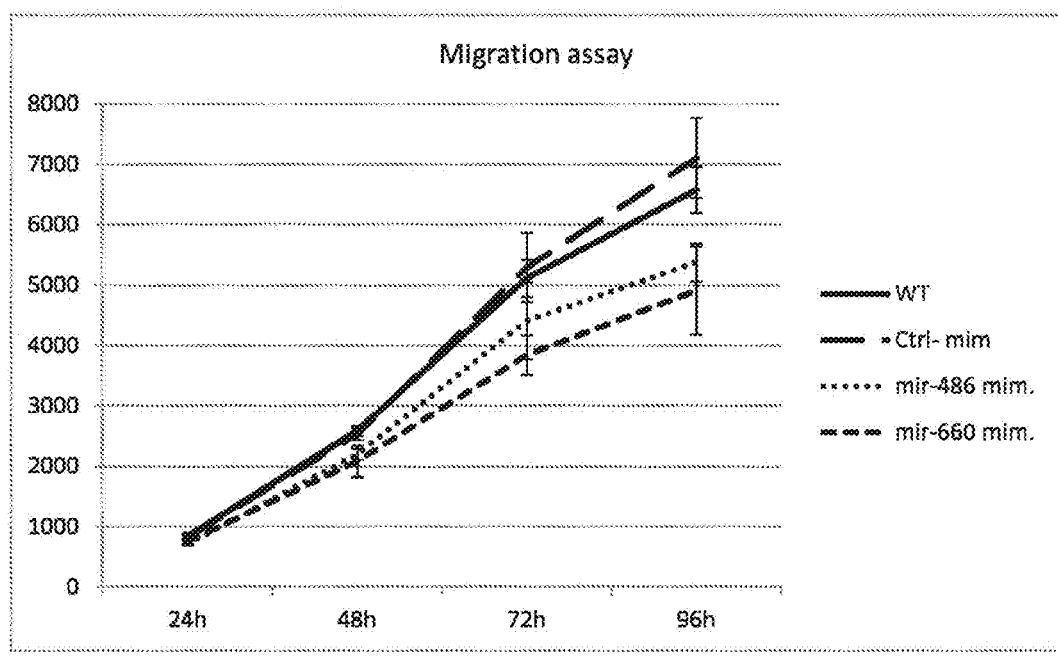
FIG. 11 is a graph showing the results of a migration assay performed on A549-GFP cells transfected with the miRNA mimic mir-486-5p and mir-660.

In FIG. 11, 549-GFP cells were transfected with miRNA mimics as reported before. 24 h hour after transfection cell were plated in Falcon™ FluoroBlok™ Cell Culture Inserts 8.0 µm (BD biosciences) placed in a 24-wells plate. Cell migration capacity was assess measuring GFP signal using the bottom reading tool of the Tecan M1000, in this way it was possible to read just the signal of the cells passed through the membrane of the insert. Real time migration was followed for 4 days. In FIG. 11, 549-GFP transfected with the miRNA mimic mir-486-5p and mir-660 showed a reduced migration capacity compared to the wild type and the miRNA mimic scrambled (ctrl-) cell lines.

Thus, the results show that if these two miRNA were restored in the cancer cell line the proliferation (FIG. 10) and the migration (FIG. 11) capability of cancer cells were significantly reduced. These preliminary results support the idea of using these miRNAs for a putative therapeutic approach.

Example 3

Lung Cancer Detection and Survival

INT-IEO cohort (training set). Lung cancer was diagnosed in 38 subjects, 22 in the first 2 y and 16 from the 3rd to 5th y of screening, including one interval cancer at 4th y. The frequency of stage I was 63% (77% in first 2 y vs. 44% in the last 3 y), and adenocarcinoma was 71% (95% in first 2 y vs. 63% in the last 3 y; Table XI).

TABLE XI

| Characteristic | CT Year | | |
| --- | --- | --- | --- |
|  | 1-2 | 3-5 | Total |
| Lung Cancer | 22 | 16 | 38 |
| Resected | 21 (95) | 12 (75) | 33* (87) |
| Stage I | 17 (77) | 7 (44) | 24 (63) |
| Stage II-IV | 5 (23) | 9 (56) | 14 (37) |
| Adeno | 17 (95) | 10 (63) | 27 (71) |

*28 tumor tissue and 24 normal lung samples were available for miRNA expression analysis. The number in parenthesis is the percent of all detected lung cancers.

Figure 12A:
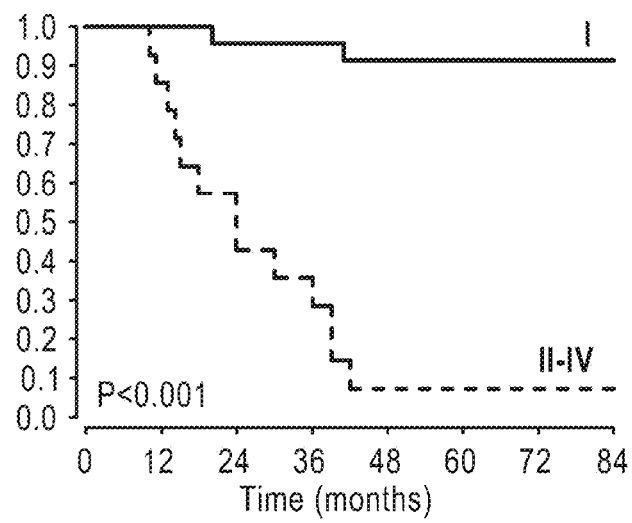
FIGS. 12A and 12B are graphs showing Kaplan-Meier estimates of observed 5-y survival in CT-screening INT-IEO trial.
Figure 12B:
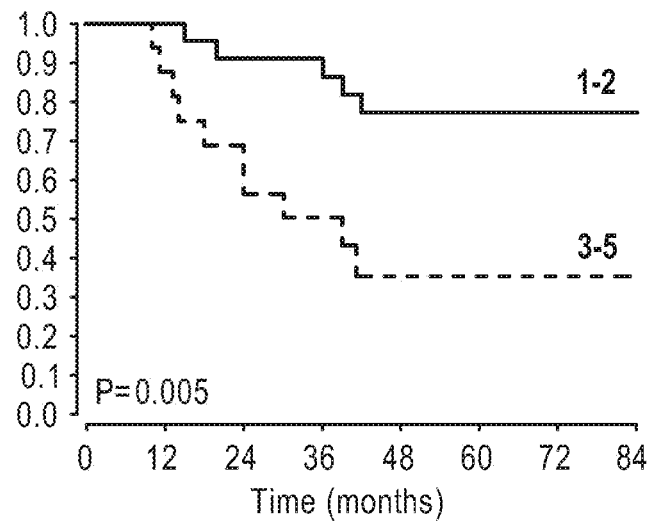

Median follow-up time for the 38 lung cancer cases was 75 mo, with 60% 5-y overall survival (95% C.I.: 43-74%). Five-y overall survival was 92% for stage I and 7% for stages II-IV (P<0.001; FIG. 12A). When the year of detection was considered, 5-y overall survival was 77% for cancers diagnosed in the first 2 y compared with 36% for those detected from 3rd to 5th y of screening (P=0.005; FIG. 12B), indicating that incident cancers represent a more aggressive disease. Year of detection and tumor stage were significantly associated ($\chi^2$ test, P=0.034). In the subset of CT year 1-2/stage I, 5-y survival was 94% (95% C.I.: 65.0-99.1). In the whole group of stage I, after exclusion of one death from second primary lung cancer and one from end-stage chronic obstructive pulmonary disorder (COPD), 5-y survival was 100%.

Multicentric Italian Lung Detection (MILD) cohort (validation set). At the end of 4th year of screening in the MILD trial, lung cancer was diagnosed in 53 subjects, 24 in the first 2 y, and 23 in the 3rd and 4th year. Six interval cancers were diagnosed: one in the 1st y, two in the 2nd y, and three in the 3rd y. Early stage disease (Ia-Ib) was diagnosed in 28 (53%) patients, and adenocarcinoma was diagnosed in 30 (57%) of patients. Because this trial is ongoing, no interim analysis was performed so far. However, even if the median follow-up time of 23 mo is relatively short, we could divide the 53 patients in two groups of reasonable size: 14 patients with poor prognosis (dead or alive with incurable disease) and 39 patients with good prognosis (alive without disease).

miRNA Expression Profiling in Tumor and Normal Lung miRNA profiles of 28 tumors and 24 paired normal lung tissues were analyzed using a miRNA microarray platform. Validation of the differentially expressed miRNAs was done using qRT-PCR.

By class comparison and class prediction analyses (using both paired and unpaired algorithms), expression of 56 miRNAs was significantly different at the nominal 0.001 level of the univariate test. The top 10 deregulated miRNAs that discriminate CT-detected lung cancer from normal lung tissue were: mir-7, mir-21, mir-200b, mir-210, mir-219-1, miR-324 (up-regulated), mir-126, mir-451, mir-30a, and mir-486 (down-regulated; Table XII).

TABLE XII

| miRNAs deregulated | Tumor vs. Normal Tissues | |
| --- | --- | --- |
| (p < 0.001) | Direction | Fold Change |
| mir-7-2-prec | Up | 1.3 |
| mir-126 | Down | 0.4 |
| mir-200b | Up | 1.3 |
| mir-210 | Up | 3.0 |
| mir-219-1 | Up | 1.6 |
| mir-21 | Up | 2.9 |
| mir-324-5p | Up | 1.3 |
| mir-451 | Down | 0.5 |
| mir-486-5p | Down | 0.5 |
| mir-30a | Down | 0.6 |

This list included alterations previously identified in symptomatic lung cancer patients (e.g., mir-21 and the mir-200 family, known to be involved in pathways such as survival, apoptosis, epithelial-mesenchymal transition) and some unidentified changes (e.g., down-regulation of miR-486 and miR-451).

To validate the results obtained with microarray hybridization, the levels of the two most regulated miRNAs (mir-21 and mir-486) were evaluated in tumor and normal samples by qRT-PCR, which confirmed the previous observation.

miRNA Expression in Tissues is Associated with Clinical-Pathological Features

Possible association of miRNA expression profiles with clinical-pathological characteristics of the patients was then investigated (Table XIII). Two miRNAs (mir-205 and mir-21) significantly discriminated adenocarcinoma from squamous cell carcinoma histotypes (P≤0.001). Mir-518e and mir-144 were down-regulated in tumors with a faster growth rate, and higher levels of mir-429, member of the mir-200 family, correlated with a worse disease-free survival (DFS).

TABLE XIII

| Clinical-Pathological Characteristics | Tumor Tissue | | | Normal Tissue | | |
| --- | --- | --- | --- | --- | --- | --- |
|  | miRNA | Direction | P value | miRNA | Direction | P value |
| Histotype (ADC v. SCC or others) | mir-205 | Down | <0.001 |  |  |  |
|  | mir-21-pre | Up | <0.001 |  |  |  |

TABLE XIII-continued

| Clinical-Pathological Characteristics | Tumor Tissue | | | Normal Tissue | | |
|---|---|---|---|---|---|---|
| | miRNA | Direction | P value | miRNA | Direction | P value |
| Growth Rate Diameter (≥50% vs. >50%) | mir-518e | Up | <0.001 | mir-30d* | Up | <0.001 |
| | mir-144-pre | Up | <0.001 | | | |
| Disease-free Survival (Alive vs. Dead or Relapse) | mir-429 | Down | 0.003 | mir-34b | Up | 0.001 |

Figure 13:
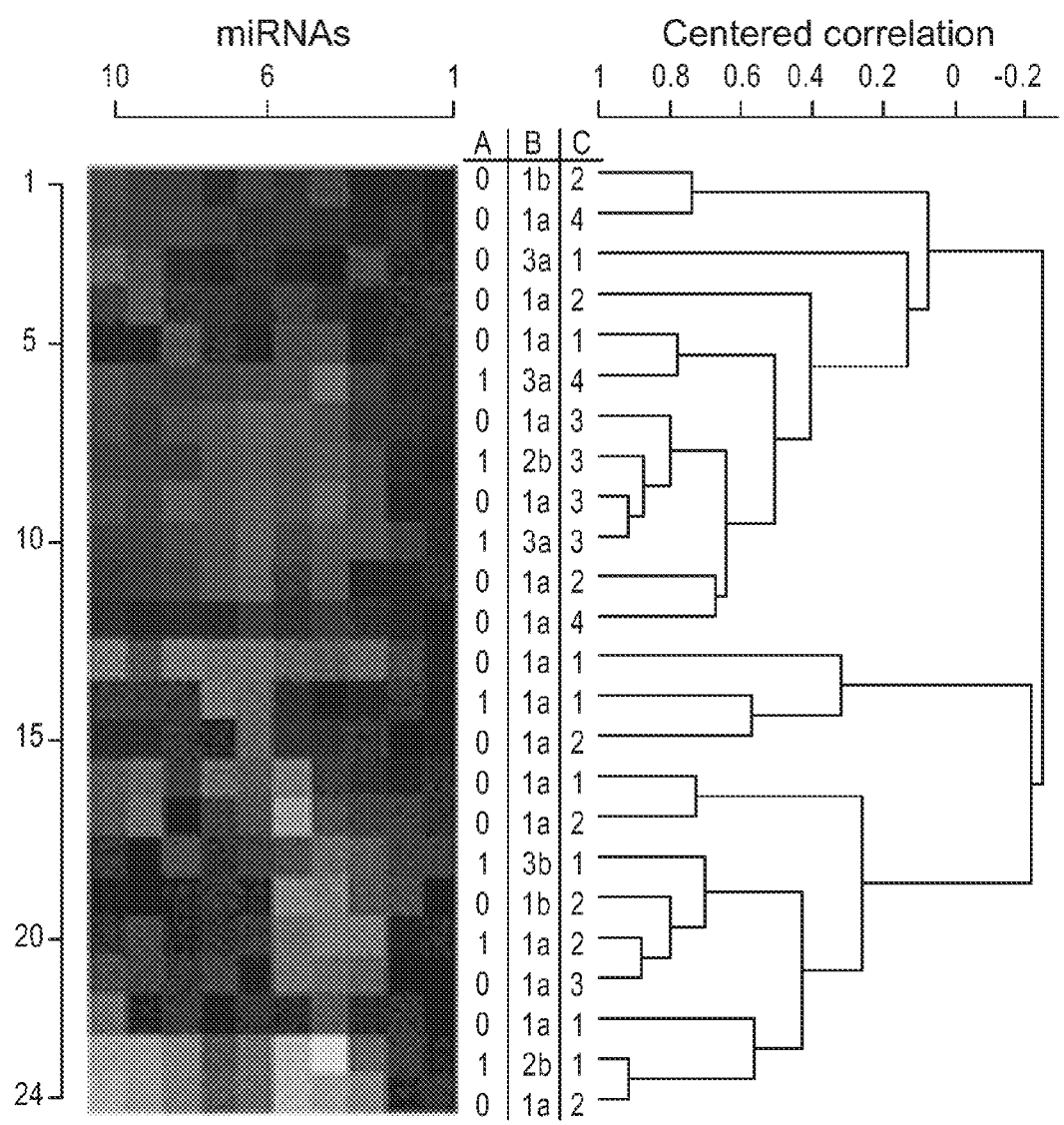
FIG. 13 is an illustration showing clustering analysis on 24 normal lung tissue samples using miRNAs differentially expressed between patients with tumors detected in the first 2 y and those of later years of screening. Clinical status of the patient (0=alive, 1=dead), tumor stage, and year of tumor detection are reported in columns A, B, and C, respectively.

The miRNA expression profile of tumors detected in the first 2 y of the screening was significantly different from the profile of tumors appearing after the 2nd y, with differential expression of eight miRNAs (mir-128, mir-129, mir-369-3p, mir-193, mir-339-3p, mir-185, mir-346, and mir-340). These results indicate that these groups of tumors display different miRNA profiles associated with distinct aggressive features, where the incident tumors grow faster.

miRNA expression analysis on normal lung tissues also discriminated subjects identified in the first 2 y from those of later years of screening (miR-126*, mir-126, let-7c, mir-222, mir-30e, mir-1-2, mir-29b-1, mir-30d-prec, mir-15a, mir-16; FIG. 13). Significant associations were found between miRNAs expression in normal lung and reduction of forced expiratory volume (FEV; mir-379 and mir-29-1*), faster tumor growth (mir-30d*), DFS of the patients (mir-34b; Table XIII). The results obtained by microarray hybridization were independently validated by qRT-PCR.

Although there was no significant difference in smoking habits (packs-per-year, time from smoking cessation), patients detected in years 3-5 showed a higher proportion of severe COPD (GOLD criteria≥2, 33% vs. 5%; $\chi^2$ test, P=0.02).

These findings indicate that specific miRNA signatures in normal lung microenvironment are associated with tumor aggressiveness and clinical history of the patients.

Pathways Enrichment Analysis

For the miRNA signature discriminating tumor from normal samples, pathway enrichment analysis was performed using DIANA-mirPath software on the gene targets predicted by microT-4.0, Pic-Tar, and TargetScan-5. This analysis showed that many of the predicted miRNA targets are involved in critical pathway affected in cancer such as survival, apoptosis, epithelial-mesenchymal transition, and proliferation (XIV).

TABLE XIV

| KEGG Pathway (P < 0.001) | No. of Genes |
|---|---|
| MAPK Signaling Pathway | 159 |
| Regulation of Actin Cytoskeleton | 133 |
| Focal Adhesion | 130 |
| Wnt Signaling Pathway | 102 |
| Axon Guidance | 93 |
| Insulin Signaling Pathway | 92 |
| TGF-Beta Signaling Pathway | 69 |
| ErbB Signaling Pathway | 64 |
| Adherens Junction | 62 |
| Ribosome | 3 | miRNA Expression Profiling in Plasma Samples: Study Design

Validated circulating biomarkers in plasma/serum could potentially represent the gold standard for a noninvasive routine clinical application. We reasoned that ideal miRNA biomarkers should be identified before the onset of the tumors and be able to predict aggressive versus indolent disease development.

To determine whether specific miRNA signatures are already detectable in plasma samples collected before the detection of the disease, we performed high-throughput miRNA expression profiles of plasma samples using Taq-Man microfluidic cards (Applied Biosystems). We first analyzed plasma samples collected >1 y before disease development and at the time of disease detection (positive CT/surgery) in the training set (CT-screening trial INT-IEO). We generated miRNA signatures that were then validated in plasma samples (also predisease and at disease detection) of a validation set (CT-screening MILD cohort). The clinical-pathological characteristics of training and validation sets are shown in FIG. 1. As control groups, we tested 15 pools of plasma samples (5-7 individuals per pool, 81 individuals in total) collected from disease-free subjects (negative spiral-CT) from both trials, with age, sex, and smoking habits distribution similar to those of cases.

Using microfluidic cards, 113 miRNAs were found to be always expressed in all plasma samples, and a subset of 100 miRNAs was found to be consistently expressed in the 15 control pools, with a good reproducibility among biological duplicates (FIG. 15). These 100 miRNAs were then used to identify circulating biomarkers of risk, diagnosis, and prognosis in plasma samples collected before or in presence of CT-detected disease.

miRNA Ratios as Bioinformatics Tools for miRNA Analysis

Because the normalization of miRNA data in plasma samples is still a controversial issue, the ratios between the expression values of all miRNAs consistently expressed in plasma were computed. Each value of a single miRNA was compared with the values of all of the other 99 miRNAs, and 4,950 ratios were obtained and subsequently used to analyze differences between classes of samples resulting in the definition of ratios with clinical relevance. When using microfluidic cards, there is general agreement on the normalization of single miRNA expression using the mean values of expression of all miRNAs of each card (13). To validate the robustness of the miRNA ratios method, we compared the results obtained independently by the two methods in the microfluidic cards. The results showed that the miRNAs mostly deregulated in multiple ratios were the same as those detected using the normalization on the mean expression value, thus confirming the robustness of the ratios method.

The use of miRNA ratios seems to be an easily applicable method with potential for general clinical use that avoids the need for large scale, high-throughput analyses and was therefore used to develop clinically useful signatures based on circulating biomarkers.

Identification of Diagnostic and Prognostic Circulating miRNA Profiles in Plasma Samples Collected Before and at the Time of Disease Detection Class comparison analysis was initially performed in the training set to identify a group of miRNA ratios showing statistically significant differences between prediagnostic, diagnostic, and disease-free plasma (P<0.05). These ratios were then technically validated, in a subset of samples, by TaqMan MicroRNA assays.

To assess the consistency of miRNA ratios within the control pools, we compared the value of each ratio in two control pools with the mean value resulting from the analysis of the individual samples composing the pools. We found that the values were consistent.

However, because some ratios showed a high individual variability in the control subjects, possibly leading to a high number of false positives, we considered for further analyses only those ratios with minimal intrapool variability.

The signatures obtained were then used to calculate specificity and sensitivity in an independent validation set.

Because the range of miRNA expression levels in the two datasets was consistently different, possibly due to a storage effect (14), the patients in each dataset were compared with the respective control groups.

For the generation of the signatures predicting clinical outcome (both before and in presence of CT-detected disease), because of the small number of events, we grouped the two datasets. Cases with bad outcome were compared with the respective control pools, and the signatures obtained were then tested for their power to discriminate patients with bad (dead and alive with disease) or good (disease free) prognosis in the whole cohort.

miRNA Signature Identifies Individuals at Risk to Develop Lung Cancer

Figure 14A:
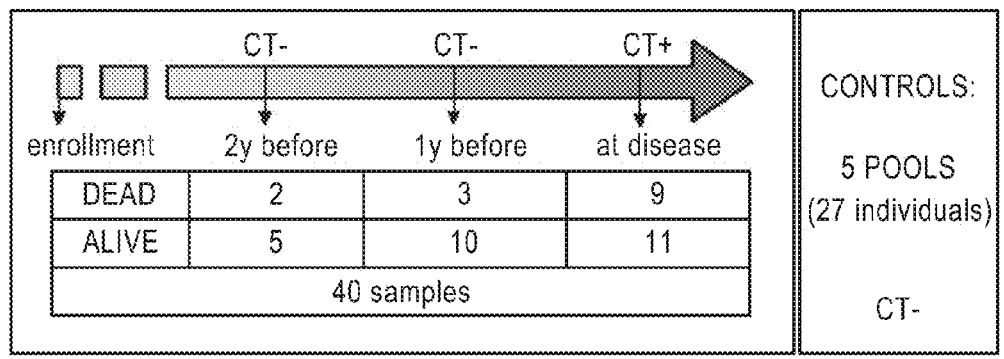
FIG. 14A is a diagram showing sample collection and analysis in the training set.
Figure 14B:
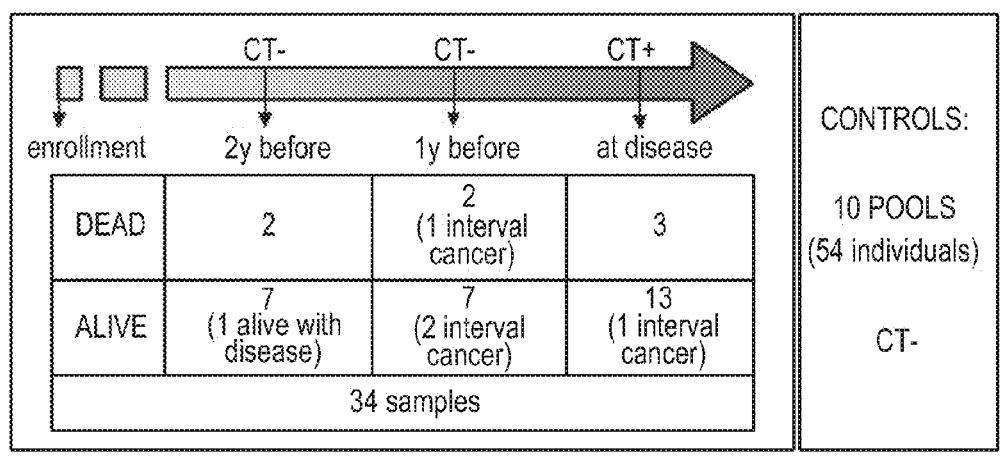
FIG. 14B is a diagram showing sample collection and analysis in the validation set.
Figure 14C:
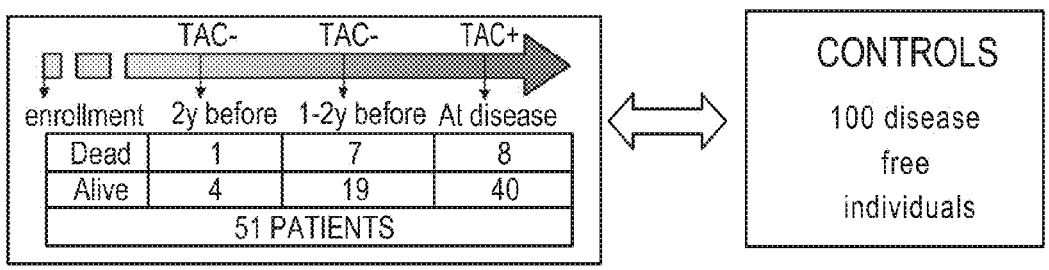
FIG. 14C is a diagram showing sample collection and analysis in an enlarged data set.

To investigate whether there are molecular markers predicting development of lung cancer, samples collected from patients 1 and/or 2 y before detection of the disease by CT were analyzed and compared with the control pools of heavy-smoking individuals (FIG. 14A-14C).

A signature of 16 ratios composed by 15 miRNAs could discriminate correctly 18 of 20 samples from subjects developing lung cancer in the training set (90% sensitivity) and resulted positive in only 1 of the 5 control pools (80% specificity). In the validation set, this signature identified 12 of 15 samples collected before lung cancer detection by spiral-CT, with sensitivity of 80% and specificity of 90% (AUC-ROC=0.85, P<0.0001; FIG. 4A). The predictive value of this signature was evaluated to be useful up to 28 mo before the disease, and mir-660, mir-140-5p, mir-451, mir-28-3p, mir-30c, and mir-92a are the most frequently deregulated miRNAs.

miRNA Signature with Diagnostic Value

Plasma samples collected at surgery or at time of disease detection by spiral CT were compared with pools of disease-free individuals to identify a miRNA profile associated with lung cancer diagnosis. In the training set, a panel of 16 ratios involving 13 different miRNAs classified 16 of 19 patients, with a sensitivity of 84% and a specificity of 80%. In the validation set plasma samples, 12 of 16 patients were correctly discriminated, with a sensitivity of 75% and a specificity of 100% (AUC-ROC=0.88, P<0.0001; FIG. 4B).

The lower sensitivity observed may be related to the presence of a higher number of small, early-stage nodules with indolent behavior in this series and the inclusion of two patients misclassified by both the signature of diagnosis and risk.

The diagnostic signature was then used for class prediction of predisease plasma samples in the same series. In the training set, 11 of 20 (55%) cases were classified as individuals with disease and, very interestingly, 10 of these 11 cases were characterized by poor prognosis (dead or alive with disease) or belonged to the group of patients identified from 3rd to 5th y of screening. In the validation set, similar results were obtained, with presence of the disease signature already in 10 of 15 (66.6%) predisease plasma samples. Moreover, looking at the three predisease samples of interval cancer cases (patients who developed lung cancer few months after a negative CT result), only 1 patient was classified by the risk signature. Instead, 2 cases (including the 1 identified by risk signature) already displayed the diagnostic signature 8-9 mo before disease detection. The interval cancer case not recognized by any signatures had a stage 1a tumor with good outcome, suggesting the presence of a low-risk nodule.

Only 4 ratios were shared by the signatures of risk and of diagnosis, and the miRNAs involved were partially different. mir-17, mir-660, mir-92a, mir-106a, and mir-19b were the most frequently deregulated at the time of lung cancer diagnosis.

Overall, these findings strengthen the observation that circulating miRNA in plasma is detectable well before clinical disease detection by spiral CT, indicating the possibility to select high-risk groups on the basis of miRNA profiling.

miRNA Signature of Risk to Develop Aggressive Lung Cancer

We analyzed the miRNA expression profiles in predisease plasma samples of individuals with poor clinical outcome to define a signature of miRNAs identifying individuals at high risk to develop an aggressive disease.

A signature of 10 ratios, composed of 9 different miRNAs, identified 5 of 5 patients with poor prognosis (dead or with progressive disease) in this first set (100% sensitivity and 100% specificity). In the validation set, 4 of 5 patients with poor prognosis were correctly classified, including a patient with poor prognosis who developed an interval cancer. The sensitivity of this signature in the validation set was 80% with 100% specificity.

mir-221, mir-660, mir-486-5p, mir-28-3p, mir-197, mir-106a, mir-451, mir-140-5p, and mir-16 are the miRNAs deregulated in the signature of aggressive disease.

The signature was then used for class prediction of predisease plasma samples of patients with good prognosis in training and validation sets. The signature identified 5 of 15 (33.3%) patients in the training set and 5 of 11 (45%) patients in the validation set (FIG. 4C). Interestingly, in both the datasets, most of these classified samples belonged to patients whose tumor was detected after the 3rd y of screening. This finding supports our previous observation on tissue samples where a distinct miRNA profile was identified in tumor and normal tissues of the same patients. Noticeably, among the patients with tumor diagnosed in the 2nd y of screening (all stage Ia and Ib tumors), only one case with stage 1b tumor had the risk signature of aggressive disease.

These results suggest that miRNA profiles in predisease plasma samples are able to predict the development of tumors with worse prognosis and might even be helpful in pinpointing those early stage tumors at high risk of aggressive evolution.

miRNA Expression in Plasma Samples at Time of Disease Detection and Prognosis

Then we looked at the association between miRNA expression and prognosis in plasma samples collected at the time of lung cancer diagnosis by generating a signature composed by 10 ratios, all containing mir-486-5p. This signature identified 7 of 8 patients with bad prognosis in the training set (88% sensitivity and 100% specificity). The signature of aggressive disease was observed also in 2 of 10 samples with good prognosis, one of these having a stage Ib tumor. In the validation set, only 3 plasma samples collected in presence of disease of patients with poor prognosis were available, and 2 of these had the profile of aggressive disease. The third case was misclassified by all of the analyses performed in all plasma samples collected during screening evaluations (FIG. 4D).

Again, this signature was used for class prediction of predisease plasma samples of patients in the training and validation sets. Half of the predisease samples of patients with bad prognosis were positive for both the signatures of aggressive disease, whereas the predisease samples of patients with good prognosis that showed the signature of aggressive disease belonged mainly (5 of 6) to patients with tumors detected after the 3rd y of screening. It is noteworthy that, although individuals in the training set have an extended follow-up and 5-y overall survival data are available, the shorter median follow-up observation time (14 mo) for patients in validation set might affect the strength of the prognostic signatures.

mir-486-5p, compared with mir-21, mir-126, mir-15b, mir-148a, mir-142-3p, mir-17, mir-197, mir-221, mir-28-3p, and mir-106a, appears to be always down-regulated in plasma of patients with bad outcome.

Analysis

The investigation of biological and molecular features of indolent and aggressive lung cancer is critical to identify specific risk markers for lung cancer development, to achieve the earliest possible prediction and intervention and, potentially, to define novel therapeutic targets.

In this study, we have focused on the role of miRNAs as biomarkers of lung disease by taking advantage of the availability of both tissue samples (tumor and normal lung) and multiple plasma samples, collected before and at the time of disease detection, from patients enrolled in two different spiral-CT screening trials with extended follow-up. These patients developed tumors displaying variable aggressive behavior during the course of the trials.

Although previous studies reported miRNA expression profiles predicting recurrence and prognosis only in lung tumor samples collected at the time of surgery for symptomatic lung cancer, our study provides unique results on miRNA signatures able to identify the presence of aggressive lung cancer not only in tumor, but also in normal lung tissues and in plasma samples of patients. Moreover, miRNAs deregulated in plasma samples collected before clinical appearance of disease were powerful molecular predictors of high-risk disease development.

In tumor samples, we confirmed up-regulation of known miRNAs such as mir-21, a miRNA with proproliferative and anti-apoptotic function that is reported to target PTEN, and described down-regulation of two miRNAs (mir-486 and mir-451) that are involved in maintenance of self-renewal capacity of bronchio-alveolar stem cells. Association analyses revealed that expression of mir-205 and mir-21 are markers linked to squamous cell carcinoma (SCC) and adenocarcinoma (ADC) histology, respectively, confirming previous studies on the validity of studying miRNA expression in support of histopathological diagnosis for a precise classification of tumor histology. Interestingly, miRNAs that were deregulated in the more aggressive tumors identified in later years of screening are involved in adhesion and invasion pathways: miR-339 was reported to negatively regulate intercellular cell adhesion molecule (ICAM)-1, and mir-128a has been involved in TGFβ pathway promotion of tumor cell invasion and metastasis. This miRNA specifically targets FOXO1A, a transcription factor involved in AKT signaling and apoptosis inhibition.

The finding of miRNA expression profiles associated with aggressive disease and poor survival in normal lung tissues of the patients strengthens the existing evidence on the critical influence of the normal lung microenvironment on tumor development and, in the present study, on tumor aggressiveness. It is possible to speculate that these markers might represent molecular signs of a "soil" that, after extensive damage caused by smoking, becomes permissive, or even promoting, for cancer development. Several miRNAs deregulated in normal lung tissue of the patients undergoing surgery are involved in major pathways linked to cancer. In particular, miR-126 is known to promote angiogenesis by repressing the inhibitors of VEGF signaling spred1 and pik3r2, and let-7 is involved in proinflammatory programs. In addition, AKT signaling is the major pathway influenced by miR-222, miR-30 regulates connective tissue growth factor, and mir-29b modulates anti-apoptotic and prometastatic matrix molecules by repressing Mcl-1. It is also interesting to note the down-regulation of mir-34b in patients with worse DFS, because mir-34b is a well known target of p53, which cooperates to control cell proliferation and adhesion-independent growth. The observation of a possible prognostic role of several miRNAs in normal lung opens up the possibility of innovative therapeutic strategies targeting the host rather than the tumor itself.

Because circulating miRNAs in plasma could be more tissue-specific than tumor-specific, we decided to perform a high-throughput miRNA expression in plasma profiling using microfluidic cards. We then developed multiplex real-time PCR assays to validate, as single PCR assays, those miRNA signatures significantly associated with clinical characteristics of the patients. We have optimized simple and highly reproducible miRNA assays and formulated a suitable algorithm for qRT-PCR data validation in plasma using miRNA reciprocal ratios. Our findings suggest that the assessment of a number of miRNAs in plasma by qRT-PCR assays is a potentially useful and clinically applicable procedure to improve lung cancer management.

miRNAs deregulated in tissue specimens were rarely detected in plasma samples, further strengthening the high tissue-specificity of miRNAs and suggesting a predictive role of plasma miRNAs independent from tissue specimens. We observed that a partially different set of miRNAs were deregulated in plasma before and at the time of disease. This finding might be explained by the consideration that genes and pathways necessary in the earlier phases of disease development are different from those required for the maintenance and the progression of the tumor.

Overall, the 21 miRNAs composing the signatures of risk, diagnosis, and prognosis in plasma belong to major pathways: cellular aging (mir-19b, mir-17, mir-106), bronchioalveolar and hematopoietic stem cells renewal (mir-486, mir-106a, 142-3p), tumor recurrence in stage I NSCLC (mir-27b; mir-106a; mir-19b; mir-15b mir-16, mi-21), and lung cancer aggressiveness (mir-221, mir-222). In particular mir-17, mir-92a, mir-19b, and mir-106a are oncomirs belonging to the same family responsible for increased proliferation, repression of apoptosis and induction of angiogenesis. mir-197 regulates expression of the tumor suppressor gene FUS1, whose expression is lost in a large proportion of lung tumors. mir-28-3p is located in a chromosomal region that is frequently amplified in lung cancer (3q28). mir-221 blocks PTEN expression leading to activation of the AKT pathway, and is suggested to play an important role in cell growth and invasiveness by targeting the PTEN/AKT pathway. Alterations of these pathways represent well established and meaningful risk factors in lung cancer. Finally, in a recent publication regarding circulating miRNAs, mir-21, mir-126, and mir-486-5p were also identified as potential blood-based biomarkers with diagnostic value in NSCLC patients.

The identification of miRNA signatures in plasma samples collected 1-2 y before disease that predict cancer development and prognosis is potentially useful in the selection of high-risk individuals who need to undergo spiral-CT surveillance. It is noteworthy that specific miRNA signatures in predisease plasma samples are able to predict and discriminate the development of the more aggressive, early metastatic tumors that are frequently undetectable by yearly spiral-CT. This information could be certainly helpful to prompt these individuals in pharmacological smoking cessation programs and possibly to propose more specific imaging for detection of occult metastatic disease (e.g., PET, whole-body MRI), as well as nontoxic treatments such as enrollment in prophylactic vaccination programs. Furthermore, the signature of a potentially aggressive disease could also help in the clinical management of the frequent early-stage nodules detected during CT-screening trials improving diagnostic algorithms.

Considering the noninvasive characteristics of plasma sampling and the reproducible and easy detection of miRNA markers, plasma-based miRNA biomarkers can be used in clinical practice and may help to avoid overdiagnosis and overtreatment of low-risk disease and late detection of high-risk and early metastatic disease (Boeri et al., *Proc Natl Acad Sci USA*. 108(9):3713-8, 2011)

Materials and Methods

CT Screening Protocols. In the INT/IEO screening cohort of 1,035 high-risk heavy smokers, the median age was 58 y (range 50-84), 739 (71%) were men, average tobacco consumption was 26 cigarettes daily for 37 y (median pack/years=40), and 14% were former smokers.

The following clinical parameters were evaluated: age, sex, pack/years index, forced expiratory ventilation in 1 s (FEV1%), CT year, pathological stage of detected cancers, histology, size, growth rate, standard uptake value (SUV) of PET. The $\chi^2$ test was used to examine the associations between predictor variables. Overall survival (OS) curves of lung cancer patients were estimated with the Kaplan-Meier method and compared with the log-rank test, using time from lung cancer onset until death or by censoring at the last follow-up date. Statistical analyses were carried out using SAS (SAS Institute Inc., Cary, N.C.) and R software. Two-sided P values<0.05 were considered statistically significant.

The second trial was a prospective randomized trial named Multicentric Italian Lung Detection trial (MILD) launched in 2005 (MILD trial, validation set). Current or former smokers, at least 50 years old and without history of cancer within the prior 5 y, were randomized in two study groups: a control group undergoing a program of primary prevention with pulmonary function test evaluation and an early-detection group where periodic spiral-CT was associated with primary prevention and pulmonary function test evaluation. The early-detection group was further randomized in two arms: yearly low-dose spiral CT vs. spiral CT every 2 y. A total of 2,352 subjects were randomized in one of the two CT screening arms.

During enrollment and annual recall of all volunteers in both trials, whole blood was collected in EDTA vacuum tubes and plasma immediately separated by two centrifugation steps at 1,258 relative centrifugal force×g at 4° C. and stored in a biological bank, supported by a database recording all clinical and epidemiological information. Tissue samples from lung tumors and matching normal lung tissue (sampled at distance from the cancer lesion) were also collected when available from patients undergoing surgical resections. Tissue and plasma specimens were obtained according to the Internal Review and the Ethics Boards of the Istituto Nazionale Tumori of Milan.

miRNA Microarray Analysis in Tissue Samples

For expression analyses, we first used a set of 28 snap-frozen spiral-CT detected lung primary tumors and 24 paired normal lung tissues, collected during the INT/IEO trial. miRNA labeling and hybridization was performed using 5 μg of total TRIzol (Invitrogen) extracted RNA. The miRNA microarray (Ohio State University Comprehensive Cancer Center, version 2.0) used contained probes for 460 mature miRNAs spotted in quadruplicate (235 *Homo sapiens*, 222 *Mus musculus*, and three *Arabidopsis thaliana*) with annotated active sites selected for oligonucleotide design. Hybridization signals were detected with streptavidin-Alexa-647 conjugate, and scanned images (Perkin-Elmer ScanArray XL5K Scanner) were quantified using the GeneSpring software version 7.2 (Silicon Genetics, Redwood City, Calif.).

Statistical and Bioinformatics Analyses on Tissue Samples

On the microarray chips, after background subtraction and data transformation (to convert any negative value to 0.01), the average value of the four spots was normalized using a per-chip 50th percentile method that normalizes each chip on its median.

Class Comparison and Class Prediction Analyses. Statistical analyses were performed using BRB ArrayTools 3.8.1 software developed by Dr. Richard Simon at the National Cancer Institute. MicroRNA differentially expressed between two classes were considered significant at the nominal 0.001-0.003 level of the univariate test based on 10,000 random permutations and were used for class prediction analyses with the multiple methods tool.

miRNA Profiling in Plasma Samples miRNA expression profiling was performed in 40 plasma samples, collected 12-28 mo before and at time of the disease detection, from 19 patients in the training set and in 34 plasma samples from 22 patients from the validation set. Using mirVana PARISKit (Ambion), total RNA was extracted from 200-μl plasma samples, and miRNA expression was determined using the Megaplex Pools Protocol on microfluidic card type A (Applied Biosystems). The control groups were represented by 15 pools of 5-7 plasma samples each from disease-free individuals enrolled in the same trials and matched to the patients by sex, age, and smoking habit. For each micro-fluidic card (sample), the Ct of every miRNA was determined using the program SDS 2.2.2 (Applied Biosystems) and setting a threshold of 0.2 and a manual baseline from 3 to 18 cycles.

Quantitative Real-Time PCR. Tissues

Starting from 20 ng of total RNA in the reverse transcription (RT) step, TaqMan MicroRNA Assays (Applied Biosystems) were used for quantitative real-time PCR following their standard procedures. Relative quantification was performed using the ΔΔCt method using as housekeeping the miRNA RNU-6B.

Plasma samples. Starting from 3 μl of the same plasma free-circulating RNA used for the Megaplex Pools Protocol (Applied Biosystems), selected miRNAs were validated with the Multiplex Pools Protocol (Applied Biosystems).

Results

FIG. 15 shows the consistency of miRNA expression measurement in plasma samples by quantitative real-time PCR considering only the 100 miRNAs selected for class comparison analysis. (A) Technical duplicates were performed for two patient samples (341 and 380) and for a control pool (M2). The graphical representation was performed plotting the first miRNA values obtained on abscissa (duplicate A) and the values obtained in the second evaluation in ordinate (duplicate B). The linear regression value shows a good reproducibility of measurements. (B) Correlation between two different control pools. (C) Graphical representation of average values of all Pearson correlation coefficients between control pools, technical duplicates, and between all patient samples (before and at time of disease).

We claim:

1. A method of identifying a subject at risk of having a pulmonary tumor comprising:
   (a) in a biological sample from the subject, wherein the biological sample is whole blood, a fraction of blood, plasma or serum,
      (1) measuring a level of expression of each of the miRNAs selected from the group consisting of hsa-miR-660, hsa-miR-197, hsa-miR-17, hsa-miR-106a, hsa-miR-142-3p, hsa-miR-92a, hsa-miR-19b, hsa-miR-101, hsa-miR-145, hsa-miR-28-3p, hsa-miR-320, hsa-miR-126, hsa-miR-140-5p and hsa-miR-148;
      (2) calculating a plurality of ratios between the levels of expression from (a)(1) of pairs of miRNAs selected from the group consisting of hsa-miR-106a/hsa-miR-660, hsa-miR-106a/hsa-miR-92a, hsa-miR-197, hsa-miR-92a and hsa-miR-197/hsa-miR-660;
   (b) in at least one biological sample from a plurality of disease-free individuals, wherein the biological sample is whole blood, a fraction of blood, plasma or serum,
      (1) measuring a level of expression of each of the miRNAs selected from the group consisting of hsa-miR-660, hsa-miR-197, hsa-miR-17, hsa-miR-106a, hsa-miR-142-3p, hsa-miR-92a, hsa-miR-19b, hsa-miR-101, hsa-miR-145, hsa-miR-28-3p, hsa-miR-320, hsa-miR-126, hsa-miR-140-5p and hsa-miR-148;
      (2) calculating a plurality of ratios between the levels of expression from (b)(1) of pairs of miRNAs selected from the group consisting of hsa-miR-106a/hsa-miR-660, hsa-miR-106a/hsa-miR-92a, hsa-miR-197/hsa-miR-92a and hsa-miR-197/hsa-miR-660; and
      (3) calculating an average and standard deviation for each of the miRNA ratios of (b)(2), wherein the average +/− one standard deviation is a cut-off value;
   (c) identifying the subject as being at risk for pulmonary tumor if at least 4 of the ratios in (a)(2) exceed the cut-off value of (b)(3); or
   (d) identifying the subject as not being at risk for pulmonary tumor if at least 4 of the ratios in (a)(2) do not exceed the cut-off value of (b)(3).

2. The method of claim 1, wherein steps (a)(2) and (b)(2) further comprise calculating a plurality of ratios between the level of expression of pairs of miRNAs selected from the group consisting of hsa-miR-106a/hsa-miR-197, hsa-miR-140-5p/hsa-miR-197, hsa-miR-140-5p/hsa-miR-28-3p, hsa-miR-142-3p/hsa-miR-197, hsa-miR-142-3p/hsa-miR-28-3p, hsa-miR-28-3p/hsa-miR-660 and hsa-miR-28-3p/hsa-miR-92a.

3. The method according to claim 2, wherein steps (a)(2) and (b)(2) further comprise calculating a plurality of real ratios between the level of expression of pairs of miRNAs selected from the group consisting of hsa-miR-101/hsa-miR-660, hsa-miR-101/hsa-miR-92a, hsa-miR-106a/hsa-miR-320, hsa-miR-126/hsa-miR-660, hsa-miR-126/hsa-miR-92a, hsa-miR-142-3p/hsa-miR-145, hsa-miR-145/hsa-miR-660, hsa-miR-145/hsa-miR-92a, hsa-miR-148a/hsa-miR-660, hsa-miR-148a/hsa-miR-92a, hsa-miR-17/hsa-miR-320, hsa-miR-17/hsa-miR-660, hsa-miR-17/hsa-miR-92a, hsa-miR-197/hsa-miR-320, hsa-miR-19b/hsa-miR-660, hsa-miR-19b/hsa-miR-92a.

4. The method according to claim 3, wherein the pairs of miRNAs in steps (a)(2) and (b)(2) are selected from the group consisting of hsa-miR-106a/hsa-miR-660, hsa-miR-101/hsa-miR-660, hsa-miR-126/hsa-miR-660, hsa-miR-145/hsa-miR-660, hsa-miR-148a/hsa-miR-660, hsa-miR-17/hsa-miR-660, hsa-miR-19b/hsa-miR-660, hsa-miR-28-3p/hsa-miR-660, hsa-miR-197/hsa-miR-660, hsa-miR-197/hsa-miR-320, hsa-miR-197/hsa-miR-92a, hsa-miR-140-5p/hsa-miR-197, hsa-miR-142-3p/hsa-miR-197 and hsa-miR-106a/hsa-miR-197.

5. The method according to claim 3, wherein the pairs of miRNAs in steps (a)(2) and (b)(2) are selected from the group consisting of hsa-miR-101/hsa-miR-660, hsa-miR-106a/hsa-miR-660, hsa-miR-126/hsa-miR-660, hsa-miR-145/hsa-miR-660, hsa-miR-148a/hsa-miR-660, hsa-miR-17/hsa-miR-660, hsa-miR-197/hsa-miR-660, hsa-miR-19b/hsa-miR-660, hsa-miR-28-3p/hsa-miR-660, hsa-miR-106a/hsa-miR-197, hsa-miR-140-5p/hsa-miR-197, hsa-miR-142-3p/hsa-miR-197, hsa-miR-197/hsa-miR-320, hsa-miR-197/hsa-miR-92a, hsa-miR-142-3p/hsa-miR-145 and hsa-miR-142-3p/hsa-miR-28-3p.

6. The method of claim 1, wherein said tumor cannot be detected by spiral CT scan.

7. The method of claim 1, wherein said method confirms detection by spiral CT scan.

8. The method according to claim 1, further comprising
   (e) in a biological sample from the subject, wherein the biological sample is whole blood, a fraction of blood, plasma or serum,
      (1) measuring a level of expression of each of the miRNAs selected from the group consisting of hsa-miR-148a, hsa-miR-486-5p, hsa-miR-21, hsa-miR-16, hsa-miR-30b, hsa-miR-15b and hsa-miR-221;
      (2) calculating a plurality of ratios between the levels of expression from (e)(1) of pairs of miRNAs selected from the group consisting of hsa-miR-142-3p/hsa-miR-19b, hsa-miR-142-3p/hsa-miR-486-5p, hsa-miR-19b/hsa-miR-21, hsa-miR-19b/hsa-miR-221, hsa-miR-21/hsa-miR-486-5p, hsa-miR-21/hsa-miR-660, hsa-miR-221/hsa-miR-486-5p, hsa-miR-221/hsa-miR-660 and hsa-miR-142-3p/hsa-miR-660;
   (f) in at least one biological sample from a plurality of disease-free individuals, wherein the biological sample is whole blood, a fraction of blood, plasma or serum,
      (1) measuring a level of expression of each of the miRNAs selected from the group consisting of hsa-miR-148a, hsa-miR-486-5p, hsa-miR-21, hsa-miR-16, hsa-miR-30b, hsa-miR-15b and hsa-miR-221;
      (2) calculating a plurality of ratios between the levels of expression from (f)(1) of pairs of miRNAs selected from the group consisting of hsa-miR-142-3p/hsa-miR-19b, hsa-miR-142-3p/hsa-miR-486-5p, hsa-miR-19b/hsa-miR-21, hsa-miR-19b/hsa-miR-221, hsa-miR-21/hsa-miR-486-5p, hsa-miR-21/hsa-miR-660, hsa-miR-221/hsa-miR-486-5p, hsa-miR-221/hsa-miR-660 and hsa-miR-142-3p/hsa-miR-660;
      (3) calculating an average and standard deviation for each of the miRNA ratios of (f)(2), wherein the average +/− one standard deviation is a cut-off value;
   (g) identifying the subject as being at risk for an aggressive pulmonary tumor if at least 50% of the ratios in (e)(2) exceed the cut-off value of (f)(3); or
   (d) identifying the subject as not being at risk for an aggressive pulmonary tumor if at least 50% of the ratios in (e)(2) exceed the cut-off value of (f)(3).

9. The method according to claim 8, wherein steps (e)(2) and (f)(2) further comprise calculating a plurality of real ratios between the level of expression of pairs of miRNAs selected from the group consisting of hsa-miR-142-3p/hsa-miR-660, hsa-miR-148a/hsa-miR-19b, hsa-miR-148a/hsa-miR-486-5p, hsa-miR-15b/hsa-miR-19b, hsa-miR-15b/hsamiR-486-5p, hsa-miR-16/hsa-miR-486-5p, hsa-miR-19b/hsa-miR-30b and hsa-miR-30b/hsa-miR-486-5p.

10. The method according to claim 1, further comprising
(e) in a biological sample from the subject, wherein the biological sample is whole blood, a fraction of blood, plasma or serum,
  (1) measuring a level of expression of each of the miRNAs selected from the group consisting of hsa-miR-451, hsa-miR-148a, hsa-miR-486-5p, hsa-miR-21, hsa-miR-16, hsa-miR-30b, hsa-miR-30c and hsa-miR-15b;
  (2) calculating a plurality of ratios between the levels of expression from (e)(1) of pairs of miRNAs selected from the group consisting of hsa-miR-106a/hsa-miR-197, hsa-miR-106a/hsa-miR-451, hsa-miR-106a/hsa-miR-486-5p, hsa-miR-126/hsa-miR-197, hsa-miR-126/hsa-miR-451, hsa-miR-126/hsa-miR-486-5p, hsa-miR-17/hsa-miR-197, hsa-miR-17/hsa-miR-451, hsa-miR-17/hsa-miR-486-5p, hsa-miR-197/hsa-miR-451 and hsa-miR-197/hsa-miR-486-5p;
(f) in at least one biological sample from a plurality of disease-free individuals, wherein the biological sample is whole blood, a fraction of blood, plasma or serum,
  (1) measuring a level of expression of each of the miRNAs selected from the group consisting of hsa-miR-451, hsa-miR-148a, hsa-miR-486-5p, hsa-miR-21, hsa-miR-16, hsa-miR-30b, hsa-miR-30c and hsa-miR-15b;
  (2) calculating a plurality of ratios between the levels of expression from (f)(1) of pairs of miRNAs selected from the group consisting of hsa-miR-106a/hsa-miR-197, hsa-miR-106a/hsa-miR-451, hsa-miR-106a/hsa-miR-486-5p, hsa-miR-126/hsa-miR-197, hsa-miR-126/hsa-miR-451, hsa-miR-126/hsa-miR-486-5p, hsa-miR-17/hsa-miR-197, hsa-miR-17/hsa-miR-451, hsa-miR-17/hsa-miR-486-5p, hsa-miR-197/hsa-miR-451 and hsa-miR-197/hsa-miR-486-5p;
  (3) calculating an average and standard deviation for each of the miRNA ratios of (f)(2), wherein the average +/- one standard deviation is a cut-off value;
(g) identifying the subject as being at risk for an aggressive pulmonary tumor if at least 50% of the ratios in (e)(2) exceed the cut-off value of (f)(3); or
(d) identifying the subject as not being at risk for an aggressive pulmonary tumor if at least 50% of the ratios in (e)(2) exceed the cut-off value of (f)(3).

11. The method according to claim 10, wherein steps (e)(2) and (f)(2) further comprise calculating a plurality of real ratios between the level of expression of pairs of miRNAs selected from the group consisting of hsa-miR-101/hsa-miR-197, hsa-miR-126/hsa-miR-660, hsa-miR-140-5p/hsa-miR-197, hsa-miR-140-5p/hsa-miR-28-3p, hsa-miR-142-3p/hsa-miR-197, hsa-miR-145/hsa-miR-451, hsa-miR-148a/hsa-miR-451, hsa-miR-15b/hsa-miR-451, hsa-miR-16/hsa-miR-197, hsa-miR-197/hsa-miR-19b, hsa-miR-197/hsa-miR-21, hsa-miR-197/hsa-miR-660, hsa-miR-197/hsa-miR-92a, hsa-miR-19b/hsa-miR-451, hsa-miR-19b/hsa-miR-486-5p, hsa-miR-19b/hsa-miR-660, hsa-miR-28-3p/hsa-miR-451, hsa-miR-28-3p/hsa-miR-486-5p, hsa-miR-28-3p/hsa-miR-660, hsa-miR-30b/hsa-miR-451 and hsa-miR-30c/hsa-miR-451.

12. The method of any one of claims 1 and 2-11, wherein the pulmonary tumor is small-cell lung cancer (SCLC), non-small cell lung cancer (NSCLC), pulmonary adenocarcinoma (ADC), bronchio-alveolar carcinoma (BAC), squamous-cell lung carcinoma (SCC) or large-cell carcinoma (LC).

13. The method of any one of claims 1 and 2-12, wherein the biological sample originates from a subject who smokes or has a history of smoking.

14. The method of 13, wherein, at the moment of the collection of the sample, the subject does not present a pulmonary tumor if subjected to imaging diagnostic methods.

15. The method of 14, wherein the subject does not present nodules of dimensions of greater than 5 mm if subjected to a spiral CT scan.

* * * * *

```
                        SEQUENCE LISTING

<160> NUMBER OF SEQ ID NOS: 123

<210> SEQ ID NO 1
<211> LENGTH: 110
<212> TYPE: RNA
<213> ORGANISM: Homo sapiens

<400> SEQUENCE: 1
cuggauacag aguggaccgg cuggccccau cuggaagacu agugauuuug uuguugucuu      60
acugcgcuca acaacaaauc ccagucuacc uaaugguggcc agccaucgca               110

<210> SEQ ID NO 2
<211> LENGTH: 23
<212> TYPE: RNA
<213> ORGANISM: Homo sapiens

<400> SEQUENCE: 2
uggaagacua gugauuuugu ugu                                              23

<210> SEQ ID NO 3
<211> LENGTH: 22
<212> TYPE: RNA
<213> ORGANISM: Homo sapiens

<400> SEQUENCE: 3
caacaaaucc cagucuaccu aa                                               22

<210> SEQ ID NO 4
<211> LENGTH: 98
<212> TYPE: RNA
<213> ORGANISM: Homo sapiens

<400> SEQUENCE: 4
uugaggccuu aaaguacugu agcagcacau caugguuuac augcuacagu caagaugcga     60
aucauuauuu gcugcucuag aaauuuaagg aaauucau                              98

<210> SEQ ID NO 5
<211> LENGTH: 22
<212> TYPE: RNA
<213> ORGANISM: Homo sapiens

<400> SEQUENCE: 5
uagcagcaca ucaugguuua ca                                               22

<210> SEQ ID NO 6
<211> LENGTH: 22
<212> TYPE: RNA
<213> ORGANISM: Homo sapiens

<400> SEQUENCE: 6
cgaaucauua uuugcugcuc ua                                               22
```

<210> SEQ ID NO 7
<211> LENGTH: 89
<212> TYPE: RNA
<213> ORGANISM: Homo sapiens

<400> SEQUENCE: 7
gucagcagug ccuuagcagc acguaaauau uggcguuaag auucuaaaau uaucuccagu    60
auuaacugug cugcugaagu aagguugac                                    89

<210> SEQ ID NO 8
<211> LENGTH: 81
<212> TYPE: RNA
<213> ORGANISM: Homo sapiens

<400> SEQUENCE: 8
guuccacucu agcagcacgu aaauauuggc guagugaaau auauauuaaa caccaauauu    60
acugugcugc uuuaguguga c                                            81

<210> SEQ ID NO 9
<211> LENGTH: 22
<212> TYPE: RNA
<213> ORGANISM: Homo sapiens

<400> SEQUENCE: 9
uagcagcacg uaaauauugg cg                                           22

<210> SEQ ID NO 10
<211> LENGTH: 22
<212> TYPE: RNA
<213> ORGANISM: Homo sapiens

<400> SEQUENCE: 10
ccaauauuac ugugcugcuu ua                                           22

<210> SEQ ID NO 11
<211> LENGTH: 84
<212> TYPE: RNA
<213> ORGANISM: Homo sapiens

<400> SEQUENCE: 11
gucagaauaa ugucaaagug cuuacagugc agguagugau augugcaucu acugcaguga    60
aggcacuugu agcauuaugg ugac                                         84

<210> SEQ ID NO 12
<211> LENGTH: 23
<212> TYPE: RNA
<213> ORGANISM: Homo sapiens

<400> SEQUENCE: 12
caaagugcuu acagugcagg uag                                          23

<210> SEQ ID NO 13
<211> LENGTH: 22
<212> TYPE: RNA
<213> ORGANISM: Homo sapiens

<400> SEQUENCE: 13
acugcaguga aggcacuugu ag                                           22

<210> SEQ ID NO 14
<211> LENGTH: 87

```
<212> TYPE: RNA
<213> ORGANISM: Homo sapiens

<400> SEQUENCE: 14
cacuguucua ugguuaguuu ugcagguuug cauccagcug ugugauauuc ugcugugcaa      60
auccaugcaa aacugacugu gguagug                                         87

<210> SEQ ID NO 15
<211> LENGTH: 23
<212> TYPE: RNA
<213> ORGANISM: Homo sapiens

<400> SEQUENCE: 15
aguuuugcag guuugcaucc agc                                             23

<210> SEQ ID NO 16
<211> LENGTH: 96
<212> TYPE: RNA
<213> ORGANISM: Homo sapiens

<400> SEQUENCE: 16
acauugcuac uuacaauuag uuuugcaggu uugcauuuca gcguauauau guauaugugg      60
cugugcaaau ccaugcaaaa cugauuguga uaaugu                               96

<210> SEQ ID NO 17
<211> LENGTH: 22
<212> TYPE: RNA
<213> ORGANISM: Homo sapiens

<400> SEQUENCE: 17
aguuuugcag guuugcauuu ca                                              22

<210> SEQ ID NO 18
<211> LENGTH: 23
<212> TYPE: RNA
<213> ORGANISM: Homo sapiens

<400> SEQUENCE: 18
ugugcaaauc caugcaaaac uga                                             23

<210> SEQ ID NO 19
<211> LENGTH: 72
<212> TYPE: RNA
<213> ORGANISM: Homo sapiens

<400> SEQUENCE: 19
ugucggguag cuuaucagac ugauguugac uguugaaucu cauggcaaca ccagucgaug      60
ggcugucuga ca                                                         72

<210> SEQ ID NO 20
<211> LENGTH: 22
<212> TYPE: RNA
<213> ORGANISM: Homo sapiens

<400> SEQUENCE: 20
uagcuuauca gacugauguu ga                                              22

<210> SEQ ID NO 21
<211> LENGTH: 21
<212> TYPE: RNA
<213> ORGANISM: Homo sapiens
```

```
<400> SEQUENCE: 21
caacaccagu cgaugggcug u                                              21

<210> SEQ ID NO 22
<211> LENGTH: 86
<212> TYPE: RNA
<213> ORGANISM: Homo sapiens

<400> SEQUENCE: 22
gguccuugcc cucaaggagc ucacagucua uugaguuacc uuucgacuu ucccacuaga     60 uugugagcuc cuggagggca ggcacu                                         86

<210> SEQ ID NO 23
<211> LENGTH: 22
<212> TYPE: RNA
<213> ORGANISM: Homo sapiens

<400> SEQUENCE: 23
aaggagcuca cagucuauug ag                                             22

<210> SEQ ID NO 24
<211> LENGTH: 22
<212> TYPE: RNA
<213> ORGANISM: Homo sapiens

<400> SEQUENCE: 24
cacuagauug ugagcuccug ga                                             22

<210> SEQ ID NO 25
<211> LENGTH: 71
<212> TYPE: RNA
<213> ORGANISM: Homo sapiens

<400> SEQUENCE: 25
gcgacuguaa acauccucga cuggaagcug ugaagccaca gaugggcuuu cagucggaug    60
uuugcagcug c                                                         71

<210> SEQ ID NO 26
<211> LENGTH: 22
<212> TYPE: RNA
<213> ORGANISM: Homo sapiens

<400> SEQUENCE: 26
uguaaacauc cucgacugga ag                                             22

<210> SEQ ID NO 27
<211> LENGTH: 22
<212> TYPE: RNA
<213> ORGANISM: Homo sapiens

<400> SEQUENCE: 27
cuuucagucg gauguuugca gc                                             22

<210> SEQ ID NO 28
<211> LENGTH: 88
<212> TYPE: RNA
<213> ORGANISM: Homo sapiens

<400> SEQUENCE: 28
accaaguuuc aguucaugua aacauccuac acucagcugu aauacaugga uuggcuggga    60 ggugauguu uacuucagcu gacuugga                                        88
```

-continued

```
<210> SEQ ID NO 29
<211> LENGTH: 22
<212> TYPE: RNA
<213> ORGANISM: Homo sapiens

<400> SEQUENCE: 29
uguaaacauc cuacacucag cu                                              22

<210> SEQ ID NO 30
<211> LENGTH: 22
<212> TYPE: RNA
<213> ORGANISM: Homo sapiens

<400> SEQUENCE: 30
cugggaggug gauguuuacu uc                                              22

<210> SEQ ID NO 31
<211> LENGTH: 89
<212> TYPE: RNA
<213> ORGANISM: Homo sapiens

<400> SEQUENCE: 31
accaugcugu agugugugua aacauccuac acucucagcu gugagcucaa gguggcuggg     60
agaggguugu uuacuccuuc ugccaugga                                       89

<210> SEQ ID NO 32
<211> LENGTH: 22
<212> TYPE: RNA
<213> ORGANISM: Homo sapiens

<400> SEQUENCE: 32
cugggagagg guuguuuacu cc                                              22

<210> SEQ ID NO 33
<211> LENGTH: 72
<212> TYPE: RNA
<213> ORGANISM: Homo sapiens

<400> SEQUENCE: 33
agauacugua aacauccuac acucucagcu guggaaagua agaaagcugg gagaaggcug     60
uuuacucuuu cu                                                         72

<210> SEQ ID NO 34
<211> LENGTH: 23
<212> TYPE: RNA
<213> ORGANISM: Homo sapiens

<400> SEQUENCE: 34
uguaaacauc cuacacucuc agc                                             23

<210> SEQ ID NO 35
<211> LENGTH: 22
<212> TYPE: RNA
<213> ORGANISM: Homo sapiens

<400> SEQUENCE: 35
cugggagaag gcuguuuacu cu                                              22

<210> SEQ ID NO 36
<211> LENGTH: 70
<212> TYPE: RNA
```

<213> ORGANISM: Homo sapiens

<400> SEQUENCE: 36
guuguuguaa caucccga cuggaagcug uaagacacag cuaagcuuuc agucagaugu    60
uugcugcuac    70

<210> SEQ ID NO 37
<211> LENGTH: 22
<212> TYPE: RNA
<213> ORGANISM: Homo sapiens

<400> SEQUENCE: 37
uguaaacauc cccgacugga ag    22

<210> SEQ ID NO 38
<211> LENGTH: 22
<212> TYPE: RNA
<213> ORGANISM: Homo sapiens

<400> SEQUENCE: 38
cuuucaguca gauguuugcu gc    22

<210> SEQ ID NO 39
<211> LENGTH: 84
<212> TYPE: RNA
<213> ORGANISM: Homo sapiens

<400> SEQUENCE: 39
gugcucgguu uguaggcagu gucauuagcu gauuguacug ugguggguuac aaucacuaac    60 uccacugcca ucaaaacaag gcac    84

<210> SEQ ID NO 40
<211> LENGTH: 23
<212> TYPE: RNA
<213> ORGANISM: Homo sapiens

<400> SEQUENCE: 40
uaggcagugu cauuagcuga uug    23

<210> SEQ ID NO 41
<211> LENGTH: 22
<212> TYPE: RNA
<213> ORGANISM: Homo sapiens

<400> SEQUENCE: 41
caaucacuaa cuccacugcc au    22

<210> SEQ ID NO 42
<211> LENGTH: 78
<212> TYPE: RNA
<213> ORGANISM: Homo sapiens

<400> SEQUENCE: 42
cuuucuacac agguugggau cgguugcaau gcuguguuuc uguaugguau ugcacuuguc    60
ccggccuguu gaguuugg    78

<210> SEQ ID NO 43
<211> LENGTH: 23
<212> TYPE: RNA
<213> ORGANISM: Homo sapiens

<400> SEQUENCE: 43

```
agguugggau cgguugcaau gcu                                         23

<210> SEQ ID NO 44
<211> LENGTH: 22
<212> TYPE: RNA
<213> ORGANISM: Homo sapiens

<400> SEQUENCE: 44
uauugcacuu gucccggccu gu                                          22

<210> SEQ ID NO 45
<211> LENGTH: 75
<212> TYPE: RNA
<213> ORGANISM: Homo sapiens

<400> SEQUENCE: 45
ucaucccugg gugggauuu guugcauuac uuguguucua auaaaaguau ugcacuuguc   60
ccggccugug gaaga                                                  75

<210> SEQ ID NO 46
<211> LENGTH: 22
<212> TYPE: RNA
<213> ORGANISM: Homo sapiens

<400> SEQUENCE: 46 gggugggau uuguugcauu ac                                           22

<210> SEQ ID NO 47
<211> LENGTH: 75
<212> TYPE: RNA
<213> ORGANISM: Homo sapiens

<400> SEQUENCE: 47
ugcccuggcu caguuaucac agugcugaug cugucuauuc uaaagguaca guacugugau  60
aacugaagga uggca                                                  75

<210> SEQ ID NO 48
<211> LENGTH: 22
<212> TYPE: RNA
<213> ORGANISM: Homo sapiens

<400> SEQUENCE: 48
caguuaucac agugcugaug cu                                          22

<210> SEQ ID NO 49
<211> LENGTH: 21
<212> TYPE: RNA
<213> ORGANISM: Homo sapiens

<400> SEQUENCE: 49
uacaguacug ugauaacuga a                                           21

<210> SEQ ID NO 50
<211> LENGTH: 79
<212> TYPE: RNA
<213> ORGANISM: Homo sapiens

<400> SEQUENCE: 50
acuguccuuu uucgguuauc augguaccga ugcuguauau cugaaaggua caguacugug  60
auaacugaag aauggguggu                                             79
```

```
<210> SEQ ID NO 51
<211> LENGTH: 21
<212> TYPE: RNA
<213> ORGANISM: Homo sapiens

<400> SEQUENCE: 51
uacaguacug ugauaacuga a                                              21

<210> SEQ ID NO 52
<211> LENGTH: 81
<212> TYPE: RNA
<213> ORGANISM: Homo sapiens

<400> SEQUENCE: 52
ccuuggccau guaaaagugc uuacagugca gguagcuuuu ugagaucuac ugcaauguaa    60
gcacuucuua cauuaccaug g                                              81

<210> SEQ ID NO 53
<211> LENGTH: 23
<212> TYPE: RNA
<213> ORGANISM: Homo sapiens

<400> SEQUENCE: 53
aaaagugcuu acagugcagg uag                                            23

<210> SEQ ID NO 54
<211> LENGTH: 22
<212> TYPE: RNA
<213> ORGANISM: Homo sapiens

<400> SEQUENCE: 54
cugcaaugua agcacuucuu ac                                             22

<210> SEQ ID NO 55
<211> LENGTH: 85
<212> TYPE: RNA
<213> ORGANISM: Homo sapiens

<400> SEQUENCE: 55
cgcuggcgac gggacauuau uacuuuuggu acgcgcugug acacuucaaa cucguaccgu    60
gaguaauaau gcgccgucca cggca                                          85

<210> SEQ ID NO 56
<211> LENGTH: 21
<212> TYPE: RNA
<213> ORGANISM: Homo sapiens

<400> SEQUENCE: 56
cauuauuacu uuugguacgc g                                              21

<210> SEQ ID NO 57
<211> LENGTH: 22
<212> TYPE: RNA
<213> ORGANISM: Homo sapiens

<400> SEQUENCE: 57
ucguaccgug aguaauaaug cg                                             22

<210> SEQ ID NO 58
<211> LENGTH: 88
<212> TYPE: RNA
<213> ORGANISM: Homo sapiens
```

```
<400> SEQUENCE: 58
acaaugcuuu gcuagagcug guaaaaugga accaaaucgc cucuucaaug gauuuggucc      60
ccuucaacca gcuguagcua ugcauuga                                       88

<210> SEQ ID NO 59
<211> LENGTH: 102
<212> TYPE: RNA
<213> ORGANISM: Homo sapiens

<400> SEQUENCE: 59
gggagccaaa ugcuuugcua gagcugguaa aauggaacca aaucgacugu ccaauggauu      60 uggucccuu caaccagcug uagcugugca uugauggcgc cg                        102

<210> SEQ ID NO 60
<211> LENGTH: 22
<212> TYPE: RNA
<213> ORGANISM: Homo sapiens

<400> SEQUENCE: 60
uuuggucccc uucaaccagc ug                                              22

<210> SEQ ID NO 61
<211> LENGTH: 100
<212> TYPE: RNA
<213> ORGANISM: Homo sapiens

<400> SEQUENCE: 61 ugucucuc ucuguguccu gccagugguu uacccuaug guagguuacg ucaugcuguu        60
cuaccacagg guagaaccac ggacaggaua ccggggcacc                          100

<210> SEQ ID NO 62
<211> LENGTH: 22
<212> TYPE: RNA
<213> ORGANISM: Homo sapiens

<400> SEQUENCE: 62
cagugguuuu acccuauggu ag                                              22

<210> SEQ ID NO 63
<211> LENGTH: 21
<212> TYPE: RNA
<213> ORGANISM: Homo sapiens

<400> SEQUENCE: 63
uaccacaggg uagaaccacg g                                               21

<210> SEQ ID NO 64
<211> LENGTH: 87
<212> TYPE: RNA
<213> ORGANISM: Homo sapiens

<400> SEQUENCE: 64
gacagugcag ucacccauaa aguagaaagc acuacuaaca gcacuggagg guguaguguu      60
uccuacuuua uggaugagug uacugug                                        87

<210> SEQ ID NO 65
<211> LENGTH: 21
<212> TYPE: RNA
<213> ORGANISM: Homo sapiens
```

```
<400> SEQUENCE: 65
cauaaaguag aaagcacuac u                                              21

<210> SEQ ID NO 66
<211> LENGTH: 23
<212> TYPE: RNA
<213> ORGANISM: Homo sapiens

<400> SEQUENCE: 66
uguaguguuu ccuacuuuau gga                                            23

<210> SEQ ID NO 67
<211> LENGTH: 86
<212> TYPE: RNA
<213> ORGANISM: Homo sapiens

<400> SEQUENCE: 67
uggggcccug gcugggauau caucauauac uguaaguuug cgaugagaca cuacaguaua    60
gaugauguac uaguccgggc acccccc                                        86

<210> SEQ ID NO 68
<211> LENGTH: 22
<212> TYPE: RNA
<213> ORGANISM: Homo sapiens

<400> SEQUENCE: 68
ggauaucauc auauacugua ag                                             22

<210> SEQ ID NO 69
<211> LENGTH: 20
<212> TYPE: RNA
<213> ORGANISM: Homo sapiens

<400> SEQUENCE: 69
uacaguauag augauguacu                                                20

<210> SEQ ID NO 70
<211> LENGTH: 88
<212> TYPE: RNA
<213> ORGANISM: Homo sapiens

<400> SEQUENCE: 70
caccuugucc ucacggucca guuuucccag gaaucccuua gaugcuaaga uggggauucc    60
uggaaauacu guucuugagg ucaugguu                                       88

<210> SEQ ID NO 71
<211> LENGTH: 23
<212> TYPE: RNA
<213> ORGANISM: Homo sapiens

<400> SEQUENCE: 71
guccaguuuu cccaggaauc ccu                                            23

<210> SEQ ID NO 72
<211> LENGTH: 22
<212> TYPE: RNA
<213> ORGANISM: Homo sapiens

<400> SEQUENCE: 72
ggauuccugg aaauacuguu cu                                             22
```

```
<210> SEQ ID NO 73
<211> LENGTH: 68
<212> TYPE: RNA
<213> ORGANISM: Homo sapiens

<400> SEQUENCE: 73
gaggcaaagu ucugagacac uccgacucug aguaugauag aagucagugc acuacagaac      60
uuugucuc                                                               68

<210> SEQ ID NO 74
<211> LENGTH: 22
<212> TYPE: RNA
<213> ORGANISM: Homo sapiens

<400> SEQUENCE: 74
aaaguucuga gacacuccga cu                                               22

<210> SEQ ID NO 75
<211> LENGTH: 22
<212> TYPE: RNA
<213> ORGANISM: Homo sapiens

<400> SEQUENCE: 75
ucagugcacu acagaacuuu gu                                               22

<210> SEQ ID NO 76
<211> LENGTH: 75
<212> TYPE: RNA
<213> ORGANISM: Homo sapiens

<400> SEQUENCE: 76
ggcugugccg gguagagagg gcagugggag guaagagcuc uucacccuuc accaccuucu      60
ccacccagca uggcc                                                       75

<210> SEQ ID NO 77
<211> LENGTH: 23
<212> TYPE: RNA
<213> ORGANISM: Homo sapiens

<400> SEQUENCE: 77
cggguagaga gggcaguggg agg                                              23

<210> SEQ ID NO 78
<211> LENGTH: 22
<212> TYPE: RNA
<213> ORGANISM: Homo sapiens

<400> SEQUENCE: 78
uucaccaccu ucuccaccca gc                                               22

<210> SEQ ID NO 79
<211> LENGTH: 95
<212> TYPE: RNA
<213> ORGANISM: Homo sapiens

<400> SEQUENCE: 79
ccagcucggg cagccguggc caucuuacug ggcagcauug gauggaguca ggucucuaau      60
acugccuggu aaugaugacg gcggagcccu gcacg                                 95

<210> SEQ ID NO 80
<211> LENGTH: 22
<212> TYPE: RNA
```

<213> ORGANISM: Homo sapiens

<400> SEQUENCE: 80
caucuuacug ggcagcauug ga                                              22

<210> SEQ ID NO 81
<211> LENGTH: 22
<212> TYPE: RNA
<213> ORGANISM: Homo sapiens

<400> SEQUENCE: 81
uaauacugcc ugguaaugau ga                                              22

<210> SEQ ID NO 82
<211> LENGTH: 110
<212> TYPE: RNA
<213> ORGANISM: Homo sapiens

<400> SEQUENCE: 82
aaagauccuc agacaaucca ugugcuucuc uugccuuca uuccaccgga gucugucuca      60
uacccaacca gauuucagug gagugaaguu caggaggcau ggagcugaca               110

<210> SEQ ID NO 83
<211> LENGTH: 22
<212> TYPE: RNA
<213> ORGANISM: Homo sapiens

<400> SEQUENCE: 83
uccuucauuc caccggaguc ug                                              22

<210> SEQ ID NO 84
<211> LENGTH: 21
<212> TYPE: RNA
<213> ORGANISM: Homo sapiens

<400> SEQUENCE: 84
gauuucagug gagugaaguu c                                               21

<210> SEQ ID NO 85
<211> LENGTH: 110
<212> TYPE: RNA
<213> ORGANISM: Homo sapiens

<400> SEQUENCE: 85
acccggcagu gccuccaggc gcagggcagc cccugcccac cgcacacugc gcugcccag      60 acccacugug cgugugacag cggcugaucu gugccugggc agcgcgaccc               110

<210> SEQ ID NO 86
<211> LENGTH: 22
<212> TYPE: RNA
<213> ORGANISM: Homo sapiens

<400> SEQUENCE: 86
cugugcgugu gacagcggcu ga                                              22

<210> SEQ ID NO 87
<211> LENGTH: 110
<212> TYPE: RNA
<213> ORGANISM: Homo sapiens

<400> SEQUENCE: 87
ccgccccggg ccgcggcucc ugauugucca aacgcaauuc ucgagucuau ggcuccggcc     60
gagaguugag ucuggacguc ccgagccgcc gcccccaaac cucgagcggg        110

<210> SEQ ID NO 88
<211> LENGTH: 21
<212> TYPE: RNA
<213> ORGANISM: Homo sapiens

<400> SEQUENCE: 88
ugauugucca aacgcaauuc u                                        21

<210> SEQ ID NO 89
<211> LENGTH: 22
<212> TYPE: RNA
<213> ORGANISM: Homo sapiens

<400> SEQUENCE: 89
agaguugagu cuggacgucc cg                                       22

<210> SEQ ID NO 90
<211> LENGTH: 110
<212> TYPE: RNA
<213> ORGANISM: Homo sapiens

<400> SEQUENCE: 90
ugaacaucca ggucgggggc augaaccugg cauacaaugu agauuucugu guucguuagg    60
caacagcuac auugucugcu ggguuucagg cuaccuggaa acauguucuc               110

<210> SEQ ID NO 91
<211> LENGTH: 22
<212> TYPE: RNA
<213> ORGANISM: Homo sapiens

<400> SEQUENCE: 91
accuggcaua caauguagau uu                                       22

<210> SEQ ID NO 92
<211> LENGTH: 23
<212> TYPE: RNA
<213> ORGANISM: Homo sapiens

<400> SEQUENCE: 92
agcuacauug ucugcugggu uuc                                      23

<210> SEQ ID NO 93
<211> LENGTH: 82
<212> TYPE: RNA
<213> ORGANISM: Homo sapiens

<400> SEQUENCE: 93
gcuucgcucc ccuccgccuu cucuucccgg uucuucccgg agucgggaaa agcugggung    60
agagggcgaa aaaggaugag gu                                       82

<210> SEQ ID NO 94
<211> LENGTH: 22
<212> TYPE: RNA
<213> ORGANISM: Homo sapiens

<400> SEQUENCE: 94
aaaagcuggg uugagagggc ga                                       22

<210> SEQ ID NO 95

```
<211> LENGTH: 79
<212> TYPE: RNA
<213> ORGANISM: Homo sapiens

<400> SEQUENCE: 95
aauuaauccc ucucuuucua guucuuccua gagugaggaa aagcuggguu gagagggcaa      60
acaaauuaac uaauuaauu                                                  79

<210> SEQ ID NO 96
<211> LENGTH: 138
<212> TYPE: RNA
<213> ORGANISM: Homo sapiens

<400> SEQUENCE: 96
uguuauuuuu ugucuucuac cuaagaauuc ugucucuuag gcuuucucuu cccagauuuc      60
ccaaaguugg gaaaagcugg guugagaggg caaaaggaaa aaaaaagaau ucugucucug     120
acauaauuag auagggaa                                                  138

<210> SEQ ID NO 97
<211> LENGTH: 22
<212> TYPE: RNA
<213> ORGANISM: Homo sapiens

<400> SEQUENCE: 97
aaaagcuggg uugagagggc aa                                              22

<210> SEQ ID NO 98
<211> LENGTH: 88
<212> TYPE: RNA
<213> ORGANISM: Homo sapiens

<400> SEQUENCE: 98
uuugcauuaa aaaugaggcc uucucuuccc aguucuuccc agaucagga aaagcugggu      60 ugagagggua gaaaaaaaau gauguagg                                        88

<210> SEQ ID NO 99
<211> LENGTH: 50
<212> TYPE: RNA
<213> ORGANISM: Homo sapiens

<400> SEQUENCE: 99
cuucucuuuc caguucuucc cagaauuggg aaaagcuggg uugagagggu                50

<210> SEQ ID NO 100
<211> LENGTH: 20
<212> TYPE: RNA
<213> ORGANISM: Homo sapiens

<400> SEQUENCE: 100
aaaagcuggg uugagagggu                                                 20

<210> SEQ ID NO 101
<211> LENGTH: 48
<212> TYPE: RNA
<213> ORGANISM: Homo sapiens

<400> SEQUENCE: 101
uucucguccc aguucuuccc aaaguugaga aaagcugggu ugagagga                  48

<210> SEQ ID NO 102
<211> LENGTH: 48
```

```
<212> TYPE: RNA
<213> ORGANISM: Homo sapiens

<400> SEQUENCE: 102
uucucuuccc aguucuucuu ggagucagga aaagcuggu ugagagga        48

<210> SEQ ID NO 103
<211> LENGTH: 19
<212> TYPE: RNA
<213> ORGANISM: Homo sapiens

<400> SEQUENCE: 103
aaaagcuggg uugagagga                                        19

<210> SEQ ID NO 104
<211> LENGTH: 53
<212> TYPE: RNA
<213> ORGANISM: Homo sapiens

<400> SEQUENCE: 104
gccuucucuu cccaguucuu ccuggagucg gggaaaagcu ggguugagaa ggu  53

<210> SEQ ID NO 105
<211> LENGTH: 18
<212> TYPE: RNA
<213> ORGANISM: Homo sapiens

<400> SEQUENCE: 105
aaagcugggu ugagaagg                                         18

<210> SEQ ID NO 106
<211> LENGTH: 83
<212> TYPE: RNA
<213> ORGANISM: Homo sapiens

<400> SEQUENCE: 106
cugacuaugc cuccccgcau ccccuagggc auugguguaa agcuggagac ccacugcccc  60
aggugcugcu gggggguugua guc                                        83

<210> SEQ ID NO 107
<211> LENGTH: 23
<212> TYPE: RNA
<213> ORGANISM: Homo sapiens

<400> SEQUENCE: 107
cgcauccccu agggcauugg ugu                                   23

<210> SEQ ID NO 108
<211> LENGTH: 20
<212> TYPE: RNA
<213> ORGANISM: Homo sapiens

<400> SEQUENCE: 108
acugccccag gugcugcugg                                       20

<210> SEQ ID NO 109
<211> LENGTH: 83
<212> TYPE: RNA
<213> ORGANISM: Homo sapiens

<400> SEQUENCE: 109
cgccggccga ugggcgucuu accagacaug guuagaccug gcccucuguc uaauacuguc  60
```

```
ugguaaaacc guccauccgc ugc                                           83

<210> SEQ ID NO 110
<211> LENGTH: 22
<212> TYPE: RNA
<213> ORGANISM: Homo sapiens

<400> SEQUENCE: 110
uaauacuguc ugguaaaacc gu                                            22

<210> SEQ ID NO 111
<211> LENGTH: 72
<212> TYPE: RNA
<213> ORGANISM: Homo sapiens

<400> SEQUENCE: 111
cuugggaaug gcaaggaaac cguuaccauu acugaguuua guaaugguaa ugguucucuu   60
gcuauaccca ga                                                       72

<210> SEQ ID NO 112
<211> LENGTH: 22
<212> TYPE: RNA
<213> ORGANISM: Homo sapiens

<400> SEQUENCE: 112
aaaccguuac cauuacugag uu                                            22

<210> SEQ ID NO 113
<211> LENGTH: 68
<212> TYPE: RNA
<213> ORGANISM: Homo sapiens

<400> SEQUENCE: 113
uggguauagc aagagaacca uuaccauuac uaaacucagu aaugguaacg guuccuugc    60 cauuccca                                                            68

<210> SEQ ID NO 114
<211> LENGTH: 22
<212> TYPE: RNA
<213> ORGANISM: Homo sapiens

<400> SEQUENCE: 114
uagcaagaga accauuacca uu                                            22

<210> SEQ ID NO 115
<211> LENGTH: 68
<212> TYPE: RNA
<213> ORGANISM: Homo sapiens

<400> SEQUENCE: 115
gcauccugua cugagcugcc ccgaggcccu ucaugcugcc cagcucgggg cagcucagua   60
caggauac                                                            68

<210> SEQ ID NO 116
<211> LENGTH: 22
<212> TYPE: RNA
<213> ORGANISM: Homo sapiens

<400> SEQUENCE: 116
uccuguacug agcugccccg ag                                            22
```

```
<210> SEQ ID NO 117
<211> LENGTH: 21
<212> TYPE: RNA
<213> ORGANISM: Homo sapiens

<400> SEQUENCE: 117
cggggcagcu caguacagga u                                              21

<210> SEQ ID NO 118
<211> LENGTH: 88
<212> TYPE: RNA
<213> ORGANISM: Homo sapiens

<400> SEQUENCE: 118
ucucaggcug ugacccucua gagggaagcg cuuucuguug gcuaaaagaa aagaaagcgc    60
uucccuucag aguguuaacg cuuugaga                                       88

<210> SEQ ID NO 119
<211> LENGTH: 22
<212> TYPE: RNA
<213> ORGANISM: Homo sapiens

<400> SEQUENCE: 119
cucuagaggg aagcgcuuuc ug                                             22

<210> SEQ ID NO 120
<211> LENGTH: 21
<212> TYPE: RNA
<213> ORGANISM: Homo sapiens

<400> SEQUENCE: 120
aaagcgcuuc ccuucagagu g                                              21

<210> SEQ ID NO 121
<211> LENGTH: 97
<212> TYPE: RNA
<213> ORGANISM: Homo sapiens

<400> SEQUENCE: 121
cugcuccuuc ucccauaccc auugcauauc ggaguuguga auucucaaaa caccuccugu    60
gugcauggau uacaggaggg ugagccuugu caucgug                             97

<210> SEQ ID NO 122
<211> LENGTH: 22
<212> TYPE: RNA
<213> ORGANISM: Homo sapiens

<400> SEQUENCE: 122
uacccauugc auaucggagu ug                                             22

<210> SEQ ID NO 123
<211> LENGTH: 21
<212> TYPE: RNA
<213> ORGANISM: Homo sapiens

<400> SEQUENCE: 123
accuccugug ugcauggauu a                                              21
```